US007915485B2

(12) United States Patent
Jensen et al.

(10) Patent No.: US 7,915,485 B2
(45) Date of Patent: Mar. 29, 2011

(54) NOD-FACTOR PERCEPTION

(75) Inventors: Jens Stougaard Jensen, Hojbjerg (DK); Lene Heegaard Madsen, Hojbjerg (DK); Elena Simona Radutoiu, Hojbjerg (DK); Esben Bjorn Madsen, Risskov (DK); Niels Norgaard Sandel, Tilst (DK)

(73) Assignee: Aarhus University, Århus (DK)

( * ) Notice: Subject to any disclaimer, the term of this patent is extended or adjusted under 35 U.S.C. 154(b) by 758 days.

(21) Appl. No.: 10/563,194

(22) PCT Filed: Jul. 2, 2004

(86) PCT No.: PCT/DK2004/000478
§ 371 (c)(1),
(2), (4) Date: May 30, 2006

(87) PCT Pub. No.: WO2005/003338
PCT Pub. Date: Jan. 13, 2005

(65) Prior Publication Data
US 2008/0172763 A1 Jul. 17, 2008

Related U.S. Application Data

(60) Provisional application No. 60/484,923, filed on Jul. 3, 2003.

(30) Foreign Application Priority Data

Jul. 3, 2003 (DK) .................................. 2003 01010

(51) Int. Cl.
*A01H 1/00* (2006.01)
*C07H 21/04* (2006.01)
*C07K 14/415* (2006.01)
*C12N 15/29* (2006.01)

(52) U.S. Cl. ........... 800/295; 435/6; 435/69.1; 435/468; 435/419; 435/320.1; 530/370; 536/23.6; 800/278

(58) Field of Classification Search ............. 435/6, 69.1, 435/468, 419, 252.3, 320.1; 530/370; 536/23.2, 536/23.6; 800/278, 295

See application file for complete search history.

(56) References Cited

U.S. PATENT DOCUMENTS 6,465,716 B2 * 10/2002 Etzler et al. ................... 800/278

FOREIGN PATENT DOCUMENTS
WO WO02/102841 A2 12/2002

OTHER PUBLICATIONS

Niebel et al., MPMI, vol. 10, No. 1, Jan. 1997, pp. 132-134.*
Krusell et al., Nature, vol. 420, No. 6914, Nov. 28, 2002, pp. 422-426.*
Lange et al., Plant Science, vol. 142, No. 2, Mar. 29, 1999, pp. 133-145.*
Limpens et al., Science, vol. 302, No. 5645, 2003, pp. 630-633.*
Endre et al., "A receptor kinase gene regulating symbiotic nodule development", Letters to Nature (2002); 417: 962-966.
Madsen et al., "A receptor kinase gene of the LysM type is involved in legume perception of rhizobial signals", Letters to Nature (2003); 425: 637-640.
Nakamura, Y., "Structural analysis of a Lotus japonicus genome. I. Sequence features and mapping of fifty-six TAC clones which cover the 5.4 Mb regions of the genome", Database EMBL (2001); Accession No. AP004515.
Radutolu et al., "Plant recognition of symbiotic bacteria requires two LysM receptor-like kinases", Nature (2003); 425: 585-592.
Schauser et al., "Symbiotic mutants deficient in nodule establishments identified after T-DNA transformation of Lotus japonicus", Molecular Genetics and Genomics (1998); 259: 414-423.
Shoemaker et al., "Public soybean EST project", Database EMBL (2002); Accession No. BU926725.
Stracke et al., "A plant receptor-like kinase required for both bacterial and fungal symbiosis", Nature (2002); 417: 959-961.
Amon et al., 1998, The Plant Cell, 10:781-789 "The Sex-Inducing Pheromone and Wounding Trigger the Same Set of Genes in the Multicellular Green Alga Volvox".
Bateman and Bycroft, 2000, J. Mol. Biol., 299:1113-1119 "The Structure of a LysM Domain from *E. coli* Membrane-bound Lytic Murein Transglycosylase D (MItD)".
Bateman et al., 2002, Nucleic Acids Research, 30(1):276-280 "The Pfam Protein Families Database".
Borisov et al., 2000, Czech J. Genet. Plant Breed, 36:106-110 "Pea (*Pisum sativum* L) Mendelian Genes Controlling Development of Nitrogen-Fixing Nodules and Arbuscular Mycorrhiza".
Bras et al., 2000, MPMI, 13(4):475-479 "A *Lotus japonicus* Nodulation System Based on Heterologous Expression of the Fucosyl Transferase NodZ and the Acetyl Transferase NoIL in *Rhizobium leguminosarum*".
Broughton and Dilworth, 1971, Biochem. J., 125:1075-1080 "Control of Leghaemoglobin Synthesis in Snake Beans".
Butler et al., 1991, Eur. J. Biochem., 199:483-488 "*Kluyveromyces lactis* toxin has an essential chitinase activity".
Christensen et al., 1992, Plant Molecular Biology, 18:675-689 "Maize polyubiquitin genes: structure, thermal perturbation of expression and transcript splicing, and promoter activity following transfer to protoplasts by electroporation". Draper et al. eds., 1988, Plant Genetic Transformation and Gene Expression: A Laboratory Manual, Blackwell Scientific Publications (Book; copy provided on request).
Duc and Messager, 1989, Plant Science, 60:207-213 "Mutagenesis of Pea (*Pisum sativum* L) and the Isolation of Mutants for Nodulation and Nitrogen Fixation".
Engvild, 1987, Theor. Appl. Genet., 74:711-713 "Nodulation and nitrogen fixation mutants of pea, *Pisum sativum*".
Feinberg and Vogelstein, 1983, Analytical Biochemistry, 132(1):6-13 "A Technique for Radiolabeling DNA Restriction Endonuclease Fragments to High Specific Activity".
Feinberg and Vogelstein, 1984, Addendum. Analytical Biochemistry, 137(1):266-267Addendum to "A Technique for Radiolabeling DNA Restriction Endonuclease Fragments to High Specific Activity".

(Continued)

*Primary Examiner* — Phuong T Bui
(74) *Attorney, Agent, or Firm* — Faegre & Benson LLP

(57) ABSTRACT

The present invention provides a Nod-factor binding element, comprising one or more NFR polypeptides encoded by NFR genes, that are useful for providing non-nodulating plants with Nod-factor binding properties and triggering the endosymbiotic signalling pathway leading to nodulation. Furthermore the invention is useful for breeding for improved nodulation in nodulating legumes.

63 Claims, 13 Drawing Sheets

OTHER PUBLICATIONS

Gerard et al., 2000, Molecular Diagnosis, 5(1):39-46 "Mitochondrial ATP Synthase 6 as an Endogenous Control in the Quantitative RT-PCR Analysis of Clinical Cancer Samples".

Geurts and Bisseling, Supplement 2002, The Plant Cell, S239-S249 "Rhizobium Nod Factor Perception and Signalling".

Goddemeier et al., 1998, Plant Molecular Biology, 36:799-802 "Root-specific expression of a *Zea mays* gene encoding a novel glycine-rich protein, zmGRP3".

Handberg and Stougaard, 1992, The Plant Journal, 2(4):487-496 "*Lotus japonicus*, an autogamous, diploid legume species for classical and molecular genetics".

Hiei et al., 1994, The Plant Journal, 6(2):271-282 "Efficient transformation of rice (*Oryza sativa* L.) mediated by Agrobacterium and sequence analysis of the boundaries of the T-DNA".

Hirsch et al., 2001, Plant Physiology, 127:1484-1492 "What Makes the Rhizobia-Legume Symbiosis So Special?".

Huse and Kuriyan, 2002, Cell, 109:275-282 "The Conformational Plasticity of Protein Kinases".

Imaizumi-Anraku et al., 1997, Plant Cell Physiol., 38(7):871-881 "Two Ineffective-Nodulating Mutants of *Lotus japonicus*—Different Phenotypes Caused by the Blockage of Endocytotic Bacterial Release and Nodule Maturation—".

Ishida et al., 1996, Nature Biotechnology, 14:745-750 "High efficiency transformation of maize (*Zea mays* L) mediated by *Agrobacterium tumefaciens*".

Jakobsen et al., 1990, Nucleic Acids Research, 18(12):3669 "Purification of mRNA directly from crude plant tissues in 15 minutes using magnetic oligo dT micropheres".

Kellogg et al., 1994, BioTechniques, 16(6):1134-1137 "TaqStart Antibody™ . "Hot Start" PCR Facilitated by a neutralizing Monoclonal Antibody Directed Against Taq DNA Polymerase".

Kistner and Parniske, 2002, Trends in Plant Science, 7(11):511-518 "Evolution of signal transduction in intracellular symbiosis".

Kneen et al., 1994, Journal of Heredity, 85:129-133 "Non-nodulating Mutants of *Pisum sativum* (L.) cv. Sparkle".

Lopez-Garcia et al., 2001, 183(24):8241-8252 "Improved Soybean Root Association of N-Starved *Bradyrhizobium japonicum*".

Matz et al., 1999, Nucleic Acids Research, 27(6):1558-1560 "Amplification of cDNA ends based on template-switching effect and step-out PCR".

Miki et al., 1993, "Procedures for Introducing Foreign DNA into Plants" In: Methods in Plant Molecular Biology and Biotechnology, Glick and Thompson, eds., CRC Press, Inc., Boca Raton, pp. 67-88.

Niwa et al., 2001, MPMI, 14(7):848-856 "Responses of a Model Legume *Lotus japonicus* to Lipochitin Oligosaccharide Nodulation Factors Purified from *Mesorhizobium loti* JRL501".

Ponce et al., 2000, Planta, 211:23-33 "Three maize root-specific genes are not correctly expressed in regenerated caps in the absence of the quiescent center".

Ponting et al., 1999, J. Mol. Biol., 289:729-745 "Eukaryotic Signalling Domain Homologues in Archaea and Bacterial. Ancient Ancestry and Horizontal Gene Transfer".

Poulsen and Pødenphant, 2002, MPMI, 15(4):376-379 "Expressed Sequence Tags from Roots and Nodule Primordia of *Lotus japonicus* Infected with *Mesorhizobium loti*".

Sagan et al., 1994, Plant Science, 100:59-70 "Phenotypic characterization and classification of nodulation mutants of pea (*Pisum sativum* L.)".

Sandal et al., 2002, Genetics, 161:1673-1683 "A Genetic Linkage Map of the Model Legume *Lotus japonicus* and Strategies for Fast Mapping of New Loci".

Schauser et al., 1998, Mo. Gen. Genet., 259:414-423 "Symbiotic mutants deficient in nodule establishment identified after T-DNA transformation of *Lotus japonicus*".

Schenk and Snaar-Jagalska, 1999, Biochimica et Biophysica Acta, 1449:1-24 "Signal perception and transduction: the role of protein kinases".

Schultz et al., 1998, Proc. Natl. Acad. Sci. USA, 95(11):5857-5864 "SMART, a simple modular architecture research tool: Identification of signaling domains".

Shuman, 1994, The Journal of Biological Chemistry, 269(51):32678-32684 "Novel Approach to Molecular Cloning and Polynucleotide Synthesis Using Vaccinia DNA Topoisomerase".

Steen et al., 2003. The Journal of Biological Chemistry, 278(26):23874-23881 "Cell Wall Attachment of a Widely Distributed Peptidoglycan Binding Domain Is hindered by Cell Wall Constituents".

Stougaard, 1995, Methods in Molecular Biology, vol. 49, Plant Gene Transfer and Expression Protocols, Jones, H. ed., Humana Press Inc., Totowa, NJ, pp. 49-61 "*Agrobacterium rhizogenes* as a Vector for Transforming Higher Plants—Application in *Lotus corniculatus* Transformation".

Stougaard et al., 1987, Mol. Gen. Genet., 207:251-255 "The *Agrobacterium rhizogenes* pRi TL-DNA segment as a gene vector system for transformation of plants".

Stracke et al., 2002, Nature, 417:959-962 "A plant receptor-like kinase required for both bacterial and fungal symbiosis".

Szczyglowski et al., 1998, MPMI, 11(7):684-697 "Nodule Organogenesis and Symbiotic Mutants of the Model Lugume *Lotus japonicus*".

Vos et al., 1995, Nucleic Acids Research, 23(21):4407-4414 "AFLP: a new techniquie for DNA fingerprinting".

Vos, 1998, From: Methods in Molecular Biology, vol. 82: Arabidopsis Protocols, Martinez-Zapater, J. and J. Salinas eds., Humana Press Inc., Totowa, NJ, pp. 147-155.

Webb et al., 2000, MPMI, 13(6):606-616 "*Mesorhizobium loti* Increases Root-Specific Expression of a Calcium-Binding Protein Homologue Identified by Promoter Tagging in *Lotus japonicus*".

Markmann et al., "Functional Adaptation of a Plant Receptor-Kinase Paved the Way for the Evolution of Intracellular Root Symbioses with Bacteria," PLOS Biology, Mar. 2008, vol. 6:3, #68, p. 0497-0506.

Radutoiu et al., "LysM Domains Mediate Lipochitin-Oligosaccharide Recognition and Nfr Genes Extend the Symbiotic Host Range," The EMBO Journal, 2007, 26, p. 3923-3935.

* cited by examiner

Figure 2 a

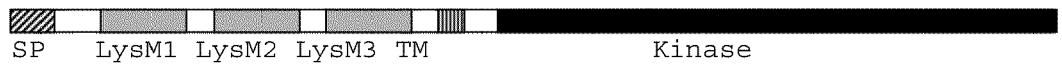

SP  LysM1 LysM2 LysM3 TM          Kinase b

| | |
|---|---|
| MAVFFLTSGSLSLFLALTLLFTNIAA | SP |
| RSEKISGPDFSCPVDSPPSCETYVT | 51 aa |
| YTAQSPNLLSLTNISDIFDISPLSIARASNIDAGKDKLVPGQVLLVP | LysM1 |
| VTCGCAGNHSSANTS | 113 aa |
| YQIQLGDSYDFVATTLYENLTNWNIVQASNPGVNPYLLPERVKVVFP | LysM2 |
| LFCRCPSKNQLNKGIQYLIT | 180 aa |
| YVWKPNDNVSLVSAKFGASPADILTENRYGQDFTAATNLPILIP | LysM3 |
| VTQLPELTQPSSNGRKSSIHLL | 246 aa |
| VILGITLGCTLLTAVLTGTLVYVYC | TM |
| RRKKALNRTASSAETADKL<u>LSGVSGYV</u>SKPNVYEIDEI<br>                   I<br>MEATKDFSDECKVGESVYKANIEGRVV<u>AVK</u>KI<u>K</u>EGGAN<u>EE</u>LKILQKV<br>                          II    III<br><u>NHGNLVKLM</u>GVSSGYDGNCFLVY<u>E</u>YAENGSLAEWLFSKSSGTPNS<u>LT</u><br>    IV                   V<br><u>WSQRISIAVDVAVGLQYM</u>HEHTYPRI<u>IHRDITTSNILLD</u>SNFKAKIA<br>    VIa                  VIb<br><u>NFA</u>MARTSTNPMMPKI<u>DVFAFG</u>VLLIELLTGRKAMTTKENGEVVMLW<br>VII              IX<br>KDMWEIFDIEENREERIRKWMDPNLESFYHIDNALSLASLAVNCTAD | KD |
| KSLS<u>RP</u>SMAEIVLSLSFLTQQSSNPTLERSLTSSGLDVEDDAHIVTS<br>    XI<br>ITAR | 595 aa |

Figure 2 c

```
NFR5M1     52:YTAQSPNLLSLTNISDIFDISPLSIARASNIDAGKDKLVPGQVLLVP:98
SYM10M1    52:YFARSPNFLSLTNISDIFDMSPLSIAKASNIEDEDKKLVEGQVLLIP:98
M.tM1      53:YRAQSPNFLSLSNISDIFNLSPLRIAKASNIEAEDKKLIPDQLLLVP:99
RiceM1     47:YRTQSPGFLDLGNISDLFGVSRALIASANKLTTEDGVLLPGQPLLVP:93

NFR5M2    114:YQIQLGDSYDFVATTLYENLTNWNIVQASNPGVNPYLLPERVKVVFP:160
SYM10M2   114:YTIKLGDNYFIVSTTSYQNLTNYVEMENFNPNLSPNLLPPEIKVVVP:160
M.tM2     115:YSIKQGDNFFILSITSYQNLTNYLEFKNFNPNLSPTLLPLDTKVSVP:161
RiceM2    109:YPIRPRDTFFGLAVTAFENLTDFVLVEELNPAAEATRLEPWQEVVVP:155
VolvoxM2  106:YTIQPGDTFWAIAQR.RG..TTVDVIQSLNPGVNPARLQVGQVINVP:149
Pfam        1:YTVKKGDTLWKIARR.YG..ISVSELKSLN.GLSSDNLYVGQKLKIP:43

NFR5M3    181:YVWKPNDNVSLVSAKFGASPADILTENRYGQDFTAATNLPILIP:224
SYM10M3   181:YVWQANDNVTRVSSKFGASQVDMFTEN..NQNFTASTNVPILIP:222
M.tM3     182:YVWQDNDNVTLVSSKFGASQVEMLAEN..NHNFTASTNRSVLIP:223
RiceM3    176:YVWQPGDDVSVVSALMNASAANIAASNGVAGNSTFATGQPVLIP:219
``` d

```
              VII                    VIII              IX
Cons       ...DFG................APE...........D.W..G Smart  195:KIADFGLSR..DLYSDDYYKVKGGKLPIRWMAPESLKEGKFTSKSDVWSFG:248
Arab   500:KIANFGVARILDEGDLDLQLTRHVEGTQGYLAPEYVENGVITSKLDVFAFG:550
NFR5   448:KIANFAMARTSTN.........................PMMPKIDVFAFG:472
SYM10  449:KIANFSMARTSTN.........................SMMPKIDVFAFG:473
M.t    450:KIANFGMARTSTN.........................SMMPKIDVFAFG:474
Rice   476:KLSNFSLAKPAAMVD........................AAATSSDVFAFG:502
```

Figure 3

```
              .    10       .    20       .    30       .    40       .    50       .    60       .    70       .    80
Lotus   1:MAVFFLTSGSLSLFLIALT..LLFTNIAARSEKISGPDPSCPVDSPPSCETYYVTTAQSPNLLSLTNISDIPDISPLSIARA: 79
Pea     1:MAIFFLESSHALFLIALM..PFVTNISAQFLQLSGTNFSCPVDSPPSCETYYVTYFARSPNFLSLTNISDIPDMSPLSIAEA: 79
M.t     1:MEAFFLESSHALPLVEMLPFLTNISAQFLYISETNFTCPVDSPPSCETYVAYFAQSPNFLSLSNISDIPNLSPLEIAEA: 80

.    90       .   100       .   110       .   120       .   130       .   140       .   150       .   160
Lotus  80:SNIDGKDKLVEGQVLLNPFVTCCAGNHESANTSYQIQLQDSYDPVGTTLYEMLITMWNIVQASMPGWNFYLLPERVKVVP:159
Pea    80:SNIEDEDKELVEGQVLLIPYVTCCSCTPNRYFANFTYTIKLSDNYFIVSTTSYQNLTNYVEMENFMPNLSPMLLPPEIKVVV:159
M.t    81:SNIEAEDEKLIPDQLLEWFVTCGCTENHSFAMITESIKQGDNFFLISITSYQNLTNYLEFKNFNFNLSPTLLPDTKVSV:160

.   170       .   180       .   190       .   200       .   210       .   220       .   230       .   240
Lotus 160:PLPCRCPSKNQLNKGICLLITYVWKPNDNVSLVSAKFGASPADILTENFYGQDFTAATMLPILIPYTQLPELTQPSSNGR:239
Pea   160:PLPCKCPSKNQLSKGIKHLITTYVWQAMDNVTFVSSKFGASQVDMPTEN..MQNFTASTNVPILLIPVTKLPVIDPSSNGR:237
M.t   161:PLPCKCPSKNQLNKGIKYLITTYVWQDMDNVTLVSSKPGASQVEMLARN..MHNFPTASTNRSVLIPVTSLPKLDQPSSNGR:239

.   250       .   260       .   270       .   280       .   290       .   300       .   310       .   320
Lotus 240:K..SSIHLLVILGITLGSTLLTAVLFGTLVYVYCRRKEALNETASSABTADEXLLSGVSGYVSEPNYYBIDEIMEATEDPSD:318
Pea   238:KNSTQKEAPIIGISLGCAPFVVLTISLVYVYCLMMERLNRSTSLABTADEKLLSGVSGYVSKFTMYBMDAIMEATMMLSE:317
M.t   239:KSSSQNLALIIGISIGSAPPILVLITSLVYVYCLMMERLNRSTSSETADEKLLSGVSGYVSKFTMYBIDAIMEGTTMLSD:318

.   330       .   340       .   350       .   360       .   370       .   380       .   390       .   400
Lotus 319:ECKVGRSVYKANIEGKVVAVKKIIEGGANEELKILQKVNHGMLVKLMGVSSGYLDQNCFLVYEYAERGSLAEWLFSKESGT:398
Pea   318:NCKIGESVYKANIDGRVLAVKKIKKD..ASBELKILQKVNHGMNLVKLMGVSSDNBGNCPLVYBYAERNGSLDEWLFSELSKT:396
M.t   319:NCKIGESVYKANEDGRVLAVKKIKKD..ASBELKILQKVNHGMNCMLVKLMGVSSDNDGNCFLVYBYAERNGSLBEWLFSESSKT:397

.   410       .   420       .   430       .   440       .   450       .   460       .   470       .   480
Lotus 399:PN...SLTWSQRISIAVDVAVGLQYMEHTYPRIIHRDITTSNILLDSNFFAKIANFAMARTSTNPMMPKIDVFAPGVLL:475
Pea   397:SMSVVSLTWSQRITVAVDVAVGLQYMHEHTYPRIIHRDITTSNILLDSNFFAKIANFSMARTSTNSMMPKIDVFAPGVYL:476
M.t   398:SMSVVSLTWSQRITIAMDVAIGLQYMHEHTYPRIIHRDITTSNILLGSNFFAKIANFGMARTSTNSMMPKIDVFAPGVVL:477

.   490       .   500       .   510       .   520       .   530       .   540       .   550       .   560
Lotus 476:IBLLTGRKAMTTKENCEVVMLNKDMWEIFDIBENREERIEKWMDPNLESFYHIDNALSLAGSLAVNCTADKSLSRPSMAEI:555
Pea   477:IBLLTGEKAITTMENGEVVILNWKDFWKIFDLBGNREEBSLRKWMDPKLENFYPIDNALSLASLAVNCTADKSLSRPSIAEI:556
M.t   478:IBLLTGEKAMTTKENCEVVILMWKDFWKIFDLBGNREEBRLRKWMDPKLESFYPIDNALSLAGSLAVNCTADKSLSRPTIAEI:557

.   570       .   580       .   590       .   600
Lotus 556:VLSLSFETQQSSNFTLERSLTSSGLDVEDDAHIVESITFAR:595
Pea   557:VLCLSLLNQSSSEPMLERSLTS.GLDVEA.THVVESIVAR:594
M.t   558:VLCLSLENQDSSEPMLERSLTS.GLDAEA.THVVESVIAR:595
```

Figure 6a

| | |
|---|---|
| MKLKTGLLLFFILLLGH | SP |
| VCFHVESNCLKGCDLALASYYILPGVFILQNITTFMQSEIVSSNDAITS<br>YNKDKILNDINIQSFQRLNIPFPCDCIGGEFLGHVFE | 103 |
| YSASKGDTYETIANLYYANLTTVDLLKRFNSYDPKNIPVNAKVNVT | LysM1 |
| VNCSCGNSQVSKDYGLFIT | 168 |
| YPIRPGDTLQDIANQSSLDAGLIQSFNPSVNFSKDSGIAFIP | LysM2 |
| GRYKNGVYVPLYHR | 224 |
| TAGLASGAAVGISIAGTFVLLLLAFCMYV | TM |
| RYQKKEEEKAKLPTDISMALSTQD(GN)ASSSAEYETSGSSGPGTASAT<br>GLTSIMVAKSMEFSYQELAKATNN | 332(324) |
| FSLDNKIGQGGFGAVYYAELRGKKTAIKKMDVQASTEFLCELKVLTHV<br>        I                 II           III<br>HHLNLVRLIGYCVEGSLFLVYEHIDNGNLGQYLHGSGKEPLPWSSRVQIA<br>    IV             V                     VIa<br>LDAARGLEYIHEHTVPVYIHRDVKSANILIDKNLRGKVADFGLTKLIEVG<br>        VIa            VIb         VII<br>NSTLQTRLVGTFGYMPPEYAQYGDISPKIDVYAFGVVLFELISAKNAVLKT<br>          VIII    \*         IX<br>GELVAESKGLVALFEEALNKSDPCDALRKLVDPRLGENYPIDSVLKIAQLG<br>   \*<br>RACTRDNPLLRPSMRSLVVALMTLSSLTEDCDDESSYESQTLINLLSVR\*<br>          XI | KD<br><br><br><br><br><br>621(623) |

Figure 6b

```
SMART0257          YTVKKGDTLSSIARRYGISVS--DLLELNNILDPDNLQVGQKLKIP-
NFR1-M1      104-YSASKGDTYETIANLYYANLTTVDLLKRFNSYDPKNIPVNAKVNVT--149
At21630-M1   105-YSVRQEDTYERVAISNYANLTTMESLQARNPFPATNIPLSATLNVLV-151

SMART 0257         YTVKKGDTLSSIARRYGISVSDLLELNN-ILDPDNLQVG1KLKIP
NFR1-M2      167-YPIRPGDTLQDIANQSSLDAGLIQSFNP-SVNFSKDSG--IAFIP-208
At21630-M2   170-YPLRPEDSLSSIARSSGVSADILQRYNP-GVNFNSGNG--IVYVP-211
BAB89226-M2  168-YAVQDGDTLGNIASLFRSSWKDILDLNPRVANPDFIKPGWILFIP-212
Volvox  M     42-YTIQPGDTFWAIAQRRGTTVDVIQSLNP-GVNPARLQVGQVINVP-85
```

Figure 11

```
NFR1    1:MK...LKTG.LLLFPILLLGHVCPHVESNCLKG....C..D..LALASYIL....PGVFLQMITTFMQSEIVSSNDAITSYNKDKILMDINIQSFQRL
NFR5    1:MAVFFLTSGSLSLFLALTLLFTNIAARSBKISGPDFSCPVDSPPSCETYVTYTAQSPNLLSLTNISDIFDISPLSIARAS...NIDAGK.DKLVPG.QVL

NFR1   85:NIPPFCDCIGGEPLGHVFEYSASKGDTYETIAMLYYANLTTVDLLKBFN.SYDPKNIPVNAKVNVTVNCSCGNS.QVSKDYGLFITTPIRPGDTLQDIAN
NFR5   96:LVPVTCGCAGMHSSANT.SYQIQLGDSYDFVATTLYEMLTNWNIVQASNPGVNPYLLPERVKVVFPLFCRCPSKNQLNKGIQYLITYVWKPMDNVSLVSA

NFR1  183:QSSLDAGLIQSFN.PSVNFSKDSGI.AFIPGRYKNGVYVPLYHRTAGLASQAAVGISIAGTFVLLLLAFCMYVRYQKKEEKAKLPTDISMALSTQDASS
NFR5  195:KFGASPADILTENKYGQDFTAATNLPILIP...VT..QLPELTQPS..SNGRKS..SIHLLVILGITLGCTLL.TAVLTGTLVYYCRRKKALM.RTASS

NFR1  281:SABYETSGSSGPGTASATGLTSIMVAKSMEPSYQELAKATMNFSLDNKIGQGGFGAVYYAELRGKKTAIKKMDVQASTEFLCELKVLTHVHHLMLVRLIG
NFR5  283:ARTADKLLSG.....VSGY.....VSKPNVYEIDEIMEATKDFSDECKVGES....VTKANIEGRVVAVKKIKEGGANE...BLEILQKVMHGMLVKLMG

NFR1  381:YC..VEGSLFLVYEHIDNRGNLGQYLHG.SGEEP..LPWSSRVQIALDAARGLEYIHBHTVPVYIHRDVKSANILIDKNLRGKVADFGLTKLIEVGNSTLQ
NFR5  367:VSSGYDGNCFLVYEYAENGSLAEWLFSKSSSTPMSLTWSQRISIAVDVAVGLQYMHEHTYPRIIHRDITTSNILLDSTFKAXIANFAMAR....TST..

NFR1  476:TRLNGTFGYMPPEYAQYGDISPKIDVYAFGVVLFELISAKNAVL..KTGRLVAESKGLVALFEEALMKSDPCDALRKLVDPFLGEMYPIDSVLKIAQLGR
NFR5  459:.......MMPKIDVFAFGVLLIEILLTGRKAMTTKENGEVVMLWKDMWEIFDIEENR...EERIRKWMDPNLESFYHIDNALSLASLAV

NFR1  574:ACTRDNPLLRPSMRSLNVALMTLSSLTEDCDIDESSYES........QTLIRLLSVR
NFR5  540:NCTADKSLSRPSMAEIVLSLSFLTQQSSNPTLERSLTSSGLDVEDDAHIVTSITAR
```

Protein domain structure of *Lotus japonicus* and *Lotus filicaulis* NFR1 and NFR5 proteins and of the hybrid proteins

```
                         SEQUENCE LISTING

<160> NUMBER OF SEQ ID NOS: 62

<210> SEQ ID NO 1
<211> LENGTH: 45
<212> TYPE: DNA
<213> ORGANISM: Lotus japonicus

<400> SEQUENCE: 1
ctaatacgac tcactatagg gcaagcagtg gtaacaacgc agagt             45

<210> SEQ ID NO 2
<211> LENGTH: 29
<212> TYPE: DNA
<213> ORGANISM: Lotus japonicus

<400> SEQUENCE: 2
gctagttaaa aatgtaatag taaccacgc                               29

<210> SEQ ID NO 3
<211> LENGTH: 21
<212> TYPE: DNA
<213> ORGANISM: Lotus japonicus

<400> SEQUENCE: 3
aaagcagcat tcatcttctg g                                       21

<210> SEQ ID NO 4
<211> LENGTH: 39
```

```
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(39)
<223> OTHER INFORMATION: Oligo dT primer

<400> SEQUENCE: 4
gaccacgcgt atcgatgtcg actttttttt tttttttttv                   39

<210> SEQ ID NO 5
<211> LENGTH: 19
<212> TYPE: DNA
<213> ORGANISM: Lotus japonicus

<400> SEQUENCE: 5
gcaagggaag gtaattcag                                          19

<210> SEQ ID NO 6
<211> LENGTH: 2292
<212> TYPE: DNA
<213> ORGANISM: Lotus japonicus

<400> SEQUENCE: 6
ttattgatat actaaaccac aggatatttt attgacaatg tgaatgttcc atattttcaa    60
caatgctgat tccctctgat aaagaacaag ttccttttct ctttccctgt taactatcat   120
ttgttcccca cttcacaaac atggctgtct tctttcttac ctctggctct ctgagtcttt   180
ttcttgcact cacgttgctt ttcactaaca tcgccgctcg atcagaaaag attagcggcc   240
cagactttc atgccctgtt gactcacctc cttcttgtga acatatgtg acatacacag    300
ctcagtctcc aaatcttctg agcctgacaa acatatctga tatatttgat atcagtcctt   360
tgtccattgc aagagccagt aacatagatg cagggaagga caagctggtt ccaggccaag   420
tcttactggt acctgtaact tgcggttgcg ccggaaacca ctcttctgcc aatacctcct   480
accaaatcca gctaggtgat agctacgact tgttgcaac cactttatat gagaaccctta  540
caaattggaa tatagtacaa gcttcaaacc caggggtaaa tccatatttg ttgccagagc   600
gcgtcaaagt agtattccct ttattctgca ggtgccctct aaagaaccag ttgaacaaag   660
ggattcagta tctgattact tatgtgtgga agcccaatga caatgtttcc cttgtgagtg   720
ccaagtttgg tgcatcccca gcggacatat tgactgaaaa ccgctacggt caagacttca   780
ctgctgcaac caaccttcca attttgatcc cagtgacaca gttgccagag cttactcaac   840
cttcttcaaa tggaaggaaa agcagcattc atcttctggt tatacttggt attaccctgg   900
gatgcacgtt gctaactgca gttttaaccg ggaccctcgt atatgtatac tgccgcagaa   960
agaaggctct gaataggact gcttcatcag ctgagactgc tgataaacta ctttctggag  1020
tttcaggcta tgtaagcaag ccaaacgtgt atgaaatcga cgagataatg gaagctacga  1080
aggatttcag cgatgagtgc aaggttgggg aatcagtgta caaggccaac atagaaggtc  1140
gggttgtagc ggtaaagaaa atcaaggaag gtggtgccaa tgaggaactg aaaattctgc  1200
agaaggtaaa tcatggaaat ctggtgaaac taatgggtgt ctcctcaggc tatgatggaa  1260
actgtttctt ggtttatgaa tatgctgaaa atgggtctct tgctgagtgg ctgttctcca  1320
agtcttcagg aaccccaaac tcccttacat ggtctcaaag gataagcata gcagtggatg  1380
ttgctgtggg tctgcaatac atgcatgaac atacctatcc aagaataata cacagggaca  1440
tcacaacaag taatatcctt ctcgactcga acttcaaggc caagatagcg aatttcgcca  1500
```

```
tggccagaac ttcgaccaac cccatgatgc caaaaatcga tgtcttcgct ttcggggtgc      1560
ttctgataga gttgctcacc ggaaggaaag ccatgacaac caaggagaac ggcgaggtgg      1620
ttatgctgtg gaaggatatg tgggagatct tgacataga agagaataga gaggagagga      1680
tcagaaaatg gatggatcct aatttagaga gcttttatca tatagataat gctctcagct      1740
tggcatcctt agcagtgaat tgcacagctg ataagtcttt gtctcgaccc tccatggctg      1800
aaattgttct tagcctctcc tttctcactc aacaatcatc taaccccaca ttagagagat      1860
ccttgacttc ttctgggtta gatgtagaag atgatgctca tattgtgact tccattactg      1920
cacgttaagc aagggaaggt aattcagttt ctcatcaaat tgatcaagat gcactttgtt      1980
tgcgtggtta ctattacatt tttaactagc tatttgctta tttctctgta tttatttgtc      2040
agacactgga attgaatatc atatgatgga ggagttgtct gttaatacat gtgctaataa      2100
caaattcagg caagatagtt aattgcattt gaaatacata tttctgctca gagatggtga      2160
acatccatgc tccgaagctc atattaagtg tggtagctat tttcttttca tcttttttggg     2220 gtgaatgcgt gttcatgtaa ctcgtaaggt gttatatatt acagaagtcg tatacgtcgt      2280
tccaaaaaaa aa                                                          2292

<210> SEQ ID NO 7
<211> LENGTH: 3536
<212> TYPE: DNA
<213> ORGANISM: Lotus japonicus GIFU

<400> SEQUENCE: 7
ggacatgaga ttgaagctcc aaaattagct cttttttctg atgaatactt aatgctttgt       60
tgtattcact tgattaagtg ctagaaatca tctttgcatg atcatagatt aaatgaattt      120
ccagttggtg tgtggagagc tattttgtta tgctgacatc tgcaatttgc agggcatcta      180
atgattgtca tttcttaaat tattattggt tgtttccgtt tctttaatta tctgttttaa      240
tcttgcaggt catacaaatt aaaatactag ccaccaccca agacatacta aatggggtag      300
tagagggaag ggtaaggtcg ataaggatga ctttttattc tataaaattt aggagaattt      360
gagcttaagt ggcaaggcaa acgacattac tatacgaatt ggctttgtac cagaaacagg      420
gaacaaataa tattttacaa ataagctatt atcatgtcag ctcatttgtt caactttgat      480
ttgattaaaa attaaatgaa gttgaatttg ttgagctgct ttattatata tgccactgga      540
tgtttccgca ttctaagtgc atgtttgaaa acatttctac aattgattac gaaggaaaaa      600
ttaatcatgg agagaagctt atgtgcgtag cttctgtatt tctgaattga ttctatctgt      660
acagtagcat ttagataatg aatgatcttg gttctcgcta agcatcaaac caatctctac      720 cctttttaaaa ttgcaagaat tataagtcat gcattgaccc aaatccttct gtggttatgc      780
cccttaaaaa tccggcaaga catcaagtta gttggtcatt agggttccac cagctagctg      840
acaccttgta caacaactgg ccgtcctaaa gttgggtaag cattacaata ctaaatgcca      900
ttttattata ttttgcgcat ggttatatac ctaagtagga tttgtccaca gtttctttga      960
ttcggaaagg aaaaaatatt tagttgacac tgacagaagc agatttttata tacatatatt     1020 atgaaatgac tcctacatga gatacacgaa tctcatcccc atgagttgca gtttgacaga     1080
gtacacactt atcaacttgc tggaatatag gaaagtctaa ccaatgatgt cgatccgtat     1140
tgccttaatt ttggtaaatt tagtattaca tgatcattat tgatatacta aaccacagga     1200
tattttattg acaatgtgaa tgttccatat tttcaacaat gctgattccc tctgataaag     1260
aacaagttcc ttttctcttt ccctgttaac tatcatttgt tccccacttc acaaacatgg     1320
```

```
ctgtcttctt tcttacctct ggctctctga gtcttttcct tgcactcacg ttgcttttca     1380
ctaacatcgc cgctcgatca gaaaagatta gcggcccaga cttttcatgc cctgttgact     1440
cacctccttc ttgtgaaaca tatgtgacat acacagctca gtctccaaat cttctgagcc     1500
tgacaaacat atctgatata tttgatatca gtcctttgtc cattgcaaga gccagtaaca     1560
tagatgcagg gaaggacaag ctggttccag gccaagtctt actggtacct gtaacttgcg     1620
gttgcgccgg aaaccactct tctgccaata cctcctacca aatccagcta ggtgatagct     1680
acgactttgt tgcaaccact ttatatgaga accttacaaa ttggaatata gtacaagctt     1740
caaacccagg ggtaaatcca tatttgttgc cagagcgcgt caaagtagta ttccctttat     1800
tctgcaggtg cccttcaaag aaccagttga acaaagggat tcagtatctg attacttatg     1860
tgtggaagcc caatgacaat gtttcccttg tgagtgccaa gtttggtgca tccccagcgg     1920
acatattgac tgaaaaccgc tacggtcaag acttcactgc tgcaaccaac cttccaattt     1980
tgatcccagt gacacagttg ccagagctta ctcaaccttc ttcaaatgga aggaaaagca     2040
gcattcatct tctggttata cttggtatta ccctgggatg cacgttgcta actgcagttt     2100
taaccgggac cctcgtatat gtatactgcc gcagaaagaa ggctctgaat aggactgctt     2160
catcagctga gactgctgat aaactacttt ctggagtttc aggctatgta agcaagccaa     2220
acgtgtatga atcgacgag ataatggaag ctacgaagga tttcagcgat gagtgcaagg     2280
ttggggaatc agtgtacaag gccaacatag aaggtcgggt tgtagcggta agaaaatca     2340 aggaaggtgg tgccaatgag gaactgaaaa ttctgcagaa ggtaaatcat ggaaatctgg     2400
tgaaactaat gggtgtctcc tcaggctatg atggaaactg tttcttggtt tatgaatatg     2460
ctgaaaatgg gtctcttgct gagtggctgt tctccaagtc ttcaggaacc ccaaactccc     2520
ttacatggtc tcaaaggata agcatagcag tggatgttgc tgtgggtctg caatacatgc     2580
atgaacatac ctatccaaga ataatacaca gggacatcac aacaagtaat atccttctcg     2640
actcgaactt caaggccaag atagcgaatt tcgccatggc cagaacttcg accaacccca     2700
tgatgccaaa aatcgatgtc ttcgcttttcg gggtgcttct gatagagttg ctcaccggaa     2760
ggaaagccat gacaaccaag gagaacggcg aggtggttat gctgtggaag gatatgtggg     2820
agatctttga catagaagag aatagagagg agaggatcag aaaatggatg gatcctaatt     2880
tagagagctt ttatcatata gataatgctc tcagcttggc atccttagca gtgaattgca     2940
cagctgataa gtcttttgtct cgaccctcca tggctgaaat tgttcttagc ctctcctttc     3000
tcactcaaca atcatctaac cccacattag agagatcctt gacttcttct gggttagatg     3060
tagaagatga tgctcatatt gtgacttcca ttactgcacg ttaagcaagg gaaggtaatt     3120
cagtttctca tcaaattgat caagatgcac tttgtttgcg tggttactat tacatttta      3180 actagctatt tgcttatttc tctgtatttta tttgtcagac actggaattg aatatcatat     3240
gatggaggag ttgtctgtta atacatgtgc taataacaaa ttcaggcaag atagttaatt     3300
gcatttgaaa tacatatttc tgctcagaga tggtgaacat ccatgctccg aagctcatat     3360
taagtgtggt agctattttc tttcatctt tttggggtga atgcgtgttc atgtaactcg      3420
taaggtgtta tatattacag aagtcgtata cgtcgttcca ataattgatc aaggtacctg     3480
tctatttcgt aaaaaagcc aagtaccaac attagttgac tcgttgagag tggtgc          3536
```

<210> SEQ ID NO 8
<211> LENGTH: 595
<212> TYPE: PRT
<213> ORGANISM: Lotus japonicus

<400> SEQUENCE: 8

```
Met Ala Val Phe Phe Leu Thr Ser Gly Ser Leu Ser Leu Phe Leu Ala
1               5                   10                  15

Leu Thr Leu Leu Phe Thr Asn Ile Ala Ala Arg Ser Glu Lys Ile Ser
            20                  25                  30

Gly Pro Asp Phe Ser Cys Pro Val Asp Ser Pro Ser Cys Glu Thr
            35                  40                  45

Tyr Val Thr Tyr Thr Ala Gln Ser Pro Asn Leu Leu Ser Leu Thr Asn
    50                  55                  60

Ile Ser Asp Ile Phe Asp Ile Ser Pro Leu Ser Ile Ala Arg Ala Ser
65                  70                  75                  80

Asn Ile Asp Ala Gly Lys Asp Lys Leu Val Pro Gly Gln Val Leu Leu
                85                  90                  95

Val Pro Val Thr Cys Gly Cys Ala Gly Asn His Ser Ser Ala Asn Thr
            100                 105                 110

Ser Tyr Gln Ile Gln Leu Gly Asp Ser Tyr Asp Phe Val Ala Thr Thr
            115                 120                 125

Leu Tyr Glu Asn Leu Thr Asn Trp Asn Ile Val Gln Ala Ser Asn Pro
    130                 135                 140

Gly Val Asn Pro Tyr Leu Leu Pro Glu Arg Val Lys Val Val Phe Pro
145                 150                 155                 160

Leu Phe Cys Arg Cys Pro Ser Lys Asn Gln Leu Asn Lys Gly Ile Gln
                165                 170                 175

Tyr Leu Ile Thr Tyr Val Trp Lys Pro Asn Asp Asn Val Ser Leu Val
            180                 185                 190

Ser Ala Lys Phe Gly Ala Ser Pro Ala Asp Ile Leu Thr Glu Asn Arg
    195                 200                 205

Tyr Gly Gln Asp Phe Thr Ala Ala Thr Asn Leu Pro Ile Leu Ile Pro
210                 215                 220

Val Thr Gln Leu Pro Glu Leu Thr Gln Pro Ser Ser Asn Gly Arg Lys
225                 230                 235                 240

Ser Ser Ile His Leu Leu Val Ile Leu Gly Ile Thr Leu Gly Cys Thr
                245                 250                 255

Leu Leu Thr Ala Val Leu Thr Gly Thr Leu Val Tyr Val Tyr Cys Arg
            260                 265                 270

Arg Lys Lys Ala Leu Asn Arg Thr Ala Ser Ser Ala Glu Thr Ala Asp
    275                 280                 285

Lys Leu Leu Ser Gly Val Ser Gly Tyr Val Ser Lys Pro Asn Val Tyr
290                 295                 300

Glu Ile Asp Glu Ile Met Glu Ala Thr Lys Asp Phe Ser Asp Glu Cys
305                 310                 315                 320

Lys Val Gly Glu Ser Val Tyr Lys Ala Asn Ile Glu Gly Arg Val Val
                325                 330                 335

Ala Val Lys Lys Ile Lys Glu Gly Gly Ala Asn Glu Glu Leu Lys Ile
            340                 345                 350

Leu Gln Lys Val Asn His Gly Asn Leu Val Lys Leu Met Gly Val Ser
    355                 360                 365

Ser Gly Tyr Asp Gly Asn Cys Phe Leu Val Tyr Glu Tyr Ala Glu Asn
370                 375                 380

Gly Ser Leu Ala Glu Trp Leu Phe Ser Lys Ser Ser Gly Thr Pro Asn
385                 390                 395                 400

Ser Leu Thr Trp Ser Gln Arg Ile Ser Ile Ala Val Asp Val Ala Val
                405                 410                 415
```

-continued

```
Gly Leu Gln Tyr Met His Glu His Thr Tyr Pro Arg Ile Ile His Arg
            420                 425                 430
Asp Ile Thr Thr Ser Asn Ile Leu Leu Asp Ser Asn Phe Lys Ala Lys
        435                 440                 445
Ile Ala Asn Phe Ala Met Ala Arg Thr Ser Thr Asn Pro Met Met Pro
450                 455                 460
Lys Ile Asp Val Phe Ala Phe Gly Val Leu Leu Ile Glu Leu Leu Thr
465                 470                 475                 480
Gly Arg Lys Ala Met Thr Thr Lys Glu Asn Gly Glu Val Val Met Leu
            485                 490                 495
Trp Lys Asp Met Trp Glu Ile Phe Asp Ile Glu Glu Asn Arg Glu Glu
            500                 505                 510
Arg Ile Arg Lys Trp Met Asp Pro Asn Leu Glu Ser Phe Tyr His Ile
        515                 520                 525
Asp Asn Ala Leu Ser Leu Ala Ser Leu Ala Val Asn Cys Thr Ala Asp
530                 535                 540
Lys Ser Leu Ser Arg Pro Ser Met Ala Glu Ile Val Leu Ser Leu Ser
545                 550                 555                 560
Phe Leu Thr Gln Gln Ser Ser Asn Pro Thr Leu Glu Arg Ser Leu Thr
            565                 570                 575
Ser Ser Gly Leu Asp Val Glu Asp Asp Ala His Ile Val Thr Ser Ile
            580                 585                 590
Thr Ala Arg
        595

<210> SEQ ID NO 9
<211> LENGTH: 23
<212> TYPE: DNA
<213> ORGANISM: Pisum sativum

<400> SEQUENCE: 9
atgtctgcct tctttcttcc ttc                                              23

<210> SEQ ID NO 10
<211> LENGTH: 23
<212> TYPE: DNA
<213> ORGANISM: Pisum sativum

<400> SEQUENCE: 10
ccacacataa gtaatmagat act                                              23

<210> SEQ ID NO 11
<211> LENGTH: 3800
<212> TYPE: DNA
<213> ORGANISM: Pisum sativum

<400> SEQUENCE: 11
gtgggctata tgattggtgc gtacttcacc ttgcatgaaa tatcagcaca agtatatca        60 agtgaaaaac aatacctaaa ttccttaacc tatgatattc ttttgggaga ggttgcaaaa      120
aagttgttag ttgcagttat tatttgagtt ttgaaaatgt attgttggcc aaacattagt      180
tgatactcag gaactagctc ttgttctgat ggatacttaa tgcttcgtta tatttgta       240 ttcacttggt caagtgctag aaatcatctt ggcacaatca caggatgaat aaacctctgg      300
ttgaaagcta cattcagtcg ttgctgatt tctgcaactt gaggggaatc taatgatttt      360
tatttattat tattgctgtt gcttactgca attatcaatt cctttaatt ttttacaaa       420 acaagttggt tacaagatct ctttaatata ttgttatcag ttatcagttt cttttatgta     480
```

```
agaagggttt ctctatacgg aactataaag actaatcctt caaatcgggt gggacaacaa    540
aagcggcaaa gttgttcatg aagaattttta gcactgttgt attcttatca agtacagaaa    600
gccacactca agcaaaaaag tgtagggtaa gaacgacatc ttattctatt ttatttagta    660
ggagaagtca agcttatgtg gcgatgtaaa tgtcatttct atccaaacta tctttgtact    720
agaaataggg aacatataaa ttatggagag tttgttaagg tgttttaata tattaaaacc    780
attgtaacgg gaagtgtcaa cattgttagc tgttcattgc ctgtatatta aatagcata     840 tatataatag acttggcctt tgttaaactt taaaccatat cttttgtgag tctaccccctt   900 aaaaatatgg taaaggcatc aagttagata gtctttaggt accagccagc tagctgacat    960
tgtgtaagga catattggat tacaaaacta tattattatt accatcttta ttatattctg   1020
cgcatgattt catacttaat ttggatttgt ccagtgtcta agatttgaaa aggaaaaata   1080
gtagaactaa tgacagagac agaagcatat attttaata tcaaaccaaa agatatgtcc    1140
aaataagaga taaatataaa gtttgaggta taacaataag tcttggttgt tacttgccat   1200
aagaaactct cttttctctt ccccataact tgcatttctt cacaatttca caacaatggc   1260
tatcttcttt cttccttcta gttctcatgc ccttttttctt gcactcatgt tttttgtcac   1320
taatatttca gctcaaccat tacaactcag tggaacaaac ttttcatgcc cggtggattc   1380
acctccttca tgtgaaacct atgtgacata ctttgctcgg tctccaaact ttttgagcct    1440
aactaacata tcagatatat ttgatatgag tcctttatcc attgcaaaag ccagtaacat   1500
agaagatgag gacaagaagc tggttgaagg ccaagtctta ctcatacctg taacttgtgg   1560
ttgcactaga aatcgctatt tcgcgaattt cacgtacaca atcaagctag gtgacaacta   1620
tttcatagtt tcaaccactt cataccagaa tcttacaaat tatgtggaaa tggaaaattt   1680
caaccctaat ctaagtccaa atcattgcc accagaaatc aaagttgttg tccctttatt    1740
ctgcaaatgc ccctcgaaga atcagttgag caaaggaata aagcatctga ttacttatgt   1800
gtggcaggct aatgacaatg ttacccgtgt aagttccaag tttggtgcat cacaagtgga   1860
tatgtttact gaaaacaatc aaaacttcac tgcttcaacc aacgttccga ttttgatccc    1920
tgtgacaaag ttaccggtaa ttgatcaacc atcttcaaat ggaagaaaaa acagcactca   1980
aaaacctgct tttataattg gtattagcct aggatgtgct ttttttcgttg tagttttaac   2040 actatcactt gtttatgtat attgtctgaa aatgaagaga ttgaatagga gtacttcatt   2100
ggcggagact gcggataagt tactttcagg tgtttcgggt tatgtaagca agccaacaat   2160
gtatgaaatg gatgcgatca tggaagctac aatgaacctg agtgagaatt gtaagattgg   2220
tgaatccgtt tacaaggcta atatagatgg tagagtttta gcagtgaaaa aaatcaagaa   2280
agatgcttct gaggagctga aaattttgca gaaggtaaat catggaaatc ttgtgaaact   2340
tatgggtgtg tcttccgaca acgacggaaa ctgtttcctt gtttacgagt atgctgaaaa   2400
tggatcactt gatgagtggt tgttctcaga gtcgtcgaaa acttcgaact cggtggtctc   2460
gcttacatgg tctcagagaa taacagtagc agtggatgtt gcagttggtt tgcaatacat   2520
gcatgaacat acttacccaa gaataatcca cagagacatc acaacaagta atatccttct   2580
ggattcaaac tttaaggcca agatagcgaa tttttcaatg ccagaacatt caacaaattc   2640
catgatgccg aaaatcgatg ttttcgcttt tggggtggtt ctgattgagt tgcttaccgg   2700
caagaaagcg ataacaacga tggaaaatgg cgaggtggtt attctgtgga aggatttctg   2760
gaagattttt gatctagaag ggaatagaga agagagctta agaaaatgga tggatcctaa   2820
gctagagaat ttttatccta ttgataatgc tcttagtttg gcttctttgg cagtgaattg   2880
```

```
tactgcagat aaatcattgt caagaccaag cattgcagaa attgttcttt gtctttctct   2940
tctcaatcaa tcatcatctg aaccaatgtt agaaagatcc ttgacatctg gtttagatgt   3000
tgaagctact catgttgtta cttctatagt agctcgttga tattcattca agtgaaggta   3060
acactgaatc aatgcttcag tttcttatat tcaagatggt tactttgttt agatgattat   3120
tgattacatc tttatgtgtg aactatatg gttattttaa ttaagggaat tgttctaaaa    3180
ttcatttttc catgttattc ttttacagca tgagtttcgg taaagtgaat tgtaacctgc   3240
tattgaactc agaataattt cggttattat gttagtcatc gacactttta agaaaagtat   3300
gtttgatgtt cgatatatgt ctgacaccaa cacaacactt acaactgtga ttatgtttaa   3360
tttgtttatt tttgtgataa atcagtgttt catcatttga ttattaaggt acaattattc   3420
caaccatcct ttattaaggg cattctcttt attttttgat acaatataag acctaagtgt   3480
gaatattgaa gcttaatgga agacatgaat tttgcaagaa aggatttgga agcctttggc   3540
acccataaaa tgttgatgca agtcagctat aacttctctc ttttttctctt tttttttggg   3600 atgggatggg tattcatgta tagctaaagg cacattttaa attaaaatct tgtatatata   3660
tgcaaaagtc ttctttggtg tttcaataat tgatgaaggg accgcttacc atcgatggtt   3720
gagttaacaa taccacgtct atatatgtgg agaatctttc tcaagcatca agacttcgtt   3780
ggccagctgc taaaagacaa                                                3800

<210> SEQ ID NO 12
<211> LENGTH: 2226
<212> TYPE: DNA
<213> ORGANISM: Pisum sativum

<400> SEQUENCE: 12
ttttctcttc ctcataactt gcatttcttc acaatttcac aacaatggct atcttctttc     60
ttccttctag ttctcatgcc cttttttctt g cactcatgtt ttttgtcact aatatttcag   120
ctcaaccatt acaactcagt ggaacaaact tttcatgccc ggtggattca cctccttcat    180
gtgaaaccta tgtgacatac tttgctcggt ctccaaactt tttgagccta actaacatat    240
cagatatatt tgatatgagt cctttatcca ttgcaaaagc cagtaacata aagatgagg    300 acaagaagct ggttgaaggc caagtcttac tcatacctgt aacttgtggt tgcactagaa    360
atcgctattt cgcgaatttc acgtacacaa tcaagctagg tgacaactat ttcatagttt    420
caaccacttc ataccagaat cttacaaatt atgtggaaat ggaaaatttc aaccctaatc    480
taagtccaaa tctattgcca ccagaaatca agttgttgt cccttattc tgcaaatgcc     540 cctcgaagaa tcagttgagc aaaggaataa agcatctgat tacttatgtg tggcaggcta    600
atgacaatgt tacccgtgta agttccaagt ttggtgcatc acaagtggat atgtttactg    660
aaaacaatca aaacttcact gcttcaacca atgttccgat tttgatccct gtgacaaagt    720
taccggtaat tgatcaacca tcttcaaatg gaagaaaaaa cagcactcaa aaacctgctt    780
ttataattgg tattagccta ggatgtgctt ttttcgttgt agtttttaaca ctatcacttg    840 tttatgtata ttgtctgaaa atgaagagat tgaataggag tacttcattg gcggagactg    900
cggataagtt actttcaggt gtttcgggtt atgtaagcaa gccaacaatg tatgaaatgg    960
atgcgatcat ggaagctaca atgaacctga gtgagaattg taagattggt gaatctgttt   1020
acaaggctaa tatagatggt agagttttag cagtgaaaaa aatcaagaaa gatgcttctg   1080
aggagctgaa aattctgcag aaggtaaatc atggaaatct tgtgaaactt atgggtgtgt   1140
cttccgacaa cgaaggaaac tgtttccttg tttacgagta tgctgaaaat ggatcacttg    1200
```

```
atgagtggtt gttctcagag ttgtcgaaaa cttcgaactc ggtggtctcg cttacatggt    1260
ctcagagaat aacagtagca gtggatgttg cagttggttt gcaatacatg catgaacata    1320
cttacccaag aataatccac agagacatca caacaagtaa tatccttctg gattcaaact    1380
ttaaggccaa gatagcgaat ttttcaatgg ccagaacttc aacaaattcc atgatgccga    1440
aaatcgatgt tttcgctttt ggggtggttc tgattgagtt gcttaccggc aagaaagcga    1500
taacaacgat ggaaaatggc gaggtggtta ttctgtggaa ggatttctgg aagattttg     1560 atctagaagg gaatagagaa gagagcttaa gaaaatggat ggatcctaag ctagagaatt    1620
tttatcctat tgataatgct cttagtttgg cttctttggc agtgaattgt actgcagata    1680
aatcattgtc aagaccaagc attgcagaaa ttgttctttg tctttctctt ctcaatcaat    1740
catcatctga accaatgtta gaaagatcct tgacatctgg tttagatgtt gaagctactc    1800
atgttgttac ttctatagta gctcgttgat attcattcaa gtgaaggtaa cactaaatca    1860
atgcttcagt ttcttatatt caagatggtt actttgttta ggtgattatt gattacatct    1920
ttatgtgtgg aactatatgg ttattttaat taagggaatt agtctaaatt tcattttcc    1980 atgttattct ttaaagcacg agtttcggta aagtgaattg taacctgtta ttgagctcat    2040
aataatttca gttattatgt tagtcatcga cacttctaaa aaagtatgtc tgatgttcga    2100
tatgtgtctg acaccaacac aaccctgacc actgtgatta cgtttaattt gtttattttt    2160
gtgataaatc agtgtttcat catttgatta ttaaggtaca attattccaa ccatccttt     2220 aaaaaa                                                               2226

<210> SEQ ID NO 13
<211> LENGTH: 1968
<212> TYPE: DNA
<213> ORGANISM: Pisum sativum

<400> SEQUENCE: 13
cttgcatttc ttcacaattt cacaacaatg gctatcttct ttcttccttc tagttctcat      60 gcccttttc ttgcactcat gttttttgtc actaatattt cagctcaacc attacaactc     120
agtggaacaa acttttcatg cccggtggat tcacctcctt catgtgaaac ctatgtgaca     180
tactttgctc ggtctccaaa cttttttgagc ctaactaaca tatcagatat atttgatatg    240
agtcctttat ccattgcaaa agccagtaac atagaagatg aggacaagaa gctggttgaa     300
ggccaagtct tactcatacc tgtaacttgt ggttgcacta gaaatcgcta tttcgcgaat     360
ttcacgtaca caatcaagct aggtgacaac tatttcatag tttcaaccac ttcataccag     420
aatcttacaa attatgtgga atggaaaat ttcaaccta atctaagtcc aaatctattg       480
ccaccagaaa tcaaagttgt tgtccctta ttctgcaaat gcccctcgaa gaatcagttg      540
agcaaaggaa taagcatct gattacttat gtgtggcagg ctaatgacaa tgttacccgt      600
gtaagttcca gtttggtgc atcacaagtg gatatgttta ctgaaaacaa tcaaaacttc      660
actgcttcaa ccaacgttcc gattttgatc cctgtgacaa gttaccggt aattgatcaa     720 ccatcttcaa atggaagaaa aaacagcact caaaaacctg cttttataat tggtattagc    780
ctaggatgtg cttttttcgt tgtagtttta acactatcac ttgtttatgt atattgtctg    840
aaaatgaaga gattgaatag gagtacttca ttggcggaga ctgcgataa gttactttca    900 ggtgtttcgg gttatgtaag caagccaaca atgtatgaaa tggatgcgat catggaagct   960
acaatgaacc tgagtgagaa ttgtaagatt ggtgaatccg tttacaaggc taatatagat    1020
ggtagagttt tagcagtgaa aaaaatcaag aaagatgctt ctgaggagct gaaaattttg   1080
```

-continued

```
cagaaggtaa atcatggaaa tcttgtgaaa cttatgggtg tgtcttccga caacgacgga   1140
aactgtttcc ttgtttacga gtatgctgaa atggatcac ttgatgagtg gttgttctca    1200
gagtcgtcga aaacttcgaa ctcggtggtc tcgcttacat ggtctcagag aataacagta   1260
gcagtggatg ttgcagttgg tttgcaatac atgcatgaac atacttaccc aagaataatc   1320
cacagagaca tcacaacaag taatatcctt ctggattcaa actttaaggc caagatagcg   1380 aattttttcaa tggccagaac ttcaacaaat tccatgatgc cgaaaatcga tgttttcgct  1440
tttggggtgg ttctgattga gttgcttacc ggcaagaaag cgataacaac gatggaaaat   1500
ggcgaggtgg ttattctgtg aaggattttc tggaagattt ttgatctaga agggaataga   1560
gaagagagct taagaaaatg gatggatcct aagctagaga attttttatcc tattgataat  1620 gctcttagtt tggcttctttt ggcagtgaat tgtactgcag ataaatcatt gtcaagacca   1680
agcattgcag aaattgttct ttgtctttct cttctcaatc aatcatcatc tgaaccaatg   1740
ttagaaagat ccttgacatc tggtttagat gttgaagcta ctcatgttgt tacttctata   1800
gtagctcgtt gatattcatt caagtgaagg taacactgaa tcaatgcttc agtttcttat   1860
attcaagatg gttactttgt ttagatgatt attgattaca tctttatgtg tggaactata    1920
tggttatttt aattaaggga attgttctaa aattcatttt tccatgtt                1968
```

<210> SEQ ID NO 14
<211> LENGTH: 1938
<212> TYPE: DNA
<213> ORGANISM: Pisum sativum

<400> SEQUENCE: 14

```
tcttcacaat ttcacaacaa tggctatctt ctttcttcct tctagttctc atgcccttt       60 tcttgcactc atgttttttg tcactaatat ttcagctcaa ccattacaac tcagtggaac    120 aaactttttca tgcccggtgg attcacctcc ttcatgtgaa acctatgtga catactttgc   180
tcggtctcca aacttttttga gcctaactaa catatcagat atatttgata tgagtccttt   240
atccattgca aaagccagta acatagaaga tgaggacaag aagctggttg aaggccaagt    300
cttactcata cctgtaactt gtggttgcac tagaaatcgc tatttcgcga atttcacgta    360
cacaatcaag ctaggtgaca actatttcat agtttcaacc acttcatacc agaatcttac    420
aaattatgtg gaaatggaaa atttcaaccc taatctaagt ccaaatctat tgccaccaga    480
aatcaaagtt gttgtccctt tattctgcaa atgcccctcg aagaatcagt tgagcaaagg    540
aataaagcat ctgattactt atgtgtggca ggctaatgac aatgttaccc gtgtaagttc    600
caagtttggt gcatcacaag tggatatgtt tactgaaaac aatcaaaact tcactgcttc    660
aaccaatgtt ccgattttga tccctgtgac aaagttaccg gtaattgatc aaccatcttc    720
aaatggaaga aaaaacagca ctcaaaaacc tgcttttata attggtatta gcctaggatg    780
tgcttttttc gttgtagttt taacactatc acttgtttat gtatattgtc tgaaaatgaa    840
gagattgaat aggagtactt cattggcgga gactgcggat aagttacttt caggtgtttc    900
gggttatgta agcaagccaa caatgtatga atggatgcg atcatggaag ctacaatgaa     960
cctgagtgag aattgtaaga ttggtgaatc tgtttacaag gctaatatag atggtagagt   1020
tttagcagtg aaaaaaatca agaaagatgc ttctgaggag ctgaaaattc tgcagaaggt   1080
aaatcatgga aatcttgtga aacttatggg tgtgtcttcc gacaacgaag gaaactgttt   1140
ccttgtttac gagtatgctg aaaatggatc acttgatgag tggttgttct cagagttgtc    1200
gaaaacttcg aactcggtgg tctcgcttac atggtctcag agaataacag tagcagtgga    1260
```

-continued

```
tgttgcagtt ggtttgcaat acatgcatga acatacttac ccaagaataa tccacagaga   1320
catcacaaca agtaatatcc ttctggattc aaactttaag gccaagatag cgaattttc    1380 aatggccaga acttcaacaa attccatgat gccgaaaatc gatgttttcg cttttgggt    1440 ggttctgatt gagttgctta ccggcaagaa agcgataaca acgatggaaa atggcgaggt   1500
ggttattctg tggaaggatt tctgaagat ttttgatcta aagggaata gagaagagag     1560 cttaagaaaa tggatggatc ctaagctaga gaatttttat cctattgata atgctcttag   1620
tttggcttct ttggcagtga attgtactgc agataaatca ttgtcaagac caagcattgc   1680
agaaattgtt ctttgtcttt ctcttctcaa tcaatcatca tctgaaccaa tgttagaaag   1740
atccttgaca tctggtttag atgttgaagc tactcatgtt gttacttcta tagtagctcg   1800
ttgatattca ttcaagtgaa ggtaacacta aatcaatgct tcagtttctt atattcaaga   1860
tggttacttt gtttaggtga ttattgatta catctttatg tgtggaacta tatggttatt   1920
ttaattaagg gaattagt                                                  1938
```

<210> SEQ ID NO 15
<211> LENGTH: 594
<212> TYPE: PRT
<213> ORGANISM: Pisum sativum

<400> SEQUENCE: 15

```
Met Ala Ile Phe Phe Leu Pro Ser Ser His Ala Leu Phe Leu Ala
1               5                   10                  15

Leu Met Phe Phe Val Thr Asn Ile Ser Ala Gln Pro Leu Gln Leu Ser
                20                  25                  30

Gly Thr Asn Phe Ser Cys Pro Val Asp Ser Pro Ser Cys Glu Thr
            35                  40                  45

Tyr Val Thr Tyr Phe Ala Arg Ser Pro Asn Phe Leu Ser Leu Thr Asn
        50                  55                  60

Ile Ser Asp Ile Phe Asp Met Ser Pro Leu Ser Ile Ala Lys Ala Ser
65                  70                  75                  80

Asn Ile Glu Asp Glu Asp Lys Lys Leu Val Glu Gly Gln Val Leu Leu
                85                  90                  95

Ile Pro Val Thr Cys Gly Cys Thr Arg Asn Arg Tyr Phe Ala Asn Phe
            100                 105                 110

Thr Tyr Thr Ile Lys Leu Gly Asp Asn Tyr Phe Ile Val Ser Thr Thr
        115                 120                 125

Ser Tyr Gln Asn Leu Thr Asn Tyr Val Glu Met Glu Asn Phe Asn Pro
    130                 135                 140

Asn Leu Ser Pro Asn Leu Leu Pro Pro Glu Ile Lys Val Val Pro
145                 150                 155                 160

Leu Phe Cys Lys Cys Pro Ser Lys Asn Gln Leu Ser Lys Gly Ile Lys
                165                 170                 175

His Leu Ile Thr Tyr Val Trp Gln Ala Asn Asp Asn Val Thr Arg Val
            180                 185                 190

Ser Ser Lys Phe Gly Ala Ser Gln Val Asp Met Phe Thr Glu Asn Asn
        195                 200                 205

Gln Asn Phe Thr Ala Ser Thr Asn Val Pro Ile Leu Ile Pro Val Thr
    210                 215                 220

Lys Leu Pro Val Ile Asp Gln Pro Ser Ser Asn Gly Arg Lys Asn Ser
225                 230                 235                 240

Thr Gln Lys Pro Ala Phe Ile Ile Gly Ile Ser Leu Gly Cys Ala Phe
                245                 250                 255
```

Phe Val Val Leu Thr Leu Ser Leu Val Tyr Val Tyr Cys Leu Lys
             260                 265                 270

Met Lys Arg Leu Asn Arg Ser Thr Ser Leu Ala Glu Thr Ala Asp Lys
275                 280                 285

Leu Leu Ser Gly Val Ser Gly Tyr Val Ser Lys Pro Thr Met Tyr Glu
            290                 295                 300

Met Asp Ala Ile Met Glu Ala Thr Met Asn Leu Ser Glu Asn Cys Lys
305                 310                 315                 320

Ile Gly Glu Ser Val Tyr Lys Ala Asn Ile Asp Gly Arg Val Leu Ala
                325                 330                 335

Val Lys Lys Ile Lys Lys Asp Ala Ser Glu Glu Leu Lys Ile Leu Gln
                340                 345                 350

Lys Val Asn His Gly Asn Leu Val Lys Leu Met Gly Val Ser Ser Asp
            355                 360                 365

Asn Asp Gly Asn Cys Phe Leu Val Tyr Glu Tyr Ala Glu Asn Gly Ser
        370                 375                 380

Leu Asp Glu Trp Leu Phe Ser Glu Ser Ser Lys Thr Ser Asn Ser Val
385                 390                 395                 400

Val Ser Leu Thr Trp Ser Gln Arg Ile Thr Val Ala Val Asp Val Ala
                405                 410                 415

Val Gly Leu Gln Tyr Met His Glu His Thr Tyr Pro Arg Ile Ile His
            420                 425                 430

Arg Asp Ile Thr Thr Ser Asn Ile Leu Leu Asp Ser Asn Phe Lys Ala
        435                 440                 445

Lys Ile Ala Asn Phe Ser Met Ala Arg Thr Ser Thr Asn Ser Met Met
450                 455                 460

Pro Lys Ile Asp Val Phe Ala Phe Gly Val Val Leu Ile Glu Leu Leu
465                 470                 475                 480

Thr Gly Lys Lys Ala Ile Thr Thr Met Glu Asn Gly Glu Val Val Ile
                485                 490                 495

Leu Trp Lys Asp Phe Trp Lys Ile Phe Asp Leu Glu Gly Asn Arg Glu
                500                 505                 510

Glu Ser Leu Arg Lys Trp Met Asp Pro Lys Leu Glu Asn Phe Tyr Pro
            515                 520                 525

Ile Asp Asn Ala Leu Ser Leu Ala Ser Leu Ala Val Asn Cys Thr Ala
        530                 535                 540

Asp Lys Ser Leu Ser Arg Pro Ser Ile Ala Glu Ile Val Leu Cys Leu
545                 550                 555                 560

Ser Leu Leu Asn Gln Ser Ser Ser Glu Pro Met Leu Glu Arg Ser Leu
                565                 570                 575

Thr Ser Gly Leu Asp Val Glu Ala Thr His Val Val Thr Ser Ile Val
            580                 585                 590

Ala Arg

<210> SEQ ID NO 16
<211> LENGTH: 19
<212> TYPE: DNA
<213> ORGANISM: Lotus japonicus

<400> SEQUENCE: 16
tgcatttgca tggagaacc                                          19

<210> SEQ ID NO 17
<211> LENGTH: 20
<212> TYPE: DNA

<213> ORGANISM: Lotus japonicus

<400> SEQUENCE: 17
tttgctgtga cattatcagc                                               20

<210> SEQ ID NO 18
<211> LENGTH: 20
<212> TYPE: DNA
<213> ORGANISM: Lotus japonicus

<400> SEQUENCE: 18
ttgcagattg cacaactagg                                               20

<210> SEQ ID NO 19
<211> LENGTH: 21
<212> TYPE: DNA
<213> ORGANISM: Lotus japonicus

<400> SEQUENCE: 19
acttagaatc tgcaactttg c                                             21

<210> SEQ ID NO 20
<211> LENGTH: 21
<212> TYPE: DNA
<213> ORGANISM: Lotus japonicus

<400> SEQUENCE: 20
acttagaatc tgcaactttg c                                             21

<210> SEQ ID NO 21
<211> LENGTH: 2205
<212> TYPE: DNA
<213> ORGANISM: Lotus japonicus

<400> SEQUENCE: 21
aagtgtgaca ttagtttcaa gagaaaaata aatgatcaaa acctggtaga gagtcctaga    60
aattcaatgt tctgatttct ttcattcatc tctgctgcca ttttgatttg cacaatgaag   120
ctaaaaactg gtctactttt gtttttcatt cttttgctgg ggcatgtttg tttccatgtg   180
gaatcaaact gtctgaaggg gtgtgatcta gctttagctt cctattatat cttgcctggt   240
gttttcatct tacaaaacat aacaaccttt atgcaatcag agattgtctc aagtaatgat   300
gccataacca gctacaacaa agacaaaatt ctcaatgata tcaacatcca atcctttcaa   360
agactcaaca ttccatttcc atgtgactgt attggtggtg agtttctagg gcatgtattt   420
gagtactcag cttcaaaagg agacacttat gaaactattg ccaacctcta ctatgcaaat   480
ttgacaacag ttgatctttt gaaaaggttc aacagctatg atccaaaaaa catacctgtt   540
aatgccaagg ttaatgtcac tgttaattgt tcttgtggga acagccaggt tcaaaagat   600 tatgcttgt ttattaccta tcccattagg cctggggata cactgcagga tattgcaaac   660
cagagtagtc ttgatgcagg gttgatacag agtttcaacc caagtgtcaa tttcagcaaa   720
gatagtggga tagcttttcat tcctggaaga tataaaaatg gagtctatgt tcccttgtac   780
cacagaaccg caggtctagc tagtggtgca gctgttggta tatctattgc aggaaccttc   840
gtgcttctgt tactagcatt ttgtatgtat gttagatacc agaagaagga agaagagaaa   900
gctaaattgc caacagatat ttctatggcc ctttcaacac aagatgcctc tagtagtgca   960
gaatatgaaa cttctggatc cagtgggcca gggactgcta gtgctacagg tcttactagc  1020
attatggtgg cgaaatcaat ggagttctca tatcaggaac tagcgaaggc tacaaataac  1080

```
tttagcttgg ataataaaat tggtcaaggt ggatttggag ctgtctatta tgcagaattg    1140
agaggcaaga aaacagcaat taagaagatg gatgtacaag catcaacaga atttctttgt    1200
gagttgaagg tcttaacaca tgttcaccac ttgaatctgg tgcgcttgat tggatactgc    1260
gttgagggat ctctattcct tgtttatgaa catattgaca atggaaactt aggccaatat    1320
ttgcatggtt caggtaaaga accattgcca tggtctagcc gagtacaaat agctctagat    1380
gcagcaagag gccttgaata cattcatgag cacactgtgc ctgtgtatat ccatcgcgat    1440
gtgaaatctg caaacatatt gatagataag aacttgcgtg gaaaggttgc agattttggc    1500
ttgaccaagc ttattgaagt tgggaactcc acactacaaa ctcgtctggt gggaacattt    1560
ggatacatgc ccccagaata tgctcaatat ggtgatattt ctccaaaaat agatgtatat    1620
gcatttggag ttgttctttt tgaacttatt tctgcaaaga atgctgttct gaagacaggt    1680
gaattagttg ctgaatcaaa gggccttgta gctttgtttg aagaagcact taataagagt    1740
gatccttgtg atgctcttcg caaactggtg gatcctaggc ttggagaaaa ctatccaatt    1800
gattctgttc tcaagattgc acaactaggg agagcttgta caagagataa tccactgcta    1860
agaccaagta tgagatcttt agttgttgct cttatgaccc tttcatcact tactgaggat    1920
tgtgatgatg aatcttccta cgaaagtcaa actctcataa atttactgtc tgtgagataa    1980
aggttctcca tgcaaatgca tgtttgttat atatatcttg tagtacaact aagcagacaa    2040
aaagttttgt actttgaatg taaatcgagt cagggtgttt acattttatt actccaatgt    2100
ttaattgcca aaaccatcaa aaagtcctag gccagacttc ctgtaattat atttagcaaa    2160
gttgcagatt ctaagttcag tttttttaaa aaaaaaaaa aaaaa              2205
```

<210> SEQ ID NO 22
<211> LENGTH: 2210
<212> TYPE: DNA
<213> ORGANISM: Lotus japonicus

<400> SEQUENCE: 22

```
aagtgtgaca ttagtttcaa gagaaaaata aatgatcaaa acctggtaga gagtcctaga      60
aattcaatgt tctgatttct ttcattcatc tctgctgcca ttttgatttg cacaatgaag     120
ctaaaaactg gtctactttt gttttttcatt cttttgctgg ggcatgtttg tttccatgtg     180
gaatcaaact gtctgaaggg gtgtgatcta gctttagctt cctattatat cttgcctggt     240
gttttcatct tacaaaacat aacaaccttt atgcaatcag agattgtctc aagtaatgat     300
gccataacca gctacaacaa agacaaaatt ctcaatgata tcaacatcca atcctttcaa     360
agactcaaca ttccatttcc atgtgactgt attggtggtg agtttctagg gcatgtattt     420
gagtactcag cttcaaaagg agacacttat gaaactattg ccaacctcta ctatgcaaat     480
ttgacaacag ttgatctttt gaaaaggttc aacagctatg atccaaaaaa catacctgtt     540
aatgccaagg ttaatgtcac tgttaattgt tcttgtggga acagccaggt ttcaaaagat     600
tatggcttgt ttattaccta tcccattagg cctggggata cactgcagga tattgcaaac     660
cagagtagtc ttgatgcagg gttgatacag agtttcaacc caagtgtcaa tttcagcaaa     720
gatagtggga tagctttcat tcctggaaga tataaaaatg gagtctatgt tcccttgtac     780
cacagaaccg caggtctagc tagtggtgca gctgttggta tatctattgc aggaaccttc     840
gtgcttctgt tactagcatt ttgtatgtat gttagatacc agaagaagga agaagagaaa     900
gctaaattgc caacagatat ttctatggcc ctttcaacac aagatggtaa tgcctctagt     960
agtgcagaat atgaaacttc tggatccagt gggccaggga ctgctagtgc tacaggtctt    1020
```

```
actagcatta tggtggcgaa atcaatggag ttctcatatc aggaactagc gaaggctaca    1080 aataactttta gcttggataa taaaattggt caaggtggat ttggagctgt ctattatgca   1140
gaattgagag gcaagaaaac agcaattaag aagatggatg tacaagcatc aacagaattt   1200
ctttgtgagt tgaaggtctt aacacatgtt caccacttga atctggtgcg cttgattgga   1260
tactgcgttg agggatctct attccttgtt tatgaacata ttgacaatgg aaacttaggc   1320
caatatttgc atggttcagg taaagaacca ttgccatggt ctagccgagt acaaatagct   1380
ctagatgcag caagaggcct tgaatacatt catgagcaca ctgtgcctgt gtatatccat   1440
cgcgatgtga atctgcaaa catattgata gataagaact gcgtggaaa ggttgcagat    1500 tttggcttga ccaagcttat tgaagttggg aactccacac tacaaactcg tctggtggga   1560
acatttggat acatgccccc agaatatgct caatatggtg atatttctcc aaaaatagat   1620
gtatatgcat ttggagttgt tcttttgaa cttatttctg caaagaatgc tgttctgaag    1680
acaggtgaat tagttgctga atcaaagggc cttgtagctt tgtttgaaga agcacttaat   1740
aagagtgatc cttgtgatgc tcttcgcaaa ctggtggatc ctaggcttgg agaaaactat   1800
ccaattgatt ctgttctcaa gattgcacaa ctagggagag cttgtacaag agataatcca   1860
ctgctaagac caagtatgag atctttagtt gttgctctta tgacccttc atcacttact    1920 gaggattgtg atgatgaatc ttcctacgaa agtcaaactc tcataaattt actgtctgtg   1980
agataaaggt tctccatgca aatgcatgtt tgttatatat atcttgtagt acaactaagc   2040
agacaaaaag ttttgtactt tgaatgtaaa tcgagtcagg gtgtttacat tttattactc    2100
caatgtttaa ttgccaaaac catcaaaaag tcctaggcca gacttcctgt aattatattt   2160
agcaaagttg cagattctaa gttcagtttt tttaaaaaaa aaaaaaaaa               2210
```

```
<210> SEQ ID NO 23
<211> LENGTH: 10253
<212> TYPE: DNA
<213> ORGANISM: Lotus japonicus Gifu
<220> FEATURE:
<221> NAME/KEY: exon
<222> LOCATION: (4172)..(4808)
<220> FEATURE:
<221> NAME/KEY: Intron
<222> LOCATION: (4809)..(5280)
<220> FEATURE:
<221> NAME/KEY: exon
<222> LOCATION: (5281)..(5314)
<220> FEATURE:
<221> NAME/KEY: Intron
<222> LOCATION: (5315)..(5561)
<220> FEATURE:
<221> NAME/KEY: exon
<222> LOCATION: (5562)..(5569)
<220> FEATURE:
<221> NAME/KEY: Intron
<222> LOCATION: (5570)..(5685)
<220> FEATURE:
<221> NAME/KEY: exon
<222> LOCATION: (5686)..(5838)
<220> FEATURE:
<221> NAME/KEY: Intron
<222> LOCATION: (5839)..(6475)
<220> FEATURE:
<221> NAME/KEY: exon
<222> LOCATION: (6476)..(6678)
<220> FEATURE:
<221> NAME/KEY: Intron
<222> LOCATION: (6679)..(7105)
<220> FEATURE:
<221> NAME/KEY: exon
<222> LOCATION: (7106)..(7195)
<220> FEATURE:
<221> NAME/KEY: Intron
```

```
<222> LOCATION: (7196)..(7933)
<220> FEATURE:
<221> NAME/KEY: exon
<222> LOCATION: (7934)..(8027)
<220> FEATURE:
<221> NAME/KEY: Intron
<222> LOCATION: (8028)..(8232)
<220> FEATURE:
<221> NAME/KEY: exon
<222> LOCATION: (8233)..(8384)
<220> FEATURE:
<221> NAME/KEY: Intron
<222> LOCATION: (8385)..(8471)
<220> FEATURE:
<221> NAME/KEY: exon
<222> LOCATION: (8472)..(8563)
<220> FEATURE:
<221> NAME/KEY: Intron
<222> LOCATION: (8564)..(9137)
<220> FEATURE:
<221> NAME/KEY: exon
<222> LOCATION: (9138)..(9275)
<220> FEATURE:
<221> NAME/KEY: Intron
<222> LOCATION: (9276)..(9403)
<220> FEATURE:
<221> NAME/KEY: exon
<222> LOCATION: (9404)..(9502)
<220> FEATURE:
<221> NAME/KEY: Intron
<222> LOCATION: (9503)..(9694)
<220> FEATURE:
<221> NAME/KEY: exon
<222> LOCATION: (9695)..(9859)

<400> SEQUENCE: 23
gcatgcatat agctctattt ctttagtaat gttacacctg cacgatgtgc ataataatag       60
aagacataat acatatacag attaaaatta aataaacaat ttctaatcaa atttaaaaat      120
gtcaacttaa tttcattatt aaaatataac aatatgaata accaaaaata aattaagaca      180 ttcaccccccc cccccccgaa aagaaattta agacaattac aatttttttgg tatatatatt    240 aaagacttcc aattatggac ataggatctc aacttagtaa tcttcacttt aggaaagtct      300
tttccccaca agtcacaacc atctattaat atcaatacaa aatgaagaca actcaataaa      360
aagatccttt tataggaaat tgatgaataa aactgatata tatttcagtt aaaattgttc      420
aaacattagt gcaatggaca gaagtatcct ttgtgccctc atttgccaac aactggctca      480
tcaagcaata aattaattcg ccatttccaa acttttgcag ttttaagtag aagatatcca      540
ttcgttgaaa ctttcttcac accaccaatt tcctcctaaa tgggttaaca aatgtgcaat      600
gatcgaaata tatagttgaa acgatcaaga tcctctcaat ggtaaaagaa tttgaccacg      660
ctaagtttta ttatctcact agctattaat ttaattatca tttatctttt caattattaa      720
acacacaaat aatcaatcct aaaatgatga aacttgacat ggtctatttt tacaataact      780
taaccaaaaa cttataagtt agcaactttc aaaaacaggt tttcccttgt taagaataga      840
caaatcaaat ggagtgtgtt aaatattgtg tttaaaatag tgtgttgcaa gcatttctct      900
tataaaaaat cagtataaat atgtttggaa ctgtttatttt tagtttatct tatattataa     960
atacaaaaca agtgtttggt aaagctaatg aaaataactt aaaacatacc tatggtttgt     1020
cggatgtgtc gcgggtggag ctccttgcca ttttgtgtgg cctttgtatg tgttgagata     1080
tggccatggg ttattgtaga atccttcttc ttttggattc ttctttgttc ctgtctctca     1140
ttcaacgctc atgttaccca tttcatccat gccaagtttt tttatacat gcatctaaat      1200 tttttccgcc atatcttaat tttgttttta ttaaaattaa aaagaatatg attgaatgtc     1260
aatgtaaatt ttttttacac agacaatgca tatccattaa ggtttgttag aattacactc    1320
```

```
caccccattt ttatctaaaa tctacatccc accccatttt atatagaggc aaatttagtg    1380
acgaaaaata ttcttcatta ataattagtt attatttaaa ttgttaatca ataatttcaa    1440
aaaaaaattc aatataatcc aataaattta aaaatgaaaa catcacaatc ctcctcattc    1500
tctcaatcgc gttttacctc cgtaaattta caatgcaaat tatgcaatag cacacctgcc    1560
cgatttacaa accatatttc gaacatagtg aaacatgctt gtgttttcat atttggtgat    1620
aattcaattt taatcaaaat aatctcttta tacctccaat tttcaaaatt gggttgtagg    1680
ccaaaaaagc aacacaaatg ggtgaagaaa atagagaaac aaaattatga aaatatgaag    1740
tggatctgag gttattagag cccaacgagg cggtggagca tcgttttttaa caaaatccaa    1800 caatatcttt aggggtgaaa tccaccaacc gagcgttcgc tcacaactta aggggtgaa    1860 attcacaaga gtagtttaa aggggtgaaa ttcacaagaa gtagttgaac aagtgacttt    1920
aggaatgtgc gattcacgtt ctggggttca ggtcgcaaca aaactttgag gcatggtggt    1980
gccatgtggt ttcacattgt gggacagtgg agccgtgtta aagggagtaa aggcttggtg    2040
gtggccgttt gtggtgaaaa atatgatttg gagatagatg ggacgtggac ttaacagaca    2100
gagtggatgt ttttttttta aatttaattc agtaaaatta tttttataaa ttaatgtatg    2160
atagtgtata tgcattaaat ttatttaaat ttttactaat tagtaatttg tttttagtag    2220
tgacgaattt gttttgtca ctaaattttg cctttataaa aaatgggtg gagtgtagat    2280 ttttaaaaag aatggggtgg agtgtcattc ttgcaaatct tgagggggt gagtgtattt    2340 tactcaactc ttaaaaaat taggaattaa ttagttgtaa attataaaag tttatttcat    2400
tgaataacat aacaaattaa aggcaaaaaa atacaaaact tcattttata tgtatttcag    2460
aaaaattgcc tactttcaat tatgagaaac taaaattatg tttagtttaa aatgagcata    2520
gattcaaaaa ttaataaata atatatatag caggatacat gcctatcaat taacatatcg    2580
tttgtccacg atgatgatct tattggagga tcaatatctt caaattaaca aagttatcac    2640
ttggctctta ttggtcataa tgcaataaaa aaattgcaat tagtatcaaa tcaaactgaa    2700
atttgcaact atatgctgct ggtgttgtcg cgcagattcc ttttttgattt ttatgggaat    2760 gaagtcaatg aagcaacagt ttcacaggcg tgcttaaaaa taaaaaaatt ggaaatttga    2820
tgtttgttag gattatgaga ggacacaatg ggaggatgtt tcacaagctg cagacagggt    2880
tgccacttca gatgcaaagg attaaataaa caaagccaag gtttgcaatc aacaagattc    2940
catcgtcgtt ttgcttcctt taatcgtatt aatcaaaagc acaccaagta aagcatcaat    3000
atataacatc caagaaatca caacatgata gttgctcgtc tcgtctatta actatgatgt    3060
caggagttcg atccccgctc atgtgaatgg aagacatttc gttgttagat gtttaccgtt    3120
taatgcaaat actcgcggtg agataataag tcattgttgt gggcgaatac cctaaaataa    3180
gaataaaatt aaatatagca tccaagttat tgcccaaata tataaacaat ggtattgttg    3240
acattattag gcataaaagc agtaggtaag tgtattatat ttatttaatt ttttaaaatt    3300
ttgaaattaa ttaataattg ttaacataag taaaccattt ttagcaaaaa ctctacactt    3360
ctattacctt aacaagtaca tttttgatgg tacaccttaa caattaacaa gtcatatgat    3420
tgacaaacat attttatatg ctttacaatt tattctaaaa tcaagtttta tgggaagaag    3480
ctcataaaag tagttcctgg gtgtttttta gaatagagaa gttgatcatg ttagaaatta    3540
agttaaaaat gagttgaaag tgatttatgt ttgattatat ttatgagaaa aatgaattgt    3600
ctgatgtaat attgtaaaat ctaacaatta attaagtacc acagaaacta gaatttatag    3660
cttcacctta gaattgattt tggagttaaa atcaattatt aaaggagcaa ttattaaagg    3720
```

```
agacatccaa atacactagt taattttgac aatcaattct aacacttgca aatgtgtaac      3780
caaacttact atcagtaagt gaactaatga ttcccaagtc aacttttgtt ctagctagcc      3840
aaccgttact atgttccctc cacaatacat tctccttgaa actgtcaagt gtcaactgca      3900
cccaaacatc cttgtttgtg atgaaaagat cgaaaacgtg tgcttatgaa tttacatgtt      3960
tacattcacc aaaaatcaaa agttacacct ctatacttat cacatatgtt tgagtcactt      4020
tccatataaa atcccatagt ctattaatta tcagagtaag tgtgacatta gtttcaagag      4080
aaaaataaat gatcaaaacc tggtagagag tcctagaaat tcaatgttct gatttctttc      4140
attcatctct gctgccattt tgatttgcac a atg aag cta aaa act ggt cta         4192
                                   Met Lys Leu Lys Thr Gly Leu
                                    1               5 ctt ttg ttt ttc att ctt ttg ctg ggg cat gtt tgt ttc cat gtg gaa        4240
Leu Leu Phe Phe Ile Leu Leu Leu Gly His Val Cys Phe His Val Glu
        10                  15                  20 tca aac tgt ctg aag ggg tgt gat cta gct tta gct tcc tat tat atc        4288
Ser Asn Cys Leu Lys Gly Cys Asp Leu Ala Leu Ala Ser Tyr Tyr Ile
 25                  30                  35 ttg cct ggt gtt ttc atc tta caa aac ata aca acc ttt atg caa tca        4336
Leu Pro Gly Val Phe Ile Leu Gln Asn Ile Thr Thr Phe Met Gln Ser
40                  45                  50                  55 gag att gtc tca agt aat gat gcc ata acc agc tac aac aaa gac aaa        4384
Glu Ile Val Ser Ser Asn Asp Ala Ile Thr Ser Tyr Asn Lys Asp Lys
                60                  65                  70 att ctc aat gat atc aac atc caa tcc ttt caa aga ctc aac att cca        4432
Ile Leu Asn Asp Ile Asn Ile Gln Ser Phe Gln Arg Leu Asn Ile Pro
            75                  80                  85 ttt cca tgt gac tgt att ggt ggt gag ttt cta ggg cat gta ttt gag        4480
Phe Pro Cys Asp Cys Ile Gly Gly Glu Phe Leu Gly His Val Phe Glu
        90                  95                 100 tac tca gct tca aaa gga gac act tat gaa act att gcc aac ctc tac        4528
Tyr Ser Ala Ser Lys Gly Asp Thr Tyr Glu Thr Ile Ala Asn Leu Tyr
105                 110                 115 tat gca aat ttg aca aca gtt gat ctt ttg aaa agg ttc aac agc tat        4576
Tyr Ala Asn Leu Thr Thr Val Asp Leu Leu Lys Arg Phe Asn Ser Tyr
120                 125                 130                 135 gat cca aaa aac ata cct gtt aat gcc aag gtt aat gtc act gtt aat        4624
Asp Pro Lys Asn Ile Pro Val Asn Ala Lys Val Asn Val Thr Val Asn
                140                 145                 150 tgt tct tgt ggg aac agc cag gtt tca aaa gat tat ggc ttg ttt att        4672
Cys Ser Cys Gly Asn Ser Gln Val Ser Lys Asp Tyr Gly Leu Phe Ile
            155                 160                 165 acc tat ccc att agg cct ggg gat aca ctg cag gat att gca aac cag        4720
Thr Tyr Pro Ile Arg Pro Gly Asp Thr Leu Gln Asp Ile Ala Asn Gln
        170                 175                 180 agt agt ctt gat gca ggg ttg ata cag agt ttc aac cca agt gtc aat        4768
Ser Ser Leu Asp Ala Gly Leu Ile Gln Ser Phe Asn Pro Ser Val Asn
185                 190                 195 ttc agc aaa gat agt ggg ata gct ttc att cct gga aga t gtatgttatc       4818
Phe Ser Lys Asp Ser Gly Ile Ala Phe Ile Pro Gly Arg
200                 205                 210 cttttgtttt taaattttc cgctttgatt aaagtttatt attattagca tgattggatc       4878
aacttctctt tcatcaaaat catttctgaa actcagaagc tactcacaca agcttcctgg      4938
tttcagaatc aattgtagta gggttttcaa acatgctctt ttatcaaaat caattacgta      4998
actcagaaac tactcacata agcttctcct tagaattgat tctgttttta gaatcaattg      5058
taaaagggtt tacaaacatg cactctgcta gtgtgtgtgc ttaaaactat tcatggtgaa      5118
```

```
                                            -continued attactcttc cattgtttct acaataatac atgacaaggc atgtaactta ccccacctaa    5178
ttgaaaaatg gttggtggtt attgttatat catttgttca atacatttga tataaacttt    5238
tatgaattta cctgaagttt tactttcctt tgaactttc ag at  aaa aat gga        5291
                                             Tyr Lys Asn Gly
                                                     215 gtc tat gtt ccc ttg tac cac ag  gtgggtaact tcaattgcct actcatcttt    5344
Val Tyr Val Pro Leu Tyr His Arg
                    220 ttatgatgaa tgatagcatg tttggatcaa cttctctttc accagaatta atccttaaat    5404 tcagaactaa gaagctactc acataagctt tttcccggaa ttaattctgg cttcagaagc    5464 aattacactg aaagatttcc aaacatgctc taaatattgt ttcgtgcttg gttctatctt    5524 tttaactttc atttatttt cctttttcat tttgcag a acc gca g gtttggccct      5579
                                         Thr Ala
                                             225 ctaaattggt tctagggatg attattttta ccttgatgtt cacaaaaata tgagaacaca    5639 aaaaaagagg atgcctctga gcttagcttt acttctatgt aagcag gt  cta gct      5693
                                                      Gly Leu Ala agt ggt gca gct gtt ggt ata tct att gca gga acc ttc gtg ctt ctg    5741
Ser Gly Ala Ala Val Gly Ile Ser Ile Ala Gly Thr Phe Val Leu Leu
230                 235                 240                 245 tta cta gca ttt tgt atg tat gtt aga tac cag aag aag gaa gaa gag    5789
Leu Leu Ala Phe Cys Met Tyr Val Arg Tyr Gln Lys Lys Glu Glu Glu
                250                 255                 260 aaa gct aaa ttg cca aca gat att tct atg gcc ctt tca aca caa gat g  5838
Lys Ala Lys Leu Pro Thr Asp Ile Ser Met Ala Leu Ser Thr Gln Asp
                265                 270                 275 gtaatggtat atttccaaat tcatattcct tctaagttct aaccctcttt agtcccccctg   5898 gaaatgggtg aatgttggtg ctctaatttt tcatgtgttt aaatcagttt tatactaaga    5958
gtctgttgga caacaggttt tgttttaa acagaaaaa gccgaaaatt tgtttgatat      6018
gaaaagtttt aaggaaattc ttatttttt gatatatcgg aaaattctta ttaagtgttc    6078
ctgttctcat tttctaaaac taaaatttca aaacatctcg gaggattttt cttcttgttt    6138
ttagttttca attcacaggt ctttcagttt tgtaagcatc ttgttcaaat atagattttc    6198
ttttcttctt ttgaaaaaca tgtcataaaa ttatttctga aaatagtttt taaatttaga    6258
ggactgagaa gagaatcaaa caagtcctaa ttttttacctt ttcctgttta tcatttataa   6318
acttattacc tgatctaatt tcaggctaca ttttacctga tgttaaaggc agaaaattta    6378
cctgatccaa atgtttgagt tccattcaat ctggcacatt gatataattt gagaggatat    6438
gacaacacta gctaactttt cttcctcttt cttgaag cc  tct agt agt gca gaa    6492
                                             Ala Ser Ser Ser Ala Glu
                                                                280 tat gaa act tct gga tcc agt ggg cca ggg act gct agt gct aca ggt    6540
Tyr Glu Thr Ser Gly Ser Ser Gly Pro Gly Thr Ala Ser Ala Thr Gly
            285                 290                 295 ctt act agc att atg gtg gcg aaa tca atg gag ttc tca tat cag gaa    6588
Leu Thr Ser Ile Met Val Ala Lys Ser Met Glu Phe Ser Tyr Gln Glu
300                 305                 310                 315 cta gcg aag gct aca aat aac ttt agc ttg gat aat aaa att ggt caa    6636
Leu Ala Lys Ala Thr Asn Asn Phe Ser Leu Asp Asn Lys Ile Gly Gln
                320                 325                 330 ggt gga ttt gga gct gtc tat tat gca gaa ttg aga ggc aag            6678
Gly Gly Phe Gly Ala Val Tyr Tyr Ala Glu Leu Arg Gly Lys
            335                 340                 345
```

```
gtagtgaccg tgtgtctctt cagttctata acatagtgca tgtttggata caaagaggaa    6738
aaccacggtg aagccaaatt tgcggtggac agacacaaaa gctaaaggaa gttgtcacca    6798
tgattttcaa ttgtgtatcc aaacttgcac aaaagaggat agaagtttct tacattagag    6858
tagtagtgaa aagtttaaat tttaaggctt tgtgttcatt gtgaggaagc tatataaaac    6918
aactcaaatc agtttagggc aaaaaattgt tcattgaaaa agaaagataa gagtaatgat    6978
tttacttaaa tggatattgt tcttaaagag gtggatggga aagtttctgc tttttgtgcc    7038
actttaggtt atcccttttaa cttttaactc ttcctggatt tcctctaatg caatttattc    7098 aatgcag aaa aca gca att aag aag atg gat gta caa gca tca aca gaa    7147
        Lys Thr Ala Ile Lys Lys Met Asp Val Gln Ala Ser Thr Glu
            350                 355 ttt ctt tgt gag ttg aag gtc tta aca cat gtt cac cac ttg aat ctg    7195
Phe Leu Cys Glu Leu Lys Val Leu Thr His Val His His Leu Asn Leu
360                 365                 370                 375 gtacaacatc cttcaaacaa cttaaagcat tattatatct ttgggaagga agattaata     7255 tttttatgtt tagtttgaag aatcattagg ttcttacaaa acaaatatcc ttcatggttc    7315
tgtgaactga atagtcctat agttatccag caaaatttct gcagatccac atgatagtcc    7375
aacatgggat ctgcattact agtgaaagaa cttgtaaaac atttgtaact tcaattttct    7435
gtccttgaaa gtaacagacc atttagagca cactccccaa cattaatacc aaataaagaa    7495
gaaaatcagc cctcttcccg catgtgtggt tccactgtga atatttgaa atcacttgt      7555 gattagaagc tacaagtcta agcttctgag caaacgtgtc ttggattttg tgctaatcat    7615
aaagccaaat atgctattag ttaatgatta aaggcattat tagaaactcc tttatttcca    7675
attgccactg ttgatatgtt atttggattt tcaaacagt ttctcctaac aaacaggttc     7735
agaaaaaaaa ttagtattaa tttctatcta tgattactta aagaagaaag tgctaaattc    7795
tttctgggat ttcaatataa ctatatcata cacttttcat ttaatttttc taattttgga   7855
atctttgttt agcataaaca gctctaagta agttataatt cttattctgt atgtacctac    7915
tttctatgaa caacatag gtg cgc ttg att gga tac tgc gtt gag gga tct    7966
                    Val Arg Leu Ile Gly Tyr Cys Val Glu Gly Ser
                                380                 385 cta ttc ctt gtt tat gaa cat att gac aat gga aac tta ggc caa tat    8014
Leu Phe Leu Val Tyr Glu His Ile Asp Asn Gly Asn Leu Gly Gln Tyr
390                 395                 400 ttg cat ggt tca g gtgagaacag gatgcagtga tattttttg ctgtgacatt        8067
Leu His Gly Ser
        405 atcagcatgt ttggatcaat ttctctttca ccagaattaa ttctgaaaca gagaagtagc    8127 ttctccacaa aattgattct gacttcagag tcaatagtag aattatttcg aaacatgcac    8187 ggcattatag tcaaacaatt aataatgatg atgacatgat ttcag gt  aaa gaa cca   8243
                                                     Gly Lys Glu Pro
                                                                 410 ttg cca tgg tct agc cga gta caa ata gct cta gat gca gca aga ggc    8291
Leu Pro Trp Ser Ser Arg Val Gln Ile Ala Leu Asp Ala Ala Arg Gly
            415                 420                 425 ctt gaa tac att cat gag cac act gtg cct gtg tat atc cat cgc gat    8339
Leu Glu Tyr Ile His Glu His Thr Val Pro Val Tyr Ile His Arg Asp
            430                 435                 440 gtg aaa tct gca aac ata ttg ata gat aag aac ttg cgt gga aag         8384
Val Lys Ser Ala Asn Ile Leu Ile Asp Lys Asn Leu Arg Gly Lys
        445                 450                 455 gttgcattta ttaccaatct tcatgatcca aattctttca tttcttcttt gagactttaa    8444
```

-continued

```
tcaaactgtg aaagttttta tgttcag gtt gca gat ttt ggc ttg acc aag ctt       8498
                                Val Ala Asp Phe Gly Leu Thr Lys Leu
                                460                 465 att gaa gtt ggg aac tcc aca cta caa act cgt ctg gtg gga aca ttt         8546
Ile Glu Val Gly Asn Ser Thr Leu Gln Thr Arg Leu Val Gly Thr Phe
        470                 475                 480 gga tac atg ccc cca ga gtatgattttt cttttgatgt tgtattaatg                8593
Gly Tyr Met Pro Pro Asp
        485 gtgttttttgg ataaacagtt taatcaaaag ttgatggtaa taaacaccta tcgcataagt      8653
gtttattcat aaactatttt gagatgttta ttgagataaa gttaaaatat ctaatgagtt       8713
tagtgactta tgaaagtaag ctctcaacaa cttataagta gggtataagg tatttacaat       8773
acataagctc taacaagcac ttagatacac acatttgagc ttatctttca caataaatgc       8833
tcgtacaagt gtttgagaga cttgtgtag cttatgcgct acctagaagc tgatttgagc        8893
ttattttcac aagttgttca tattagctta tgaataagag attatgctta tatataattt       8953
attttcagct tatttcaata agttcatcaa atttgcttat gaataagtgc ttgtgcgaca       9013
agcgcttatt gctacaagtg cttaattacg ctgtttaccc ataaacgtgt tcaattagta      9073
aagtcaagtt cagttttcaa acatatcat tgagtgaact tgttttacct ggcttttatg       9133 caga t atg ctc aat atg gtg ata ttt ctc caa aaa tag atg tat atg         9180
    Met Leu Asn Met Val Ile Phe Leu Gln Lys     Met Tyr Met
        490                 495                     500 cat ttg gag ttg ttc ttt ttg aac tta ttt ctg caa aga atg ctg ttc         9228
His Leu Glu Leu Phe Phe Leu Asn Leu Phe Leu Gln Arg Met Leu Phe
        505                 510                 515 tga aga cag gtg aat tag ttg ctg aat caa agg gcc ttg tag ctt tg         9275
    Arg Gln Val Asn     Leu Leu Asn Gln Arg Ala Leu     Leu Cys
        520                 525 gtgagtctac atgccccttc tctaaccta tttacaaacc aattactcac aatttcgaaa       9335
attttacatg tatatttcaa agctactcag cacaaatgca tttgcccctta acttgctttg    9395 cattgcag t ttg aag aag cac tta ata aga gtg atc ctt gtg atg ctc         9443
            Leu Lys Lys His Leu Ile Arg Val Ile Leu Val Met Leu
                            535                 540 ttc gca aac tgg tgg atc cta ggc ttg gag aaa act atc caa ttg att        9491
Phe Ala Asn Trp Trp Ile Leu Gly Leu Glu Lys Thr Ile Gln Leu Ile
        545                 550                 555 ctg ttc tca ag gtgggagcaa ttctcactaa aattaatttg aaatgaatta            9542
Leu Phe Ser Arg
560 ctatcattta gtcacttgaa tgactttttt tatcagaaca taagcaggtt gtgtctagtt     9602 ttcttttggt gggtttagga cttaaagtta tcttagtgta aaattttctc attttactaa    9662 accttaatgc tttattgttg tttgagttgc ag a ttg cac aac tag gga gag ctt     9716
                                     Leu His Asn     Gly Glu Leu
                                                         565 gta caa gag ata atc cac tgc taa gac caa gta tga gat ctt tag ttg       9764
Val Gln Glu Ile Ile His Cys     Asp Gln Val     Asp Leu     Leu
570             575                 580 ttg ctc tta tga ccc ttt cat cac tta ctg agg att gtg atg atg aat       9812
Leu Leu Leu     Pro Phe His His Leu Leu Arg Ile Val Met Met Asn
        585             590                 595 ctt cct acg aaa gtc aaa ctc tca taa att tac tgt ctg tga gat aa        9859
Leu Pro Thr Lys Val Lys Leu Ser     Ile Tyr Cys Leu     Asp
        600                 605                 610 aggttctcca tgcaaatgca tgtttgttat atatatcttg tagtacaact aagcagacaa     9919
```

```
aaagttttgt actttgaatg taaatcgagt cagggtgttt acattttatt actccaatgt    9979
ttaattgcca aaaccatcaa aaagtcctag gccagacttc ctgtaattat atttagcaaa   10039
gttgcagatt ctaagttcag ttttttttata tataggtttc agtattttt atatatatta   10099 ttttataaat ttttaacttt gttacaatat aaacatattt gcattcatct tcaaatcttt   10159
cagaatcact tctcctacca cagaagctaa tagaagtgtc ttccagaatc aattcttcat   10219
ccactgtgaa aatctactat gtatcaaagc atgc                               10253

<210> SEQ ID NO 24
<211> LENGTH: 621
<212> TYPE: PRT
<213> ORGANISM: Lotus japonicus Gifu

<400> SEQUENCE: 24

Met Lys Leu Lys Thr Gly Leu Leu Leu Phe Ile Leu Leu Leu Gly
1               5                   10                  15

His Val Cys Phe His Val Glu Ser Asn Cys Leu Lys Gly Cys Asp Leu
            20                  25                  30

Ala Leu Ala Ser Tyr Tyr Ile Leu Pro Gly Val Phe Ile Leu Gln Asn
        35                  40                  45

Ile Thr Thr Phe Met Gln Ser Glu Ile Val Ser Ser Asn Asp Ala Ile
    50                  55                  60

Thr Ser Tyr Asn Lys Asp Lys Ile Leu Asn Asp Ile Asn Ile Gln Ser
65                  70                  75                  80

Phe Gln Arg Leu Asn Ile Pro Phe Pro Cys Asp Cys Ile Gly Gly Glu
                85                  90                  95

Phe Leu Gly His Val Phe Glu Tyr Ser Ala Ser Lys Gly Asp Thr Tyr
            100                 105                 110

Glu Thr Ile Ala Asn Leu Tyr Tyr Ala Asn Leu Thr Thr Val Asp Leu
        115                 120                 125

Leu Lys Arg Phe Asn Ser Tyr Asp Pro Lys Asn Ile Pro Val Asn Ala
    130                 135                 140

Lys Val Asn Val Thr Val Asn Cys Ser Cys Gly Asn Ser Gln Val Ser
145                 150                 155                 160

Lys Asp Tyr Gly Leu Phe Ile Thr Tyr Pro Ile Arg Pro Gly Asp Thr
                165                 170                 175

Leu Gln Asp Ile Ala Asn Gln Ser Leu Asp Ala Gly Leu Ile Gln
            180                 185                 190

Ser Phe Asn Pro Ser Val Asn Phe Ser Lys Asp Ser Gly Ile Ala Phe
        195                 200                 205

Ile Pro Gly Arg Tyr Lys Asn Gly Val Tyr Val Pro Leu Tyr His Arg
    210                 215                 220

Thr Ala Gly Leu Ala Ser Gly Ala Ala Val Gly Ile Ser Ile Ala Gly
225                 230                 235                 240

Thr Phe Val Leu Leu Leu Ala Phe Cys Met Tyr Val Arg Tyr Gln
                245                 250                 255

Lys Lys Glu Glu Glu Lys Ala Lys Leu Pro Thr Asp Ile Ser Met Ala
            260                 265                 270

Leu Ser Thr Gln Asp Ala Ser Ser Ala Glu Tyr Glu Thr Ser Gly
        275                 280                 285

Ser Ser Gly Pro Gly Thr Ala Ser Ala Thr Gly Leu Thr Ser Ile Met
    290                 295                 300

Val Ala Lys Ser Met Glu Phe Ser Tyr Gln Glu Leu Ala Lys Ala Thr
305                 310                 315                 320
```

-continued

```
Asn Asn Phe Ser Leu Asp Asn Lys Ile Gly Gln Gly Phe Gly Ala
                325                 330                 335

Val Tyr Tyr Ala Glu Leu Arg Gly Lys Lys Thr Ala Ile Lys Lys Met
            340                 345                 350

Asp Val Gln Ala Ser Thr Glu Phe Leu Cys Glu Leu Lys Val Leu Thr
            355                 360                 365

His Val His His Leu Asn Leu Val Arg Leu Ile Gly Tyr Cys Val Glu
            370                 375                 380

Gly Ser Leu Phe Leu Val Tyr Glu His Ile Asp Asn Gly Asn Leu Gly
385                 390                 395                 400

Gln Tyr Leu His Gly Ser Gly Lys Glu Pro Leu Pro Trp Ser Ser Arg
            405                 410                 415

Val Gln Ile Ala Leu Asp Ala Ala Arg Gly Leu Glu Tyr Ile His Glu
            420                 425                 430

His Thr Val Pro Val Tyr Ile His Arg Asp Val Lys Ser Ala Asn Ile
            435                 440                 445

Leu Ile Asp Lys Asn Leu Arg Gly Lys Val Ala Asp Phe Gly Leu Thr
            450                 455                 460

Lys Leu Ile Glu Val Gly Asn Ser Thr Leu Gln Thr Arg Leu Val Gly
465                 470                 475                 480

Thr Phe Gly Tyr Met Pro Pro Glu Tyr Ala Gln Tyr Gly Asp Ile Ser
                485                 490                 495

Pro Lys Ile Asp Val Tyr Ala Phe Gly Val Val Leu Phe Glu Leu Ile
            500                 505                 510

Ser Ala Lys Asn Ala Val Leu Lys Thr Gly Glu Leu Val Ala Glu Ser
            515                 520                 525

Lys Gly Leu Val Ala Leu Phe Glu Glu Ala Leu Asn Lys Ser Asp Pro
530                 535                 540

Cys Asp Ala Leu Arg Lys Leu Val Asp Pro Arg Leu Gly Glu Asn Tyr
545                 550                 555                 560

Pro Ile Asp Ser Val Leu Lys Ile Ala Gln Leu Gly Arg Ala Cys Thr
                565                 570                 575

Arg Asp Asn Pro Leu Leu Arg Pro Ser Met Arg Ser Leu Val Val Ala
            580                 585                 590

Leu Met Thr Leu Ser Ser Leu Thr Glu Asp Cys Asp Asp Glu Ser Ser
            595                 600                 605

Tyr Glu Ser Gln Thr Leu Ile Asn Leu Leu Ser Val Arg
610                 615                 620

<210> SEQ ID NO 25
<211> LENGTH: 623
<212> TYPE: PRT
<213> ORGANISM: Lotus japonicus Gifu

<400> SEQUENCE: 25

Met Lys Leu Lys Thr Gly Leu Leu Leu Phe Ile Leu Leu Leu Gly
1               5                   10                  15

His Val Cys Phe His Val Glu Ser Asn Cys Leu Lys Gly Cys Asp Leu
            20                  25                  30

Ala Leu Ala Ser Tyr Tyr Ile Leu Pro Gly Val Phe Ile Leu Gln Asn
            35                  40                  45

Ile Thr Thr Phe Met Gln Ser Glu Ile Val Ser Ser Asn Asp Ala Ile
            50                  55                  60

Thr Ser Tyr Asn Lys Asp Lys Ile Leu Asn Asp Ile Asn Ile Gln Ser
65                  70                  75                  80
```

```
Phe Gln Arg Leu Asn Ile Pro Phe Pro Cys Asp Cys Ile Gly Gly Glu
                85                  90                  95

Phe Leu Gly His Val Phe Glu Tyr Ser Ala Ser Lys Gly Asp Thr Tyr
            100                 105                 110

Glu Thr Ile Ala Asn Leu Tyr Tyr Ala Asn Leu Thr Thr Val Asp Leu
            115                 120                 125

Leu Lys Arg Phe Asn Ser Tyr Asp Pro Lys Asn Ile Pro Val Asn Ala
        130                 135                 140

Lys Val Asn Val Thr Val Asn Cys Ser Cys Gly Asn Ser Gln Val Ser
145                 150                 155                 160

Lys Asp Tyr Gly Leu Phe Ile Thr Tyr Pro Ile Arg Pro Gly Asp Thr
                165                 170                 175

Leu Gln Asp Ile Ala Asn Gln Ser Ser Leu Asp Ala Gly Leu Ile Gln
            180                 185                 190

Ser Phe Asn Pro Ser Val Asn Phe Ser Lys Asp Ser Gly Ile Ala Phe
        195                 200                 205

Ile Pro Gly Arg Tyr Lys Asn Gly Val Tyr Val Pro Leu Tyr His Arg
    210                 215                 220

Thr Ala Gly Leu Ala Ser Gly Ala Ala Val Gly Ile Ser Ile Ala Gly
225                 230                 235                 240

Thr Phe Val Leu Leu Leu Ala Phe Cys Met Tyr Val Arg Tyr Gln
                245                 250                 255

Lys Lys Glu Glu Glu Lys Ala Lys Leu Pro Thr Asp Ile Ser Met Ala
            260                 265                 270

Leu Ser Thr Gln Asp Ala Gly Asn Ser Ser Ala Gly Tyr Glu Thr
            275                 280                 285

Ser Gly Ser Ser Gly Pro Gly Thr Ala Ser Ala Thr Gly Leu Thr Ser
        290                 295                 300

Ile Met Val Ala Lys Ser Met Glu Phe Ser Tyr Gln Glu Leu Ala Lys
305                 310                 315                 320

Ala Thr Asn Asn Phe Ser Leu Asp Asn Lys Ile Gly Gln Gly Gly Phe
                325                 330                 335

Gly Ala Val Tyr Tyr Ala Glu Leu Arg Gly Lys Lys Thr Ala Ile Lys
            340                 345                 350

Lys Met Asp Val Gln Ala Ser Thr Glu Phe Leu Cys Glu Leu Lys Val
        355                 360                 365

Leu Thr His Val His His Leu Asn Leu Val Arg Leu Ile Gly Tyr Cys
    370                 375                 380

Val Glu Gly Ser Leu Phe Leu Val Tyr Glu His Ile Asp Asn Gly Asn
385                 390                 395                 400

Leu Gly Gln Tyr Leu His Gly Ser Gly Lys Glu Pro Leu Pro Trp Ser
                405                 410                 415

Ser Arg Val Gln Ile Ala Leu Asp Ala Ala Arg Gly Leu Glu Tyr Ile
            420                 425                 430

His Glu His Thr Val Pro Val Tyr Ile His Arg Asp Val Lys Ser Ala
        435                 440                 445

Asn Ile Leu Ile Asp Lys Asn Leu Arg Gly Lys Val Ala Asp Phe Gly
    450                 455                 460

Leu Thr Lys Leu Ile Glu Val Gly Asn Ser Thr Leu Gln Thr Arg Leu
465                 470                 475                 480

Val Gly Thr Phe Gly Tyr Met Pro Pro Glu Tyr Ala Gln Tyr Gly Asp
                485                 490                 495

Ile Ser Pro Lys Ile Asp Val Tyr Ala Phe Gly Val Val Leu Phe Glu
            500                 505                 510
```

```
Leu Ile Ser Ala Lys Asn Ala Val Leu Lys Thr Gly Glu Leu Val Ala
        515                 520                 525

Glu Ser Lys Gly Leu Val Ala Leu Phe Glu Glu Ala Leu Asn Lys Ser
    530                 535                 540

Asp Pro Cys Asp Ala Leu Arg Lys Leu Val Asp Pro Arg Leu Gly Glu
545                 550                 555                 560

Asn Tyr Pro Ile Asp Ser Val Leu Lys Ile Ala Gln Leu Gly Arg Ala
                565                 570                 575

Cys Thr Arg Asp Asn Pro Leu Leu Arg Pro Ser Met Arg Ser Leu Val
            580                 585                 590

Val Ala Leu Met Thr Leu Ser Ser Leu Thr Glu Asp Cys Asp Asp Glu
            595                 600                 605

Ser Ser Tyr Glu Ser Gln Thr Leu Ile Asn Leu Leu Ser Val Arg
        610                 615                 620

<210> SEQ ID NO 26
<211> LENGTH: 19
<212> TYPE: DNA
<213> ORGANISM: Lotus japonicus

<400> SEQUENCE: 26
aatgctcttg atcaggctg                                              19

<210> SEQ ID NO 27
<211> LENGTH: 20
<212> TYPE: DNA
<213> ORGANISM: Lotus japonicus

<400> SEQUENCE: 27
aggagcccaa gtgagtgcta                                             20

<210> SEQ ID NO 28
<211> LENGTH: 20
<212> TYPE: DNA
<213> ORGANISM: Lotus japonicus

<400> SEQUENCE: 28
caggaaaaac caccacctgt                                             20

<210> SEQ ID NO 29
<211> LENGTH: 21
<212> TYPE: DNA
<213> ORGANISM: Lotus japonicus

<400> SEQUENCE: 29
atggaggcga atacactggt g                                           21

<210> SEQ ID NO 30
<211> LENGTH: 1853
<212> TYPE: DNA
<213> ORGANISM: Lotus filicaulis

<400> SEQUENCE: 30
ttttctcttt ccctgttaac tatcatttgt tcccaacttc acaaacatgg ctgtcttctt   60
tcttacctct ggctctctga gtcttttttct tgcactcacg ttgcttttca ctaacatcgc  120
cgctcgatca gaacagatca gcggcccaga cttttcatgc cctgttgact cacctccttc  180
ttgtgaaaca tatgtgacat acacagctca gtctccaaat cttctgagcc tgacaaaacat 240 atctgatata tttgatatca gtcctttgtc cattgcaaga gccagtaaca tagatgcagg  300
```

-continued

```
gaaggacaag ctggttccag gccaagtctt actggtacct gtaacttgcg gttgcgccgg    360
aaaccactct tctgccaata cctcctacca aatccagaaa ggtgatagct acgactttgt    420
tgcaaccact ttatatgaga accttacaaa ttggaatata gtacaagctt caaacccagg    480
ggtaaatcca tatttgttgc cagagcgcgt caaagtcgta ttccctttat ctgcaggtg     540
cccttcaaag aaccagttga acaaagggat tcagtatctg attacttatg tgtggaagcc    600
caatgacaat gtttcccttg tgagtgccaa gtttggtgca tccccagcgg acatattgac    660
tgaaaaccgc tacggtcaag acttcactgc tgcaaccaac cttccaattt tgatcccagt    720
gacacagttg ccaaagctta ctcaaccttc ttcaaatgga aggaaaagca gcattcatct    780
tctggttata cttggtatta ccctgggatg cacgttgcta actgcagttt taaccgggac    840
cctcgtatat gtatactgcc gcagaaagaa ggctctgaat aggactgctt catcagctga    900
gactgctgat aaactacttt ctggagtttc aggctatgta agcaagccaa acgtgtatga    960
aatcgacgag ataatggaag ctacgaagga tttcagcgat gagtgcaagg ttggggaatc   1020
agtgtacaag gccaacatag aaggtcgggt tgtagcggta agaaaatca aggaaggtgg    1080
tgccaatgag gaactgaaaa ttctgcagaa ggtaaatcat ggaaatctgg tgaaactaat   1140
gggtgtctcc tcaggctatg atggaaactg tttcttggtt tatgaatatg ctgaaaatgg   1200
gtctcttgct gagtggctgt tctccaagtc ttcaggaacc ccaaactccc ttacatggtc   1260
tcaaaggata agcatagcag tggatgttgc tgtgggtctg caatacatgc atgaacatac   1320
ctatccaaga ataatacaca gggacatcac aacaagtaat atccttctcg actcgacctt   1380
caaggccaag atagcaaatt tcgccatggc cagaacttcg accaaccccca tgatgccaaa   1440
aatcgatgtc ttcgctttcg gggtgcttct gatagagttg ctcaccggaa ggaaagccat   1500
gacaaccaag gagaacggcg aggtggttat gctgtggaag gatatgtggg agatctttga   1560
catagaagag aatagagagg agaggatcag aaaatggatg gatcctaatt tagagagctt   1620
ttatcatata gataatgctc tcagcttggc atccttagca gtgaattgca cagctgataa   1680
gtctttgtct cgaccctcca tggctgaaat tgttcttagc ctctcctttc tcactcaaca   1740
atcatctaac cccacattag agagatcctt gacttcttct gggttagatg tagaagatga   1800
tgctcatatt gtcacttcca ttacagcacg ttaagcaagg gaaggtaatt cag          1853
```

```
<210> SEQ ID NO 31
<211> LENGTH: 595
<212> TYPE: PRT
<213> ORGANISM: Lotus filicaulis

<400> SEQUENCE: 31
```

Met Ala Val Phe Phe Leu Thr Ser Gly Ser Leu Ser Leu Phe Leu Ala
1               5                   10                  15

Leu Thr Leu Leu Phe Thr Asn Ile Ala Ala Arg Ser Glu Gln Ile Ser
            20                  25                  30

Gly Pro Asp Phe Ser Cys Pro Val Asp Ser Pro Ser Cys Glu Thr
        35                  40                  45

Tyr Val Thr Tyr Thr Ala Gln Ser Pro Asn Leu Ser Leu Thr Asn
    50                  55                  60

Ile Ser Asp Ile Phe Asp Ile Ser Pro Leu Ser Ile Ala Arg Ala Ser
65                  70                  75                  80

Asn Ile Asp Ala Gly Lys Asp Lys Leu Val Pro Gly Gln Val Leu Leu
                85                  90                  95

Val Pro Val Thr Cys Gly Cys Ala Gly Asn His Ser Ser Ala Asn Thr
            100                 105                 110

-continued

```
Ser Tyr Gln Ile Gln Lys Gly Asp Ser Tyr Asp Phe Val Ala Thr Thr
            115                 120                 125
Leu Tyr Glu Asn Leu Thr Asn Trp Asn Ile Val Gln Ala Ser Asn Pro
    130                 135                 140
Gly Val Asn Pro Tyr Leu Leu Pro Glu Arg Val Lys Val Val Phe Pro
145                 150                 155                 160
Leu Phe Cys Arg Cys Pro Ser Lys Asn Gln Leu Asn Lys Gly Ile Gln
                165                 170                 175
Tyr Leu Ile Thr Tyr Val Trp Lys Pro Asn Asp Asn Val Ser Leu Val
            180                 185                 190
Ser Ala Lys Phe Gly Ala Ser Pro Ala Asp Ile Leu Thr Glu Asn Arg
        195                 200                 205
Tyr Gly Gln Asp Phe Thr Ala Ala Thr Asn Leu Pro Ile Leu Ile Pro
    210                 215                 220
Val Thr Gln Leu Pro Lys Leu Thr Gln Pro Ser Ser Asn Gly Arg Lys
225                 230                 235                 240
Ser Ser Ile His Leu Leu Val Ile Leu Gly Ile Thr Leu Gly Cys Thr
                245                 250                 255
Leu Leu Thr Ala Val Leu Thr Gly Thr Leu Val Tyr Val Tyr Cys Arg
            260                 265                 270
Arg Lys Lys Ala Leu Asn Arg Thr Ala Ser Ser Ala Glu Thr Ala Asp
        275                 280                 285
Lys Leu Leu Ser Gly Val Ser Gly Tyr Val Ser Lys Pro Asn Val Tyr
    290                 295                 300
Glu Ile Asp Glu Ile Met Glu Ala Thr Lys Asp Phe Ser Asp Glu Cys
305                 310                 315                 320
Lys Val Gly Glu Ser Val Tyr Lys Ala Asn Ile Glu Gly Arg Val Val
                325                 330                 335
Ala Val Lys Lys Ile Lys Glu Gly Gly Ala Asn Glu Glu Leu Lys Ile
            340                 345                 350
Leu Gln Lys Val Asn His Gly Asn Leu Val Lys Leu Met Gly Val Ser
        355                 360                 365
Ser Gly Tyr Asp Gly Asn Cys Phe Leu Val Tyr Glu Tyr Ala Glu Asn
    370                 375                 380
Gly Ser Leu Ala Glu Trp Leu Phe Ser Lys Ser Ser Gly Thr Pro Asn
385                 390                 395                 400
Ser Leu Thr Trp Ser Gln Arg Ile Ser Ile Ala Val Asp Val Ala Val
                405                 410                 415
Gly Leu Gln Tyr Met His Glu His Thr Tyr Pro Arg Ile Ile His Arg
            420                 425                 430
Asp Ile Thr Thr Ser Asn Ile Leu Leu Asp Ser Thr Phe Lys Ala Lys
        435                 440                 445
Ile Ala Asn Phe Ala Met Ala Arg Thr Ser Thr Asn Pro Met Met Pro
    450                 455                 460
Lys Ile Asp Val Phe Ala Phe Gly Val Leu Leu Ile Glu Leu Leu Thr
465                 470                 475                 480
Gly Arg Lys Ala Met Thr Thr Lys Glu Asn Gly Glu Val Val Met Leu
                485                 490                 495
Trp Lys Asp Met Trp Glu Ile Phe Asp Ile Glu Glu Asn Arg Glu Glu
            500                 505                 510
Arg Ile Arg Lys Trp Met Asp Pro Asn Leu Glu Ser Phe Tyr His Ile
        515                 520                 525
Asp Asn Ala Leu Ser Leu Ala Ser Leu Ala Val Asn Cys Thr Ala Asp
```

```
                    530                 535                 540
Lys Ser Leu Ser Arg Pro Ser Met Ala Glu Ile Val Leu Ser Leu Ser
545                 550                 555                 560

Phe Leu Thr Gln Gln Ser Ser Asn Pro Thr Leu Glu Arg Ser Leu Thr
                565                 570                 575

Ser Ser Gly Leu Asp Val Glu Asp Asp Ala His Ile Val Thr Ser Ile
                580                 585                 590

Thr Ala Arg
        595

<210> SEQ ID NO 32
<211> LENGTH: 595
<212> TYPE: PRT
<213> ORGANISM: Medicago truncatula
<220> FEATURE:
<221> NAME/KEY: PEPTIDE
<222> LOCATION: (1)..(595)

<400> SEQUENCE: 32

Met Ser Ala Phe Phe Leu Pro Ser Ser His Ala Leu Phe Leu Val
1               5                   10                  15

Leu Met Leu Phe Phe Leu Thr Asn Ile Ser Ala Gln Pro Leu Tyr Ile
                20                  25                  30

Ser Glu Thr Asn Phe Thr Cys Pro Val Asp Ser Pro Pro Ser Cys Glu
                35                  40                  45

Thr Tyr Val Ala Tyr Arg Ala Gln Ser Pro Asn Phe Leu Ser Leu Ser
            50                  55                  60

Asn Ile Ser Asp Ile Phe Asn Leu Ser Pro Leu Arg Ile Ala Lys Ala
65              70                  75                  80

Ser Asn Ile Glu Ala Glu Asp Lys Lys Leu Ile Pro Asp Gln Leu Leu
                85                  90                  95

Leu Val Pro Val Thr Cys Gly Cys Thr Lys Asn His Ser Phe Ala Asn
                100                 105                 110

Ile Thr Tyr Ser Ile Lys Gln Gly Asp Asn Phe Phe Ile Leu Ser Ile
            115                 120                 125

Thr Ser Tyr Gln Asn Leu Thr Asn Tyr Leu Glu Phe Lys Asn Phe Asn
            130                 135                 140

Pro Asn Leu Ser Pro Thr Leu Leu Pro Leu Asp Thr Lys Val Ser Val
145                 150                 155                 160

Pro Leu Phe Cys Lys Cys Pro Ser Lys Asn Gln Leu Asn Lys Gly Ile
                165                 170                 175

Lys Tyr Leu Ile Thr Tyr Val Trp Gln Asp Asn Asp Asn Val Thr Leu
                180                 185                 190

Val Ser Ser Lys Phe Gly Ala Ser Gln Val Glu Met Leu Ala Glu Asn
            195                 200                 205

Asn His Asn Phe Thr Ala Ser Thr Asn Arg Ser Val Leu Ile Pro Val
210                 215                 220

Thr Ser Leu Pro Lys Leu Asp Gln Pro Ser Ser Asn Gly Arg Lys Ser
225                 230                 235                 240

Ser Ser Gln Asn Leu Ala Leu Ile Ile Gly Ile Ser Leu Gly Ser Ala
                245                 250                 255

Phe Phe Ile Leu Val Leu Thr Leu Ser Leu Val Tyr Tyr Cys Leu
                260                 265                 270

Lys Met Lys Arg Leu Asn Arg Ser Thr Ser Ser Glu Thr Ala Asp
                275                 280                 285

Lys Leu Leu Ser Gly Val Ser Gly Tyr Val Ser Lys Pro Thr Met Tyr
```

```
                290                 295                 300
Glu Ile Asp Ala Ile Met Glu Gly Thr Thr Asn Leu Ser Asp Asn Cys
305                 310                 315                 320

Lys Ile Gly Glu Ser Val Tyr Lys Ala Asn Ile Asp Gly Arg Val Leu
                325                 330                 335

Ala Val Lys Lys Ile Lys Lys Asp Ala Ser Glu Leu Lys Ile Leu
            340                 345                 350

Gln Lys Val Asn His Gly Asn Leu Val Lys Leu Met Gly Val Ser Ser
                355                 360                 365

Asp Asn Asp Gly Asp Cys Phe Leu Val Tyr Glu Tyr Ala Glu Asn Gly
            370                 375                 380

Ser Leu Glu Glu Trp Leu Phe Ser Glu Ser Ser Lys Thr Ser Asn Ser
385                 390                 395                 400

Val Val Ser Leu Thr Trp Ser Gln Arg Ile Thr Ile Ala Met Asp Val
                405                 410                 415

Ala Ile Gly Leu Gln Tyr Met His Glu His Thr Tyr Pro Arg Ile Ile
            420                 425                 430

His Arg Asp Ile Thr Thr Ser Asn Ile Leu Leu Gly Ser Asn Phe Lys
            435                 440                 445

Ala Lys Ile Ala Asn Phe Gly Met Ala Arg Thr Ser Thr Asn Ser Met
450                 455                 460

Met Pro Lys Ile Asp Val Phe Ala Phe Gly Val Val Leu Ile Glu Leu
465                 470                 475                 480

Leu Thr Gly Lys Lys Ala Met Thr Thr Lys Glu Asn Gly Glu Val Val
            485                 490                 495

Ile Leu Trp Lys Asp Phe Trp Lys Ile Phe Asp Leu Glu Gly Asn Arg
            500                 505                 510

Glu Glu Arg Leu Arg Lys Trp Met Asp Pro Lys Leu Glu Ser Phe Tyr
            515                 520                 525

Pro Ile Asp Asn Ala Leu Ser Leu Ala Ser Leu Ala Val Asn Cys Thr
530                 535                 540

Ala Asp Lys Ser Leu Ser Arg Pro Thr Ile Ala Glu Ile Val Leu Cys
545                 550                 555                 560

Leu Ser Leu Leu Asn Gln Pro Ser Ser Glu Pro Met Leu Glu Arg Ser
                565                 570                 575

Leu Thr Ser Gly Leu Asp Ala Glu Ala Thr His Val Val Thr Ser Val
            580                 585                 590

Ile Ala Arg
        595

<210> SEQ ID NO 33
<211> LENGTH: 24
<212> TYPE: DNA
<213> ORGANISM: Phaseolus vulgaris
<220> FEATURE:
<221> NAME/KEY: misc_feature
<222> LOCATION: (1)..(24)
<223> OTHER INFORMATION: Primer to amplify fragment of NPR5

<400> SEQUENCE: 33
cattgcaara gccagtaaca taga                                          24

<210> SEQ ID NO 34
<211> LENGTH: 30
<212> TYPE: DNA
<213> ORGANISM: Phaseolus vulgaris
<220> FEATURE:
<221> NAME/KEY: misc_feature
```

```
<222> LOCATION: (1)..(30)
<223> OTHER INFORMATION: To ampify a fragment of NPR5

<400> SEQUENCE: 34
aacgwgcwry wayrgaagtm acaayatgag                                    30

<210> SEQ ID NO 35
<211> LENGTH: 35
<212> TYPE: DNA
<213> ORGANISM: Phaseolus vulgaris
<220> FEATURE:
<221> NAME/KEY: misc_feature
<222> LOCATION: (1)..(35)
<223> OTHER INFORMATION: NPR5 5'RACE primer

<400> SEQUENCE: 35
cgactgggat atgtatgtca catatgtttc acatg                              35

<210> SEQ ID NO 36
<211> LENGTH: 22
<212> TYPE: DNA
<213> ORGANISM: Phaseolus vulgaris
<220> FEATURE:
<221> NAME/KEY: misc_feature
<222> LOCATION: (1)..(22)
<223> OTHER INFORMATION: NPR5 3' RACE primer

<400> SEQUENCE: 36
gatagaattg cttactggca gg                                            22

<210> SEQ ID NO 37
<211> LENGTH: 21
<212> TYPE: DNA
<213> ORGANISM: Phaseolus vulgaris
<220> FEATURE:
<221> NAME/KEY: misc_feature
<222> LOCATION: (1)..(21)

<400> SEQUENCE: 37
gacgtgtcca ctgtatccag g                                             21

<210> SEQ ID NO 38
<211> LENGTH: 24
<212> TYPE: DNA
<213> ORGANISM: Phaseolus vulgaris
<220> FEATURE:
<221> NAME/KEY: misc_feature
<222> LOCATION: (1)..(24)
<223> OTHER INFORMATION: NPR5 gene PCR primer

<400> SEQUENCE: 38
gtttggacat gcaataaaca actc                                          24

<210> SEQ ID NO 39
<211> LENGTH: 2164
<212> TYPE: DNA
<213> ORGANISM: Phaseolus vulgaris
<220> FEATURE:
<221> NAME/KEY: 5'UTR
<222> LOCATION: (1)..(172)
<220> FEATURE:
<221> NAME/KEY: CDS
<222> LOCATION: (173)..(1963)
<220> FEATURE:
<221> NAME/KEY: 3'UTR
<222> LOCATION: (1964)..(2164)

<400> SEQUENCE: 39
ggattcggaa agccaaaagg aaatttagtt aaagctaatg acacaaacag gaccatattt   60
```

-continued

| | |
|---|---|
| ttatattaag ccaaaagata tttttattga caaagaacta catatcaaca acgacgattg | 120 |
| ccagtgatag tagactgcct cataactttc atttgttcac aacttcacat ca atg gct<br>　　　　　　　　　　　　　　　　　　　　　　　　　　　　　Met Ala<br>　　　　　　　　　　　　　　　　　　　　　　　　　　　　　　1 | 178 |
| gtc ttc ttt gtt tct ctt act ctt ggt gct cag att ctt tat gtg gta<br>Val Phe Phe Val Ser Leu Thr Leu Gly Ala Gln Ile Leu Tyr Val Val<br>　　　5　　　　　　　　　　　10　　　　　　　　　　　15 | 226 |
| ctc atg ttt ttc act tgt att gaa gct caa tca caa cag acc aat gga<br>Leu Met Phe Phe Thr Cys Ile Glu Ala Gln Ser Gln Gln Thr Asn Gly<br>20　　　　　　　　　　　25　　　　　　　　　　　30 | 274 |
| aca aac ttt tca tgc cct tcc aat tca cct cct tca tgt gaa aca tat<br>Thr Asn Phe Ser Cys Pro Ser Asn Ser Pro Pro Ser Cys Glu Thr Tyr<br>35　　　　　　　　　　40　　　　　　　　　　　45　　　　　　　　　　50 | 322 |
| gtg aca tac ata tcc cag tcg cca aat ttt ttg agt ctg acc agc gta<br>Val Thr Tyr Ile Ser Gln Ser Pro Asn Phe Leu Ser Leu Thr Ser Val<br>　　　　　　　　　　55　　　　　　　　　　　60　　　　　　　　　　　65 | 370 |
| tct aat ata ttt gac acg agt cct ttg tca att gcc aga gcc agc aac<br>Ser Asn Ile Phe Asp Thr Ser Pro Leu Ser Ile Ala Arg Ala Ser Asn<br>　　　　　　　　70　　　　　　　　　　　75　　　　　　　　　　　80 | 418 |
| tta cag cat gag gaa gac aag ttg att cca ggc caa gtc tta ctg ata<br>Leu Gln His Glu Glu Asp Lys Leu Ile Pro Gly Gln Val Leu Leu Ile<br>　　　　　85　　　　　　　　　　　90　　　　　　　　　　　95 | 466 |
| cca gta acc tgt ggt tgc act gga aac cgc tct ttc gcc aac atc tcc<br>Pro Val Thr Cys Gly Cys Thr Gly Asn Arg Ser Phe Ala Asn Ile Ser<br>100　　　　　　　　　　105　　　　　　　　　　110 | 514 |
| tat gag atc aac caa ggt gat agc ttc tac ttt gtt gcg acc act tta<br>Tyr Glu Ile Asn Gln Gly Asp Ser Phe Tyr Phe Val Ala Thr Thr Leu<br>115　　　　　　　　　　120　　　　　　　　　　125　　　　　　　　　　130 | 562 |
| tac cag aat ctc aca aat tgg cat gca gtg atg gat tta aac cca ggt<br>Tyr Gln Asn Leu Thr Asn Trp His Ala Val Met Asp Leu Asn Pro Gly<br>　　　　　　　　　135　　　　　　　　　　140　　　　　　　　　　145 | 610 |
| cta agt caa ttt act ttg cca ata ggc atc caa gtt gta att cct tta<br>Leu Ser Gln Phe Thr Leu Pro Ile Gly Ile Gln Val Val Ile Pro Leu<br>　　　　　　　　　150　　　　　　　　　　155　　　　　　　　　　160 | 658 |
| ttc tgc aag tgt cct tca aag aac cag ctg gat aga ggg ata aag tac<br>Phe Cys Lys Cys Pro Ser Lys Asn Gln Leu Asp Arg Gly Ile Lys Tyr<br>　　　　　165　　　　　　　　　　170　　　　　　　　　　175 | 706 |
| ctg atc act cac gtc tgg cag ccc aat gac aat gtt tcc ttt gta agt<br>Leu Ile Thr His Val Trp Gln Pro Asn Asp Asn Val Ser Phe Val Ser<br>180　　　　　　　　　　185　　　　　　　　　　190 | 754 |
| aac aag tta ggt gca tca cca cag gac ata ttg agt gaa aac aac tat<br>Asn Lys Leu Gly Ala Ser Pro Gln Asp Ile Leu Ser Glu Asn Asn Tyr<br>195　　　　　　　　　　200　　　　　　　　　　205　　　　　　　　　　210 | 802 |
| ggt caa aat ttc act gcc gca agc aac ctt cca gtt ttg atc cca gtt<br>Gly Gln Asn Phe Thr Ala Ala Ser Asn Leu Pro Val Leu Ile Pro Val<br>　　　　　　　　　215　　　　　　　　　　220　　　　　　　　　　225 | 850 |
| aca ctc ttg cca gat ctt att caa tct cct tca gat gga aga aaa cac<br>Thr Leu Leu Pro Asp Leu Ile Gln Ser Pro Ser Asp Gly Arg Lys His<br>　　　　　　　　　230　　　　　　　　　　235　　　　　　　　　　240 | 898 |
| aga att ggt ctt cca gtt ata att ggt atc agc ctg gat gca cta cta<br>Arg Ile Gly Leu Pro Val Ile Ile Gly Ile Ser Leu Gly Cys Thr Leu<br>　　　　　245　　　　　　　　　　250　　　　　　　　　　255 | 946 |
| ctg gtt gtg gtt tca gca ata tta ctg gtg tgt gta tgt tgt ctg aaa<br>Leu Val Val Val Ser Ala Ile Leu Leu Val Cys Val Cys Cys Leu Lys<br>260　　　　　　　　　　265　　　　　　　　　　270 | 994 |
| atg aag agt ttg aat agg agt gct tca tca gct gaa act gca gat aaa<br>Met Lys Ser Leu Asn Arg Ser Ala Ser Ser Ala Glu Thr Ala Asp Lys<br>275　　　　　　　　　　280　　　　　　　　　　285　　　　　　　　　　290 | 1042 |
| cta ctt tct gga gtt tca ggc tat gta agt aag cct aca atg tat gaa | 1090 |

```
                    Leu Leu Ser Gly Val Ser Gly Tyr Val Ser Lys Pro Thr Met Tyr Glu
                                    295                 300                 305
act ggt gca ata ttg gaa gct act atg aac ctc agt gag cag tgc aag              1138
Thr Gly Ala Ile Leu Glu Ala Thr Met Asn Leu Ser Glu Gln Cys Lys
                310                 315                 320 att ggg gaa tca gtg tac aag gct aac ata gag ggt aag gtt tta gca              1186
Ile Gly Glu Ser Val Tyr Lys Ala Asn Ile Glu Gly Lys Val Leu Ala
                325                 330                 335 gta aaa aga ttc aag gaa gat gtc acg gag gag ctg aaa att ctg cag              1234
Val Lys Arg Phe Lys Glu Asp Val Thr Glu Glu Leu Lys Ile Leu Gln
    340                 345                 350 aag gtg aat cat gga aat ctg gtg aaa cta atg ggt gtc tca tca gat              1282
Lys Val Asn His Gly Asn Leu Val Lys Leu Met Gly Val Ser Ser Asp
355                 360                 365                 370 aat gat gga aat tgt ttt gtg gtt tat gaa tat gct gaa aat ggg tct              1330
Asn Asp Gly Asn Cys Phe Val Val Tyr Glu Tyr Ala Glu Asn Gly Ser
                    375                 380                 385 ctt gaa gag tgg ctt ttc gcc aag tct tgt tca gag aca tca aac tca              1378
Leu Glu Glu Trp Leu Phe Ala Lys Ser Cys Ser Glu Thr Ser Asn Ser
                390                 395                 400 agg acc tcc ctt aca tgg tgc cag agg ata agc ata gca gtg gat gtt              1426
Arg Thr Ser Leu Thr Trp Cys Gln Arg Ile Ser Ile Ala Val Asp Val
            405                 410                 415 tca atg ggt ctg cag tac atg cat gaa cat gct tat cca aga ata gtc              1474
Ser Met Gly Leu Gln Tyr Met His Glu His Ala Tyr Pro Arg Ile Val
        420                 425                 430 cac agg gac atc aca agc agt aat atc ctt ctt gac tcc aac ttt aag              1522
His Arg Asp Ile Thr Ser Ser Asn Ile Leu Leu Asp Ser Asn Phe Lys
435                 440                 445                 450 gcc aag ata gca aat ttc tcc atg gcc aga act ttt acc aac ccc atg              1570
Ala Lys Ile Ala Asn Phe Ser Met Ala Arg Thr Phe Thr Asn Pro Met
                    455                 460                 465 atg tca aaa ata gat gta ttt gct ttt ggg gtg gtt ctg ata gaa ttg              1618
Met Ser Lys Ile Asp Val Phe Ala Phe Gly Val Val Leu Ile Glu Leu
                470                 475                 480 ctt act ggc agg aaa gcc atg aca acc aaa gaa aat ggt gag gtg gtt              1666
Leu Thr Gly Arg Lys Ala Met Thr Thr Lys Glu Asn Gly Glu Val Val
            485                 490                 495 atg ctg tgg aag gac att tgg aag atc ttt gat caa gaa gag aat aga              1714
Met Leu Trp Lys Asp Ile Trp Lys Ile Phe Asp Gln Glu Glu Asn Arg
        500                 505                 510 gag gag agg ctc aga aaa tgg atg gat cct aag tta gat aat tat tat              1762
Glu Glu Arg Leu Arg Lys Trp Met Asp Pro Lys Leu Asp Asn Tyr Tyr
515                 520                 525                 530 cct att gat tat gct ctc agc ttg gcc tcc ttg gca gtg aat tgc act              1810
Pro Ile Asp Tyr Ala Leu Ser Leu Ala Ser Leu Ala Val Asn Cys Thr
                    535                 540                 545 gca gac aag tct ttg tcc aga cca acc ata gca gaa att gtc ctt agt              1858
Ala Asp Lys Ser Leu Ser Arg Pro Thr Ile Ala Glu Ile Val Leu Ser
                550                 555                 560 ctc tcc ctt ctc act caa cca tct ccc gcg aca ctg gag aga tcc ttg              1906
Leu Ser Leu Leu Thr Gln Pro Ser Pro Ala Thr Leu Glu Arg Ser Leu
            565                 570                 575 act tct tct gga tta gat gta gaa gct act caa att gtc act tcc atc              1954
Thr Ser Ser Gly Leu Asp Val Glu Ala Thr Gln Ile Val Thr Ser Ile
        580                 585                 590 tca gct cgt tgattgagtg aagccaatct agtttctcac atccaagatg                      2003
Ser Ala Arg
595 gtacttttt ttaaataatg attgcacctt agtcaataat gatgaacttg gtttatgggg             2063
```

```
agttttcaac atttagtgtt tccatccctg ttgttcttta tgtttgaggt agagttcgta    2123
aaacgaatag caattgcagt tctcctcaga ctaaatttgc t                         2164
```

<210> SEQ ID NO 40
<211> LENGTH: 597
<212> TYPE: PRT
<213> ORGANISM: Phaseolus vulgaris

<400> SEQUENCE: 40

```
Met Ala Val Phe Phe Val Ser Leu Thr Leu Gly Ala Gln Ile Leu Tyr
1               5                   10                  15

Val Val Leu Met Phe Phe Thr Cys Ile Glu Ala Gln Ser Gln Gln Thr
            20                  25                  30

Asn Gly Thr Asn Phe Ser Cys Pro Ser Asn Ser Pro Ser Cys Glu
        35                  40                  45

Thr Tyr Val Thr Tyr Ile Ser Gln Ser Pro Asn Phe Leu Ser Leu Thr
    50                  55                  60

Ser Val Ser Asn Ile Phe Asp Thr Ser Pro Leu Ser Ile Ala Arg Ala
65                  70                  75                  80

Ser Asn Leu Gln His Glu Glu Asp Lys Leu Ile Pro Gly Gln Val Leu
                85                  90                  95

Leu Ile Pro Val Thr Cys Gly Cys Thr Gly Asn Arg Ser Phe Ala Asn
            100                 105                 110

Ile Ser Tyr Glu Ile Asn Gln Gly Asp Ser Phe Tyr Phe Val Ala Thr
        115                 120                 125

Thr Leu Tyr Gln Asn Leu Thr Asn Trp His Ala Val Met Asp Leu Asn
    130                 135                 140

Pro Gly Leu Ser Gln Phe Thr Leu Pro Ile Gly Ile Gln Val Val Ile
145                 150                 155                 160

Pro Leu Phe Cys Lys Cys Pro Ser Lys Asn Gln Leu Asp Arg Gly Ile
                165                 170                 175

Lys Tyr Leu Ile Thr His Val Trp Gln Pro Asn Asp Asn Val Ser Phe
            180                 185                 190

Val Ser Asn Lys Leu Gly Ala Ser Pro Gln Asp Ile Leu Ser Glu Asn
        195                 200                 205

Asn Tyr Gly Gln Asn Phe Thr Ala Ala Ser Asn Leu Pro Val Leu Ile
    210                 215                 220

Pro Val Thr Leu Leu Pro Asp Leu Ile Gln Ser Pro Ser Asp Gly Arg
225                 230                 235                 240

Lys His Arg Ile Gly Leu Pro Val Ile Gly Ile Ser Leu Gly Cys
                245                 250                 255

Thr Leu Leu Val Val Ser Ala Ile Leu Leu Val Cys Val Cys Cys
            260                 265                 270

Leu Lys Met Lys Ser Leu Asn Arg Ser Ala Ser Ala Glu Thr Ala
        275                 280                 285

Asp Lys Leu Leu Ser Gly Val Ser Gly Tyr Val Ser Lys Pro Thr Met
    290                 295                 300

Tyr Glu Thr Gly Ala Ile Leu Glu Ala Thr Met Asn Leu Ser Glu Gln
305                 310                 315                 320

Cys Lys Ile Gly Glu Ser Val Tyr Lys Ala Asn Ile Glu Gly Lys Val
                325                 330                 335

Leu Ala Val Lys Arg Phe Lys Glu Asp Val Thr Glu Glu Leu Lys Ile
            340                 345                 350

Leu Gln Lys Val Asn His Gly Asn Leu Val Lys Leu Met Gly Val Ser
```

355                 360                 365
Ser Asp Asn Asp Gly Asn Cys Phe Val Val Tyr Glu Tyr Ala Glu Asn
        370                 375                 380

Gly Ser Leu Glu Glu Trp Leu Phe Ala Lys Ser Cys Ser Glu Thr Ser
385                 390                 395                 400

Asn Ser Arg Thr Ser Leu Thr Trp Cys Gln Arg Ile Ser Ile Ala Val
                405                 410                 415

Asp Val Ser Met Gly Leu Gln Tyr Met His Glu His Ala Tyr Pro Arg
            420                 425                 430

Ile Val His Arg Asp Ile Thr Ser Ser Asn Ile Leu Leu Asp Ser Asn
        435                 440                 445

Phe Lys Ala Lys Ile Ala Asn Phe Ser Met Ala Arg Thr Phe Thr Asn
    450                 455                 460

Pro Met Met Ser Lys Ile Asp Val Phe Ala Phe Gly Val Val Leu Ile
465                 470                 475                 480

Glu Leu Leu Thr Gly Arg Lys Ala Met Thr Thr Lys Glu Asn Gly Glu
                485                 490                 495

Val Val Met Leu Trp Lys Asp Ile Trp Lys Ile Phe Asp Gln Glu Glu
            500                 505                 510

Asn Arg Glu Glu Arg Leu Arg Lys Trp Met Asp Pro Lys Leu Asp Asn
        515                 520                 525

Tyr Tyr Pro Ile Asp Tyr Ala Leu Ser Leu Ala Ser Leu Ala Val Asn
    530                 535                 540

Cys Thr Ala Asp Lys Ser Leu Ser Arg Pro Thr Ile Ala Glu Ile Val
545                 550                 555                 560

Leu Ser Leu Ser Leu Leu Thr Gln Pro Ser Pro Ala Thr Leu Glu Arg
                565                 570                 575

Ser Leu Thr Ser Ser Gly Leu Asp Val Glu Ala Thr Gln Ile Val Thr
            580                 585                 590

Ser Ile Ser Ala Arg
        595

<210> SEQ ID NO 41
<211> LENGTH: 24
<212> TYPE: DNA
<213> ORGANISM: Glycine max
<220> FEATURE:
<221> NAME/KEY: misc_feature
<222> LOCATION: (1)..(24)
<223> OTHER INFORMATION: Primer to amplify NPR5 gene fragment

<400> SEQUENCE: 41
cattgcaara gccagtaaca taga                                          24

<210> SEQ ID NO 42
<211> LENGTH: 30
<212> TYPE: DNA
<213> ORGANISM: Glycine max
<220> FEATURE:
<221> NAME/KEY: misc_feature
<222> LOCATION: (1)..(30)
<223> OTHER INFORMATION: Primer to amplify NPR5 gene fragment

<400> SEQUENCE: 42
aacgwgcwry wayrgaagtm acaayatgag                                    30

<210> SEQ ID NO 43
<211> LENGTH: 31
<212> TYPE: DNA
<213> ORGANISM: Glycine max

```
<220> FEATURE:
<221> NAME/KEY: misc_feature
<222> LOCATION: (1)..(31)
<223> OTHER INFORMATION: NPR5 5'RACE primer

<400> SEQUENCE: 43
ccatcactgc acgccaattc gtgagattct c                                      31

<210> SEQ ID NO 44
<211> LENGTH: 19
<212> TYPE: DNA
<213> ORGANISM: Glycine max
<220> FEATURE:
<221> NAME/KEY: misc_feature
<222> LOCATION: (1)..(19)
<223> OTHER INFORMATION: NPR5 3'RACE primer

<400> SEQUENCE: 44
gatgtctttg catttgggg                                                    19

<210> SEQ ID NO 45
<211> LENGTH: 26
<212> TYPE: DNA
<213> ORGANISM: Glycine max
<220> FEATURE:
<221> NAME/KEY: misc_feature
<222> LOCATION: (1)..(26)
<223> OTHER INFORMATION: NPR5 gene PCR primers

<400> SEQUENCE: 45
ctaatacgac ataccaacaa ctgcag                                            26

<210> SEQ ID NO 46
<211> LENGTH: 24
<212> TYPE: DNA
<213> ORGANISM: Glycine max
<220> FEATURE:
<221> NAME/KEY: misc_feature
<222> LOCATION: (1)..(24)
<223> OTHER INFORMATION: NPR5 gene PCR primer

<400> SEQUENCE: 46
ctcgcttgaa tttgtttgta catg                                              24

<210> SEQ ID NO 47
<211> LENGTH: 2130
<212> TYPE: DNA
<213> ORGANISM: Glycine max
<220> FEATURE:
<221> NAME/KEY: 5'UTR
<222> LOCATION: (1)..(68)
<220> FEATURE:
<221> NAME/KEY: CDS
<222> LOCATION: (69)..(1862)
<220> FEATURE:
<221> NAME/KEY: 3'UTR
<222> LOCATION: (1863)..(2130)

<400> SEQUENCE: 47
ttgcctgtga taatagactc tccttattct ttccctcgtt acttacattt gttcacaact        60 aaacagca atg gct gtc ttc ttt ccc ttt ctt cct ctc cac tct cag att       110
        Met Ala Val Phe Phe Pro Phe Leu Pro Leu His Ser Gln Ile
          1               5                  10 ctt tgt ctt gtg atc atg ttg ttt tcc act aat att gta gct caa tca       158
Leu Cys Leu Val Ile Met Leu Phe Ser Thr Asn Ile Val Ala Gln Ser
 15                  20                  25                  30 caa cag gac aat aga aca aac ttt tca tgc cct tct gat tca ccg cct       206
Gln Gln Asp Asn Arg Thr Asn Phe Ser Cys Pro Ser Asp Ser Pro Pro
```

```
                      35                  40                  45
tca tgt gaa acc tat gta aca tac att gct cag tct cca aat ttt ttg       254
Ser Cys Glu Thr Tyr Val Thr Tyr Ile Ala Gln Ser Pro Asn Phe Leu
             50                  55                  60 agt cta acc aac ata tcc aat ata ttt gac aca agc cct tta tcc att       302
Ser Leu Thr Asn Ile Ser Asn Ile Phe Asp Thr Ser Pro Leu Ser Ile
             65                  70                  75 gca aga gcc agt aac tta gag cct atg gat gac aag cta gtc aaa gac       350
Ala Arg Ala Ser Asn Leu Glu Pro Met Asp Asp Lys Leu Val Lys Asp
         80                  85                  90 caa gtc tta ctc gta cca gta acc tgt ggt tgc act gga aac cgc tct       398
Gln Val Leu Leu Val Pro Val Thr Cys Gly Cys Thr Gly Asn Arg Ser
95                 100                 105                 110 ttt gcc aat atc tcc tat gag atc aac caa ggt gat agc ttc tac ttt       446
Phe Ala Asn Ile Ser Tyr Glu Ile Asn Gln Gly Asp Ser Phe Tyr Phe
                115                 120                 125 gtt gca acc act tca tac gag aat ctc acg aat tgg cgt gca gtg atg       494
Val Ala Thr Thr Ser Tyr Glu Asn Leu Thr Asn Trp Arg Ala Val Met
            130                 135                 140 gat tta aac ccc gtt cta agt cca aat aag ttg cca ata gga atc caa       542
Asp Leu Asn Pro Val Leu Ser Pro Asn Lys Leu Pro Ile Gly Ile Gln
            145                 150                 155 gta gta ttt cct tta ttc tgc aag tgc cct tca aag aac cag ttg gac       590
Val Val Phe Pro Leu Phe Cys Lys Cys Pro Ser Lys Asn Gln Leu Asp
        160                 165                 170 aaa gag ata aag tac ctg att aca tac gtg tgg aag ccc ggt gac aat       638
Lys Glu Ile Lys Tyr Leu Ile Thr Tyr Val Trp Lys Pro Gly Asp Asn
175                 180                 185                 190 gtt tcc ctt gta agt gac aag ttt ggt gca tca cca gag gac ata atg       686
Val Ser Leu Val Ser Asp Lys Phe Gly Ala Ser Pro Glu Asp Ile Met
                195                 200                 205 agt gaa aac aac tat ggt cag aac ttt act gct gca aac aac ctt cca       734
Ser Glu Asn Asn Tyr Gly Gln Asn Phe Thr Ala Ala Asn Asn Leu Pro
            210                 215                 220 gtt ctg atc cca gtg aca cgc ttg cca gtt ctt gct cga tct cct tcg       782
Val Leu Ile Pro Val Thr Arg Leu Pro Val Leu Ala Arg Ser Pro Ser
            225                 230                 235 gac gga aga aaa ggc gga att cgt ctt ccg gtt ata att ggt att agc       830
Asp Gly Arg Lys Gly Gly Ile Arg Leu Pro Val Ile Ile Gly Ile Ser
        240                 245                 250 ttg gga tgc acg cta ctg gtt ctg gtt tta gca gtg tta ctg gtg tat       878
Leu Gly Cys Thr Leu Leu Val Leu Val Leu Ala Val Leu Leu Val Tyr
255                 260                 265                 270 gta tat tgt ctg aaa atg aag act ttg aat agg agt gct tca tcg gct       926
Val Tyr Cys Leu Lys Met Lys Thr Leu Asn Arg Ser Ala Ser Ser Ala
                275                 280                 285 gaa act gca gat aaa cta ctt tct gga gtt tca ggc tat gta agt aag       974
Glu Thr Ala Asp Lys Leu Leu Ser Gly Val Ser Gly Tyr Val Ser Lys
            290                 295                 300 cct acc atg tat gaa act gat gcg atc atg gaa gct aca atg aac ctc      1022
Pro Thr Met Tyr Glu Thr Asp Ala Ile Met Glu Ala Thr Met Asn Leu
            305                 310                 315 agt gag cag tgc aag att ggg gaa tca gtg tac aag gca aac ata gag      1070
Ser Glu Gln Cys Lys Ile Gly Glu Ser Val Tyr Lys Ala Asn Ile Glu
        320                 325                 330 ggt aag gtt ttg gca gta aaa aga ttc aag gaa gat gtc acg gaa gag      1118
Gly Lys Val Leu Ala Val Lys Arg Phe Lys Glu Asp Val Thr Glu Glu
335                 340                 345                 350 ctg aaa att ctg cag aag gtg aat cat ggg aat ctg gtg aaa cta atg      1166
Leu Lys Ile Leu Gln Lys Val Asn His Gly Asn Leu Val Lys Leu Met
```

```
                    355               360              365
ggt gtc tca tca gac aat gat gga aac tgt ttt gtg gtt tat gaa tac    1214
Gly Val Ser Ser Asp Asn Asp Gly Asn Cys Phe Val Val Tyr Glu Tyr
            370              375              380 gct gaa aat ggg tct ctt gat gag tgg cta ttc tcc aag tct tgt tca    1262
Ala Glu Asn Gly Ser Leu Asp Glu Trp Leu Phe Ser Lys Ser Cys Ser
        385              390              395 gac aca tca aac tca agg gca tcc ctt aca tgg tgt cag agg ata agc    1310
Asp Thr Ser Asn Ser Arg Ala Ser Leu Thr Trp Cys Gln Arg Ile Ser
    400              405              410 atg gca gtg gat gtt gcg atg ggt ttg cag tac atg cat gaa cat gct    1358
Met Ala Val Asp Val Ala Met Gly Leu Gln Tyr Met His Glu His Ala
415              420              425              430 tat cca aga ata gtc cac agg gac atc aca agc agt aat atc ctt ctt    1406
Tyr Pro Arg Ile Val His Arg Asp Ile Thr Ser Ser Asn Ile Leu Leu
                435              440              445 gac tcg aac ttt aag gcc aag ata gca aat ttc tcc atg gcc aga act    1454
Asp Ser Asn Phe Lys Ala Lys Ile Ala Asn Phe Ser Met Ala Arg Thr
            450              455              460 ttt acc aac ccc atg atg cca aag ata gat gtc ttt gca ttt ggg gtg    1502
Phe Thr Asn Pro Met Met Pro Lys Ile Asp Val Phe Ala Phe Gly Val
        465              470              475 gtt ctg att gag ttg ctt acc gga agg aaa gcc atg aca acc aag gaa    1550
Val Leu Ile Glu Leu Leu Thr Gly Arg Lys Ala Met Thr Thr Lys Glu
    480              485              490 aat ggt gag gtg gtc atg ctg tgg aag gac att tgg aag atc ttt gat    1598
Asn Gly Glu Val Val Met Leu Trp Lys Asp Ile Trp Lys Ile Phe Asp
495              500              505              510 caa gaa gag aat aga gag gag agg ctc aaa aaa tgg atg gat cct aag    1646
Gln Glu Glu Asn Arg Glu Glu Arg Leu Lys Lys Trp Met Asp Pro Lys
                515              520              525 tta gag agt tat tat cct ata gat tac gct ctc agc ttg gcc tcc ttg    1694
Leu Glu Ser Tyr Tyr Pro Ile Asp Tyr Ala Leu Ser Leu Ala Ser Leu
            530              535              540 gcg gtg aat tgt act gca gat aag tct ttg tcc aga cca acc att gca    1742
Ala Val Asn Cys Thr Ala Asp Lys Ser Leu Ser Arg Pro Thr Ile Ala
        545              550              555 gaa att gtc ctt agc ctc tcc ctt ctc act caa cca tct ccc gca aca    1790
Glu Ile Val Leu Ser Leu Ser Leu Leu Thr Gln Pro Ser Pro Ala Thr
    560              565              570 ttg gag aga tcc ttg act tct tct gga ttg gat gta gaa gct act caa    1838
Leu Glu Arg Ser Leu Thr Ser Ser Gly Leu Asp Val Glu Ala Thr Gln
575              580              585              590 att gtc act tcc ata gca gct cgt tgattgagtg aaggaaattt agtttctcaa    1892
Ile Val Thr Ser Ile Ala Ala Arg
                595 atccatgatg gtattttgtt tacatgatga ttattacatc tttagtcatt aatggttggc    1952 ttggtttggg ggagtgtgtt caaaatttcg ttttttttcca tccctgttat ttttttttaag    2012 tttggggtag agtcagcaaa aatggaagtt gcaattgacc tcagactaaa cttgcttatt    2072 tccctgtatc ttttttgtgt gataattgaa actgaattat atgatggatt atctgtta      2130

<210> SEQ ID NO 48
<211> LENGTH: 598
<212> TYPE: PRT
<213> ORGANISM: Glycine max

<400> SEQUENCE: 48

Met Ala Val Phe Phe Pro Phe Leu Pro Leu His Ser Gln Ile Leu Cys
1               5                   10                  15
```

```
Leu Val Ile Met Leu Phe Ser Thr Asn Ile Val Ala Gln Ser Gln Gln
                 20                  25                  30

Asp Asn Arg Thr Asn Phe Ser Cys Pro Ser Asp Ser Pro Pro Ser Cys
             35                  40                  45

Glu Thr Tyr Val Thr Tyr Ile Ala Gln Ser Pro Asn Phe Leu Ser Leu
     50                  55                  60

Thr Asn Ile Ser Asn Ile Phe Asp Thr Ser Pro Leu Ser Ile Ala Arg
 65                  70                  75                  80

Ala Ser Asn Leu Glu Pro Met Asp Asp Lys Leu Val Lys Asp Gln Val
                 85                  90                  95

Leu Leu Val Pro Val Thr Cys Gly Cys Thr Gly Asn Arg Ser Phe Ala
                100                 105                 110

Asn Ile Ser Tyr Glu Ile Asn Gln Gly Asp Ser Phe Tyr Phe Val Ala
                115                 120                 125

Thr Thr Ser Tyr Glu Asn Leu Thr Asn Trp Arg Ala Val Met Asp Leu
    130                 135                 140

Asn Pro Val Leu Ser Pro Asn Lys Leu Pro Ile Gly Ile Gln Val Val
145                 150                 155                 160

Phe Pro Leu Phe Cys Lys Cys Pro Ser Lys Asn Gln Leu Asp Lys Glu
                165                 170                 175

Ile Lys Tyr Leu Ile Thr Tyr Val Trp Lys Pro Gly Asp Asn Val Ser
                180                 185                 190

Leu Val Ser Asp Lys Phe Gly Ala Ser Pro Glu Asp Ile Met Ser Glu
                195                 200                 205

Asn Asn Tyr Gly Gln Asn Phe Thr Ala Ala Asn Asn Leu Pro Val Leu
                210                 215                 220

Ile Pro Val Thr Arg Leu Pro Val Leu Ala Arg Ser Pro Ser Asp Gly
225                 230                 235                 240

Arg Lys Gly Gly Ile Arg Leu Pro Val Ile Ile Gly Ile Ser Leu Gly
                245                 250                 255

Cys Thr Leu Leu Val Leu Val Leu Ala Val Leu Leu Val Tyr Val Tyr
                260                 265                 270

Cys Leu Lys Met Lys Thr Leu Asn Arg Ser Ala Ser Ser Ala Glu Thr
                275                 280                 285

Ala Asp Lys Leu Leu Ser Gly Val Ser Gly Tyr Val Ser Lys Pro Thr
                290                 295                 300

Met Tyr Glu Thr Asp Ala Ile Met Glu Ala Thr Met Asn Leu Ser Glu
305                 310                 315                 320

Gln Cys Lys Ile Gly Glu Ser Val Tyr Lys Ala Asn Ile Glu Gly Lys
                325                 330                 335

Val Leu Ala Val Lys Arg Phe Lys Glu Asp Val Thr Glu Glu Leu Lys
                340                 345                 350

Ile Leu Gln Lys Val Asn His Gly Asn Leu Val Lys Leu Met Gly Val
                355                 360                 365

Ser Ser Asp Asn Asp Gly Asn Cys Phe Val Val Tyr Glu Tyr Ala Glu
    370                 375                 380

Asn Gly Ser Leu Asp Glu Trp Leu Phe Ser Lys Ser Cys Ser Asp Thr
385                 390                 395                 400

Ser Asn Ser Arg Ala Ser Leu Thr Trp Cys Gln Arg Ile Ser Met Ala
                405                 410                 415

Val Asp Val Ala Met Gly Leu Gln Tyr Met His Glu His Ala Tyr Pro
                420                 425                 430

Arg Ile Val His Arg Asp Ile Thr Ser Ser Asn Ile Leu Leu Asp Ser
```

```
                  435                 440                 445
Asn Phe Lys Ala Lys Ile Ala Asn Phe Ser Met Ala Arg Thr Phe Thr
450                 455                 460

Asn Pro Met Met Pro Lys Ile Asp Val Phe Ala Phe Gly Val Val Leu
465                 470                 475                 480

Ile Glu Leu Leu Thr Gly Arg Lys Ala Met Thr Lys Glu Asn Gly
                485                 490                 495

Glu Val Val Met Leu Trp Lys Asp Ile Trp Lys Ile Phe Asp Gln Glu
                500                 505                 510

Glu Asn Arg Glu Glu Arg Leu Lys Lys Trp Met Asp Pro Lys Leu Glu
                515                 520                 525

Ser Tyr Tyr Pro Ile Asp Tyr Ala Leu Ser Leu Ala Ser Leu Ala Val
                530                 535                 540

Asn Cys Thr Ala Asp Lys Ser Leu Ser Arg Pro Thr Ile Ala Glu Ile
545                 550                 555                 560

Val Leu Ser Leu Ser Leu Leu Thr Gln Pro Ser Pro Ala Thr Leu Glu
                565                 570                 575

Arg Ser Leu Thr Ser Ser Gly Leu Asp Val Glu Ala Thr Gln Ile Val
                580                 585                 590

Thr Ser Ile Ala Ala Arg
        595

<210> SEQ ID NO 49
<211> LENGTH: 22
<212> TYPE: DNA
<213> ORGANISM: Lotus japonicus
<220> FEATURE:
<221> NAME/KEY: misc_feature
<222> LOCATION: (1)..(22)
<223> OTHER INFORMATION: NPR5 extracellular domain coding sequence
      amplification primer

<400> SEQUENCE: 49
taattatcag agtaagtgtg ac                                                 22

<210> SEQ ID NO 50
<211> LENGTH: 19
<212> TYPE: DNA
<213> ORGANISM: Lotus japonicus
<220> FEATURE:
<221> NAME/KEY: misc_feature
<222> LOCATION: (1)..(19)
<223> OTHER INFORMATION: NPR5 extracellular domain coding sequence
      amplification primer

<400> SEQUENCE: 50
agttacccac ctgtggtac                                                     19

<210> SEQ ID NO 51
<211> LENGTH: 2160
<212> TYPE: DNA
<213> ORGANISM: Pisum sativum
<220> FEATURE:
<221> NAME/KEY: 5'UTR
<222> LOCATION: (1)..(65)
<220> FEATURE:
<221> NAME/KEY: CDS
<222> LOCATION: (66)..(1931)
<220> FEATURE:
<221> NAME/KEY: 3'UTR
<222> LOCATION: (1932)..(2160)

<400> SEQUENCE: 51 tttttctgc ttcttccttt tcttcaggag ccatttgat ttgctctctt tcttattgac         60
```

-continued

```
caaat atg aaa cta aaa aat ggc tta ctc ttg ttc ttt cta ttt gtg gag      110
      Met Lys Leu Lys Asn Gly Leu Leu Leu Phe Phe Leu Phe Val Glu
      1               5                   10                  15 tgt gct ttt ttc aaa gtg gat tca aag tgt gtg aaa ggg tgt gat cta        158
Cys Ala Phe Phe Lys Val Asp Ser Lys Cys Val Lys Gly Cys Asp Leu
                20                  25                  30 gct tta gct tct tac tat gta atg cct tta gtt gaa ctc cca act ata        206
Ala Leu Ala Ser Tyr Tyr Val Met Pro Leu Val Glu Leu Pro Thr Ile
            35                  40                  45 aaa aac tat atg caa tca aag ata gtt acc aac tct tct gat gtt tta        254
Lys Asn Tyr Met Gln Ser Lys Ile Val Thr Asn Ser Ser Asp Val Leu
        50                  55                  60 aat agt tac aac aaa gtc tta gta acc aat cat ggt aat att ttt tcc        302
Asn Ser Tyr Asn Lys Val Leu Val Thr Asn His Gly Asn Ile Phe Ser
    65                  70                  75 tat ttt aga atc aac att cca ttc cca tgt gaa tgt att gga ggt gag        350
Tyr Phe Arg Ile Asn Ile Pro Phe Pro Cys Glu Cys Ile Gly Gly Glu
80                  85                  90                  95 ttc tta gga cat gtg ttt gaa tat aca aca aag aaa gga gat act tat        398
Phe Leu Gly His Val Phe Glu Tyr Thr Thr Lys Lys Gly Asp Thr Tyr
                100                 105                 110 gat ttg att gca aat aat tat tat gta agt ttg act agt gtt gag ctt        446
Asp Leu Ile Ala Asn Asn Tyr Tyr Val Ser Leu Thr Ser Val Glu Leu
            115                 120                 125 ttg aag aag ttt aac agc tat gat cca aat cat ata cct gct aag gct        494
Leu Lys Lys Phe Asn Ser Tyr Asp Pro Asn His Ile Pro Ala Lys Ala
        130                 135                 140 aag gtt aat gtt act gtg aat tgt tct tgt ggg aat agc cag att tca        542
Lys Val Asn Val Thr Val Asn Cys Ser Cys Gly Asn Ser Gln Ile Ser
    145                 150                 155 aaa gat tat ggc ttg ttt gtt act tat ccg tta agg tct acg gat tct        590
Lys Asp Tyr Gly Leu Phe Val Thr Tyr Pro Leu Arg Ser Thr Asp Ser
160                 165                 170                 175 ctt gag aag att gcg aac gag tcg aaa ctt gat gaa ggg ttg ata cag        638
Leu Glu Lys Ile Ala Asn Glu Ser Lys Leu Asp Glu Gly Leu Ile Gln
                180                 185                 190 aat ttc aac cct gat gtc aat ttc agt aga gga agt ggg ata gtg ttc        686
Asn Phe Asn Pro Asp Val Asn Phe Ser Arg Gly Ser Gly Ile Val Phe
            195                 200                 205 att cca gga aga gat aaa aat gga gaa tat gtt cct ttg tat cct aaa        734
Ile Pro Gly Arg Asp Lys Asn Gly Glu Tyr Val Pro Leu Tyr Pro Lys
        210                 215                 220 aca ggt gtt ggt aag ggt gta gct att ggt ata tct ata gca gga gta        782
Thr Gly Val Gly Lys Gly Val Ala Ile Gly Ile Ser Ile Ala Gly Val
    225                 230                 235 ttt gcg gtt ctg tta ttt gtt atc tgt ata tat gtc aaa tac ttc cag        830
Phe Ala Val Leu Leu Phe Val Ile Cys Ile Tyr Val Lys Tyr Phe Gln
240                 245                 250                 255 aaa aag gaa gaa gag aaa act ata ctg ccc caa gtt tct aag gcg ctt        878
Lys Lys Glu Glu Glu Lys Thr Ile Leu Pro Gln Val Ser Lys Ala Leu
                260                 265                 270 tcg act caa gat ggt aat gcc tcg agt agt gga gaa tat gaa act tca        926
Ser Thr Gln Asp Gly Asn Ala Ser Ser Ser Gly Glu Tyr Glu Thr Ser
            275                 280                 285 gga tct agt ggg cat ggt act ggt agt gct gca ggc ctc aca gga atc        974
Gly Ser Ser Gly His Gly Thr Gly Ser Ala Ala Gly Leu Thr Gly Ile
        290                 295                 300 atg gtg gca aag tca act gag ttt tca tat caa gag cta gcc aag gct       1022
Met Val Ala Lys Ser Thr Glu Phe Ser Tyr Gln Glu Leu Ala Lys Ala
    305                 310                 315
```

```
aca gat aac ttt agt ttg gat aat aaa atc ggt caa ggt gga ttt gga      1070
Thr Asp Asn Phe Ser Leu Asp Asn Lys Ile Gly Gln Gly Gly Phe Gly
320                 325                 330                 335 gct gtc tat tat gca gaa ctc aga ggc gag aaa aca gca atc aag aag      1118
Ala Val Tyr Tyr Ala Glu Leu Arg Gly Glu Lys Thr Ala Ile Lys Lys
                340                 345                 350 atg aat gtg caa gca tca tca gaa ttt ctg tgt gag ttg aag gtc tta      1166
Met Asn Val Gln Ala Ser Ser Glu Phe Leu Cys Glu Leu Lys Val Leu
            355                 360                 365 acg cac gtt cat cat ttg aat ctg gtg agg ttg att gga tat tgc gtt      1214
Thr His Val His His Leu Asn Leu Val Arg Leu Ile Gly Tyr Cys Val
        370                 375                 380 gag ggg tcg ctt ttc ctt gtc tat gaa cat att gac aat gga aac ttg      1262
Glu Gly Ser Leu Phe Leu Val Tyr Glu His Ile Asp Asn Gly Asn Leu
385                 390                 395 ggt caa tat ttg cat ggt aaa gat aaa gag cca tta cca tgg tct agt      1310
Gly Gln Tyr Leu His Gly Lys Asp Lys Glu Pro Leu Pro Trp Ser Ser
400                 405                 410                 415 aga gtc caa att gct cta gat tca gca cga ggc ctt gaa tac att cat      1358
Arg Val Gln Ile Ala Leu Asp Ser Ala Arg Gly Leu Glu Tyr Ile His
                420                 425                 430 gaa cat acc gtg cct gtg tat atc cat cgc gat gta aaa tca gca aac      1406
Glu His Thr Val Pro Val Tyr Ile His Arg Asp Val Lys Ser Ala Asn
            435                 440                 445 ata ttg ata gac aaa aac ttg cgc gga aag gtt gca gat ttt ggc ttg      1454
Ile Leu Ile Asp Lys Asn Leu Arg Gly Lys Val Ala Asp Phe Gly Leu
        450                 455                 460 acc aaa ctt att gaa gtt gga aat tcc aca ctt cac act cgt ctt gtt      1502
Thr Lys Leu Ile Glu Val Gly Asn Ser Thr Leu His Thr Arg Leu Val
465                 470                 475 gga act ttt gga tac atg cca cca gaa tat gct caa tat ggt gac gtt      1550
Gly Thr Phe Gly Tyr Met Pro Pro Glu Tyr Ala Gln Tyr Gly Asp Val
480                 485                 490                 495 tct ccg aaa ata gac gta tat gct ttt gga gtt gtt ctt tat gaa ctg      1598
Ser Pro Lys Ile Asp Val Tyr Ala Phe Gly Val Val Leu Tyr Glu Leu
                500                 505                 510 ata tct gca aag aat gct gtt ctg aag aca ggt gaa gaa tct gtt gct      1646
Ile Ser Ala Lys Asn Ala Val Leu Lys Thr Gly Glu Glu Ser Val Ala
            515                 520                 525 gaa tca aag ggt ctt gta gcc ttg ttt gaa aaa gca ctt aat cag att      1694
Glu Ser Lys Gly Leu Val Ala Leu Phe Glu Lys Ala Leu Asn Gln Ile
        530                 535                 540 gat cct tca gaa gct ctt cgc aaa ttg gtg gat cct agg ctt aaa gaa      1742
Asp Pro Ser Glu Ala Leu Arg Lys Leu Val Asp Pro Arg Leu Lys Glu
545                 550                 555 aac tat cca att gat tct gtt tta aag atg gct caa ctt ggg aga gca      1790
Asn Tyr Pro Ile Asp Ser Val Leu Lys Met Ala Gln Leu Gly Arg Ala
560                 565                 570                 575 tgt aca aga gat aat cca cta cta cgc cca agt atg aga tct tta gtt      1838
Cys Thr Arg Asp Asn Pro Leu Leu Arg Pro Ser Met Arg Ser Leu Val
                580                 585                 590 gtt gat ctt atg aca ctg tca tca cca ttt gaa gat tgt gat gat gac      1886
Val Asp Leu Met Thr Leu Ser Ser Pro Phe Glu Asp Cys Asp Asp Asp
            595                 600                 605 act tcc tat gaa aat caa act ctc ata aat cta ttg tca gtg aga           1931
Thr Ser Tyr Glu Asn Gln Thr Leu Ile Asn Leu Leu Ser Val Arg
        610                 615                 620 tgaaggttct tgtgccaga ttgaatgatg tttgttaaaa ctgaactagt tgggaagttt      1991
tttactttgt gttcaaagtt tatttcccaa aatgttcaaa aggtcctaga tttcaaaaag      2051
```

```
acatcctgta attatttta gtgaagttgt aacactgaag tacaatttgt attatgatgt    2111
gaaaacttta ttttgcttt caaaatgtac ataagataag attctaaac              2160
```

<210> SEQ ID NO 52
<211> LENGTH: 622
<212> TYPE: PRT
<213> ORGANISM: Pisum sativum

<400> SEQUENCE: 52

```
Met Lys Leu Lys Asn Gly Leu Leu Phe Leu Phe Val Glu Cys
1               5                   10                  15

Ala Phe Phe Lys Val Asp Ser Lys Cys Val Lys Gly Cys Asp Leu Ala
            20                  25                  30

Leu Ala Ser Tyr Tyr Val Met Pro Leu Val Glu Leu Pro Thr Ile Lys
        35                  40                  45

Asn Tyr Met Gln Ser Lys Ile Val Thr Asn Ser Ser Asp Val Leu Asn
    50                  55                  60

Ser Tyr Asn Lys Val Leu Val Thr Asn His Gly Asn Ile Phe Ser Tyr
65                  70                  75                  80

Phe Arg Ile Asn Ile Pro Phe Pro Cys Glu Cys Ile Gly Gly Glu Phe
                85                  90                  95

Leu Gly His Val Phe Glu Tyr Thr Thr Lys Lys Gly Asp Thr Tyr Asp
            100                 105                 110

Leu Ile Ala Asn Asn Tyr Tyr Val Ser Leu Thr Ser Val Glu Leu Leu
        115                 120                 125

Lys Lys Phe Asn Ser Tyr Asp Pro Asn His Ile Pro Ala Lys Ala Lys
    130                 135                 140

Val Asn Val Thr Val Asn Cys Ser Cys Gly Asn Ser Gln Ile Ser Lys
145                 150                 155                 160

Asp Tyr Gly Leu Phe Val Thr Tyr Pro Leu Arg Ser Thr Asp Ser Leu
                165                 170                 175

Glu Lys Ile Ala Asn Glu Ser Lys Leu Asp Glu Gly Leu Ile Gln Asn
            180                 185                 190

Phe Asn Pro Asp Val Asn Phe Ser Arg Gly Ser Gly Ile Val Phe Ile
        195                 200                 205

Pro Gly Arg Asp Lys Asn Gly Glu Tyr Val Pro Leu Tyr Pro Lys Thr
    210                 215                 220

Gly Val Gly Lys Gly Val Ala Ile Gly Ile Ser Ile Ala Gly Val Phe
225                 230                 235                 240

Ala Val Leu Leu Phe Val Ile Cys Ile Tyr Val Lys Tyr Phe Gln Lys
                245                 250                 255

Lys Glu Glu Lys Thr Ile Leu Pro Gln Val Ser Lys Ala Leu Ser
            260                 265                 270

Thr Gln Asp Gly Asn Ala Ser Ser Gly Glu Tyr Glu Thr Ser Gly
        275                 280                 285

Ser Ser Gly His Gly Thr Gly Ser Ala Ala Gly Leu Thr Gly Ile Met
    290                 295                 300

Val Ala Lys Ser Thr Glu Phe Ser Tyr Gln Glu Leu Ala Lys Ala Thr
305                 310                 315                 320

Asp Asn Phe Ser Leu Asp Asn Lys Ile Gly Gln Gly Gly Phe Gly Ala
                325                 330                 335

Val Tyr Tyr Ala Glu Leu Arg Gly Glu Lys Thr Ala Ile Lys Lys Met
            340                 345                 350

Asn Val Gln Ala Ser Ser Glu Phe Leu Cys Glu Leu Lys Val Leu Thr
```

```
                     355                 360                 365
His Val His His Leu Asn Leu Val Arg Leu Ile Gly Tyr Cys Val Glu
        370                 375                 380

Gly Ser Leu Phe Leu Val Tyr Glu His Ile Asp Asn Gly Asn Leu Gly
385                 390                 395                 400

Gln Tyr Leu His Gly Lys Asp Lys Glu Pro Leu Pro Trp Ser Ser Arg
                405                 410                 415

Val Gln Ile Ala Leu Asp Ser Ala Arg Gly Leu Glu Tyr Ile His Glu
            420                 425                 430

His Thr Val Pro Val Tyr Ile His Arg Asp Val Lys Ser Ala Asn Ile
        435                 440                 445

Leu Ile Asp Lys Asn Leu Arg Gly Lys Val Ala Asp Phe Gly Leu Thr
    450                 455                 460

Lys Leu Ile Glu Val Gly Asn Ser Thr Leu His Thr Arg Leu Val Gly
465                 470                 475                 480

Thr Phe Gly Tyr Met Pro Pro Glu Tyr Ala Gln Tyr Gly Asp Val Ser
                485                 490                 495

Pro Lys Ile Asp Val Tyr Ala Phe Gly Val Val Leu Tyr Glu Leu Ile
            500                 505                 510

Ser Ala Lys Asn Ala Val Leu Lys Thr Gly Glu Glu Ser Val Ala Glu
        515                 520                 525

Ser Lys Gly Leu Val Ala Leu Phe Glu Lys Ala Leu Asn Gln Ile Asp
    530                 535                 540

Pro Ser Glu Ala Leu Arg Lys Leu Val Asp Pro Arg Leu Lys Glu Asn
545                 550                 555                 560

Tyr Pro Ile Asp Ser Val Leu Lys Met Ala Gln Leu Gly Arg Ala Cys
                565                 570                 575

Thr Arg Asp Asn Pro Leu Leu Arg Pro Ser Met Arg Ser Leu Val Val
            580                 585                 590

Asp Leu Met Thr Leu Ser Ser Pro Phe Glu Asp Cys Asp Asp Thr
        595                 600                 605

Ser Tyr Glu Asn Gln Thr Leu Ile Asn Leu Leu Ser Val Arg
    610                 615                 620

<210> SEQ ID NO 53
<211> LENGTH: 2217
<212> TYPE: DNA
<213> ORGANISM: Pisum sativum
<220> FEATURE:
<221> NAME/KEY: 5'UTR
<222> LOCATION: (1)..(140)
<220> FEATURE:
<221> NAME/KEY: CDS
<222> LOCATION: (141)..(1991)
<220> FEATURE:
<221> NAME/KEY: 3'UTR
<222> LOCATION: (1992)..(2217)

<400> SEQUENCE: 53
attcggcacg agattttcaa gaaatgaatt ttgtactaca tattaatcat tcgttgctga      60
tttgagttaa tttctttttc tgcttcttgc tttccttcgg cagccatttt gtgattttt     120 ctctttccct tattgattca atg aaa ctc aaa aat ggg tta ctg ctg ttc ttt     173
                        Met Lys Leu Lys Asn Gly Leu Leu Leu Phe Phe
                          1               5                      10 atg ttt ctg gat tgt att ttt ttc aaa gtg gaa tcc aag tgt gta ata      221
Met Phe Leu Asp Cys Ile Phe Phe Lys Val Glu Ser Lys Cys Val Ile
         15                  20                  25 ggg tgt gat ata gct tta gct tcc tac tat gta atg cct tta gtt caa      269
```

-continued

```
            Gly Cys Asp Ile Ala Leu Ala Ser Tyr Tyr Val Met Pro Leu Val Gln
                    30                  35                  40 ctc tcc aat ata aca acc ttt atg caa tca aag ctt gtt acc aat tct      317
Leu Ser Asn Ile Thr Thr Phe Met Gln Ser Lys Leu Val Thr Asn Ser
    45                  50                  55 ttt gag gtt ata gta agg tac aac aga gac att gtg ttc agt aat gat      365
Phe Glu Val Ile Val Arg Tyr Asn Arg Asp Ile Val Phe Ser Asn Asp
60                  65                  70                  75 aat ctt ttt tcc tat ttt aga gtc aac att cca ttc cca tgt gaa tgt      413
Asn Leu Phe Ser Tyr Phe Arg Val Asn Ile Pro Phe Pro Cys Glu Cys
                    80                  85                  90 att gga ggt gaa ttt ctt ggg cat gtg ttt gaa tac act gca aat gaa      461
Ile Gly Gly Glu Phe Leu Gly His Val Phe Glu Tyr Thr Ala Asn Glu
                95                  100                 105 ggc gat act tat gat tta att gca aat acc tat tat gca agc tta aca      509
Gly Asp Thr Tyr Asp Leu Ile Ala Asn Thr Tyr Tyr Ala Ser Leu Thr
            110                 115                 120 act gtt gag gtt ttg aaa aag tac aac agc tat gat cca aat cat ata      557
Thr Val Glu Val Leu Lys Lys Tyr Asn Ser Tyr Asp Pro Asn His Ile
        125                 130                 135 cct gtc aaa gct aag gtt aat gtc act gtt aat tgt tct tgt ggg aac      605
Pro Val Lys Ala Lys Val Asn Val Thr Val Asn Cys Ser Cys Gly Asn
140                 145                 150                 155 agc cag att tca aaa gac tat ggg cta ttt atc acc tat cca ctt agg      653
Ser Gln Ile Ser Lys Asp Tyr Gly Leu Phe Ile Thr Tyr Pro Leu Arg
                    160                 165                 170 cct agg gat act ctt gag aag att gca aga cat tct aat ctt gat gaa      701
Pro Arg Asp Thr Leu Glu Lys Ile Ala Arg His Ser Asn Leu Asp Glu
                175                 180                 185 gga gta ata caa agt tac aat ttg ggt gtc aat ttc agc aaa ggc agc      749
Gly Val Ile Gln Ser Tyr Asn Leu Gly Val Asn Phe Ser Lys Gly Ser
            190                 195                 200 ggg gta gtg ttc ttt ccc gga aga gat aaa aat gga gaa tat gtt cct      797
Gly Val Val Phe Phe Pro Gly Arg Asp Lys Asn Gly Glu Tyr Val Pro
        205                 210                 215 tta tat cct aga aca ggt ctt ggt aag ggt gca gct gct ggt ata tct      845
Leu Tyr Pro Arg Thr Gly Leu Gly Lys Gly Ala Ala Ala Gly Ile Ser
220                 225                 230                 235 ata gct gga ata ttt gcg ctt ctg tta ttt gtt atc tgc ata tat atc      893
Ile Ala Gly Ile Phe Ala Leu Leu Leu Phe Val Ile Cys Ile Tyr Ile
                    240                 245                 250 aaa tac ttc caa aag aag gaa gaa gag aaa act aaa ctg cca caa gtt      941
Lys Tyr Phe Gln Lys Lys Glu Glu Glu Lys Thr Lys Leu Pro Gln Val
                255                 260                 265 tct acg gcg ctt tca gct caa gat gcc tcg ggt agt gga gag tac gaa      989
Ser Thr Ala Leu Ser Ala Gln Asp Ala Ser Gly Ser Gly Glu Tyr Glu
            270                 275                 280 act tcg gga tcc agt ggg cat ggt acc ggt agt act gct ggc ctt aca     1037
Thr Ser Gly Ser Ser Gly His Gly Thr Gly Ser Thr Ala Gly Leu Thr
        285                 290                 295 gga att atg gtg gca aag tca act gag ttt tca tat caa gaa cta gcc     1085
Gly Ile Met Val Ala Lys Ser Thr Glu Phe Ser Tyr Gln Glu Leu Ala
300                 305                 310                 315 aag gct aca aat aac ttc agc tta gat aat aaa att ggt caa ggt gga     1133
Lys Ala Thr Asn Asn Phe Ser Leu Asp Asn Lys Ile Gly Gln Gly Gly
                    320                 325                 330 ttt gga gct gtc tat tat gca gta ctc aga ggc gag aaa aca gca att     1181
Phe Gly Ala Val Tyr Tyr Ala Val Leu Arg Gly Glu Lys Thr Ala Ile
                335                 340                 345 aag aag atg gat gta caa gcg tca aca gaa ttc ctt tgc gag ttg caa     1229
```

```
                Lys Lys Met Asp Val Gln Ala Ser Thr Glu Phe Leu Cys Glu Leu Gln
                    350                 355                 360 gtc tta aca cat gtt cat cac ttg aat ctg gtg agg ttg att gga tat        1277
Val Leu Thr His Val His His Leu Asn Leu Val Arg Leu Ile Gly Tyr
365                 370                 375 tgt gtt gag gga tca ctt ttc ctt gta tat gaa cat att gac aat gga        1325
Cys Val Glu Gly Ser Leu Phe Leu Val Tyr Glu His Ile Asp Asn Gly
380                 385                 390                 395 aac ttg ggt caa tat ttg cac ggt ata gat aaa gcg cca tta cca tgg        1373
Asn Leu Gly Gln Tyr Leu His Gly Ile Asp Lys Ala Pro Leu Pro Trp
                400                 405                 410 tca agt agg gtg caa att gct cta gat tcc gca aga ggc ctt gaa tac        1421
Ser Ser Arg Val Gln Ile Ala Leu Asp Ser Ala Arg Gly Leu Glu Tyr
            415                 420                 425 att cat gaa cac act gta cct gtg tat atc cat cgt gat gta aaa tca        1469
Ile His Glu His Thr Val Pro Val Tyr Ile His Arg Asp Val Lys Ser
        430                 435                 440 gcg aat ata tta ata gac aaa aac ttg cac gga aag gtt gca gat ttt        1517
Ala Asn Ile Leu Ile Asp Lys Asn Leu His Gly Lys Val Ala Asp Phe
445                 450                 455 ggc ttg acc aaa ctt att gaa gtt gga aac tcc aca ctt cac act cgt        1565
Gly Leu Thr Lys Leu Ile Glu Val Gly Asn Ser Thr Leu His Thr Arg
460                 465                 470                 475 cta gtg gga aca ttt gga tac atg cca cca gaa tat gct caa tat ggc        1613
Leu Val Gly Thr Phe Gly Tyr Met Pro Pro Glu Tyr Ala Gln Tyr Gly
                480                 485                 490 gat gtt tct cca aaa ata gat gta tat gct ttt gga gtt gtt ctt tat        1661
Asp Val Ser Pro Lys Ile Asp Val Tyr Ala Phe Gly Val Val Leu Tyr
            495                 500                 505 gag ctt att tct gca aag aat gct att ctg aag aca ggt gaa tct gca        1709
Glu Leu Ile Ser Ala Lys Asn Ala Ile Leu Lys Thr Gly Glu Ser Ala
        510                 515                 520 gtc gaa tca aag ggt ctt gta gca ttg ttt gaa gaa gca ctt aat cag        1757
Val Glu Ser Lys Gly Leu Val Ala Leu Phe Glu Glu Ala Leu Asn Gln
525                 530                 535 atc gat cct tta gaa gct ctt cgc aaa ttg gtg gat cct agg ctt aaa        1805
Ile Asp Pro Leu Glu Ala Leu Arg Lys Leu Val Asp Pro Arg Leu Lys
540                 545                 550                 555 gaa aac tat cca att gat tct gtt tta aag atg gct caa ctt ggg aga        1853
Glu Asn Tyr Pro Ile Asp Ser Val Leu Lys Met Ala Gln Leu Gly Arg
                560                 565                 570 gca tgt aca aga gac aat cca cta cta cgc cca agt atg aga tct tta        1901
Ala Cys Thr Arg Asp Asn Pro Leu Leu Arg Pro Ser Met Arg Ser Leu
            575                 580                 585 gtc gtt gct ctt atg aca ctc tta tca cat act gat gat gat gac act        1949
Val Val Ala Leu Met Thr Leu Leu Ser His Thr Asp Asp Asp Asp Thr
        590                 595                 600 ttc tat gaa aat caa tct ctc aca aat cta tta tca gtg aga                1991
Phe Tyr Glu Asn Gln Ser Leu Thr Asn Leu Leu Ser Val Arg
605                 610                 615 tgaaggcttt gtgtgccaaa ttgaatgatg tttgtgaaaa cttttagaag catacagcaa      2051
aatgtttgta ctctgaacat aatattgagg ttaggaagtt ttgatcttgt gttcaaattt      2111
tatttcccaa aatagtcaaa aagtcctaga tccaagaag acatcctgta attattttta       2171
gtgacgctgt aacactaaag tacagtttat atataacatt ttaaaa                     2217

<210> SEQ ID NO 54
<211> LENGTH: 617
<212> TYPE: PRT
<213> ORGANISM: Pisum sativum
```

<400> SEQUENCE: 54

```
Met Lys Leu Lys Asn Gly Leu Leu Leu Phe Phe Met Phe Leu Asp Cys
1               5                   10                  15
Ile Phe Phe Lys Val Glu Ser Lys Cys Val Ile Gly Cys Asp Ile Ala
            20                  25                  30
Leu Ala Ser Tyr Tyr Val Met Pro Leu Val Gln Leu Ser Asn Ile Thr
        35                  40                  45
Thr Phe Met Gln Ser Lys Leu Val Thr Asn Ser Phe Glu Val Ile Val
    50                  55                  60
Arg Tyr Asn Arg Asp Ile Val Phe Ser Asn Asp Asn Leu Phe Ser Tyr
65                  70                  75                  80
Phe Arg Val Asn Ile Pro Phe Pro Cys Glu Cys Ile Gly Gly Glu Phe
                85                  90                  95
Leu Gly His Val Phe Glu Tyr Thr Ala Asn Glu Gly Asp Thr Tyr Asp
            100                 105                 110
Leu Ile Ala Asn Thr Tyr Tyr Ala Ser Leu Thr Thr Val Glu Val Leu
        115                 120                 125
Lys Lys Tyr Asn Ser Tyr Asp Pro Asn His Ile Pro Val Lys Ala Lys
    130                 135                 140
Val Asn Val Thr Val Asn Cys Ser Cys Gly Asn Ser Gln Ile Ser Lys
145                 150                 155                 160
Asp Tyr Gly Leu Phe Ile Thr Tyr Pro Leu Arg Pro Arg Asp Thr Leu
                165                 170                 175
Glu Lys Ile Ala Arg His Ser Asn Leu Asp Glu Gly Val Ile Gln Ser
            180                 185                 190
Tyr Asn Leu Gly Val Asn Phe Ser Lys Gly Ser Gly Val Val Phe Phe
        195                 200                 205
Pro Gly Arg Asp Lys Asn Gly Glu Tyr Val Pro Leu Tyr Pro Arg Thr
    210                 215                 220
Gly Leu Gly Lys Gly Ala Ala Gly Ile Ser Ile Ala Gly Ile Phe
225                 230                 235                 240
Ala Leu Leu Leu Phe Val Ile Cys Ile Tyr Ile Lys Tyr Phe Gln Lys
                245                 250                 255
Lys Glu Glu Glu Lys Thr Lys Leu Pro Gln Val Ser Thr Ala Leu Ser
            260                 265                 270
Ala Gln Asp Ala Ser Gly Ser Gly Glu Tyr Glu Thr Ser Gly Ser Ser
        275                 280                 285
Gly His Gly Thr Gly Ser Thr Ala Gly Leu Thr Gly Ile Met Val Ala
    290                 295                 300
Lys Ser Thr Glu Phe Ser Tyr Gln Glu Leu Ala Lys Ala Thr Asn Asn
305                 310                 315                 320
Phe Ser Leu Asp Asn Lys Ile Gly Gln Gly Gly Phe Gly Ala Val Tyr
                325                 330                 335
Tyr Ala Val Leu Arg Gly Glu Lys Thr Ala Ile Lys Lys Met Asp Val
            340                 345                 350
Gln Ala Ser Thr Glu Phe Leu Cys Glu Leu Gln Val Leu Thr His Val
        355                 360                 365
His His Leu Asn Leu Val Arg Leu Ile Gly Tyr Cys Val Glu Gly Ser
    370                 375                 380
Leu Phe Leu Val Tyr Glu His Ile Asp Asn Gly Asn Leu Gly Gln Tyr
385                 390                 395                 400
Leu His Gly Ile Asp Lys Ala Pro Leu Pro Trp Ser Ser Arg Val Gln
                405                 410                 415
```

```
Ile Ala Leu Asp Ser Ala Arg Gly Leu Glu Tyr Ile His Glu His Thr
            420                 425                 430
Val Pro Val Tyr Ile His Arg Asp Val Lys Ser Ala Asn Ile Leu Ile
            435                 440                 445
Asp Lys Asn Leu His Gly Lys Val Ala Asp Phe Gly Leu Thr Lys Leu
            450                 455                 460
Ile Glu Val Gly Asn Ser Thr Leu His Thr Arg Leu Val Gly Thr Phe
465                 470                 475                 480
Gly Tyr Met Pro Pro Glu Tyr Ala Gln Tyr Gly Asp Val Ser Pro Lys
                    485                 490                 495
Ile Asp Val Tyr Ala Phe Gly Val Val Leu Tyr Glu Leu Ile Ser Ala
            500                 505                 510
Lys Asn Ala Ile Leu Lys Thr Gly Glu Ser Ala Val Glu Ser Lys Gly
            515                 520                 525
Leu Val Ala Leu Phe Glu Glu Ala Leu Asn Gln Ile Asp Pro Leu Glu
            530                 535                 540
Ala Leu Arg Lys Leu Val Asp Pro Arg Leu Lys Glu Asn Tyr Pro Ile
545                 550                 555                 560
Asp Ser Val Leu Lys Met Ala Gln Leu Gly Arg Ala Cys Thr Arg Asp
                    565                 570                 575
Asn Pro Leu Leu Arg Pro Ser Met Arg Ser Leu Val Val Ala Leu Met
            580                 585                 590
Thr Leu Leu Ser His Thr Asp Asp Asp Thr Phe Tyr Glu Asn Gln
            595                 600                 605
Ser Leu Thr Asn Leu Leu Ser Val Arg
            610                 615

<210> SEQ ID NO 55
<211> LENGTH: 80
<212> TYPE: DNA
<213> ORGANISM: Phaseolus vulgaris

<400> SEQUENCE: 55
cacaggacat attgagtgaa acaactatg gtcaaaattt cactgccgca agcaaccttc    60
cagttttgat cccagttaca                                              80

<210> SEQ ID NO 56
<211> LENGTH: 80
<212> TYPE: DNA
<213> ORGANISM: Phaseolus vulgaris

<400> SEQUENCE: 56
cacaggacat attgagtgaa acaactatg gtcaaaactt cactgccgca agcaaccttc    60
cagttttgat cccagttaca                                              80

<210> SEQ ID NO 57
<211> LENGTH: 31
<212> TYPE: DNA
<213> ORGANISM: Lotus japonicus

<400> SEQUENCE: 57
ttttgctgca gcaagtcaga ctgttagagg a                                 31

<210> SEQ ID NO 58
<211> LENGTH: 31
<212> TYPE: DNA
<213> ORGANISM: Lotus japonicus
```

-continued

```
<400> SEQUENCE: 58
ttttgctgca acaagtcgga ctgttagagg a                              31

<210> SEQ ID NO 59
<211> LENGTH: 30
<212> TYPE: DNA
<213> ORGANISM: Lotus japonicus

<400> SEQUENCE: 59
ttggaagttc tttttattag gttaatttta                                30

<210> SEQ ID NO 60
<211> LENGTH: 27
<212> TYPE: DNA
<213> ORGANISM: Lotus japonicus

<400> SEQUENCE: 60
ttggaagttc tttttaggtt aatttta                                   27

<210> SEQ ID NO 61
<211> LENGTH: 30
<212> TYPE: DNA
<213> ORGANISM: Lotus japonicus

<400> SEQUENCE: 61
cattccagaa gaaaataaga tataattatg                                30

<210> SEQ ID NO 62
<211> LENGTH: 29
<212> TYPE: DNA
<213> ORGANISM: Lotus japonicus

<400> SEQUENCE: 62
cattccagaa gaaataagat ataattatg                                 29
```

NOD-FACTOR PERCEPTION

This application is the National Stage application of PCT/DK2004/000478 filed on Jul. 2, 2004, which claims benefit to Danish Application No. PA 2003 01010 filed on Jul. 3, 2003, and U.S. provisional Application No. 60/484,923, filed July 3, 2003 (now expired), which application(s) are incorporated herein by reference.

FIELD OF THE INVENTION

The invention relates to a novel Nod-factor binding element and component polypeptides that are useful in enhancing Nod-factor binding in nodulating plants and inducing nodulation in non-nodulating plants. More specifically, the invention relates to Nod-factor binding proteins and their respective genomic and mRNA nucleic acid sequences.

BACKGROUND OF THE INVENTION

The growth of agricultural crops is almost always limited by the availability of nitrogen, and at least 50% of global needs are met by the application of synthetic fertilisers in the form of ammonia, nitrate or urea. Apart from recycling of crop residues and animal manure, and atmospheric deposition, the other most important source of nitrogen for agriculture comes from biological nitrogen fixation.

A small percentage of prokaryots, the diazotrophs, produce nitrogenases and are capable of nitrogen fixation. Members of this group, belonging to the Rhizobiaceae family (for example *Mesorhizobium loti, Rhizobium meliloti, Bradyrhizobium japonicum, Rhizobium leguminosarum* by viceae) here collectively called *Rhizobium* or *Rhizobia* spp and the actinobacterium *Frankia* spp, can form endosymbiotic associations with plants conferring the ability to fix nitrogen. Although many plants can associate with nitrogen fixing bacteria, only a few plants, all members of the Rosid I Clade, form endosymbiotic associations with *Rhizobia* spp and *Frankia* spp., which are unique in that most of the nitrogen is transferred to and assimilated by the host plant. Legumes, including soybean, bean, pea, peanut, chickpea, cowpea, lentil, pigeonpea, alfalfa and clover, are the most agronomically important members of this small group of nitrogen-fixing plants. The rhizobial-legume interaction is generally host-strain specific, whereby successful symbiotic associations only occur between specific rhizobial strains and a limited number of legume species. The specificity of this interaction is determined by chemical signalling between plant and bacteria, which accompanies the initial interaction and the establishment of the symbiotic association (Hirsch et al. 2001, *Plant Physiol.* 127: 1484-1492). Specific (iso)flavanoids, secreted into the soil by legume spp, allow *Rhizobium* spp to distinguish compatible hosts in their proximity and to migrate and associate with roots of the host. In a compatible interaction, the (iso)flavanoid perceived by the *Rhizobium* spp, interacts with the rhizobial nodD gene product, which in turn leads to the induction of rhizobial Nod-factor synthesis. Nod-factor molecules are lipo-chitin-oligosaccharides, commonly comprising four or five β-1-4 linked N-acetylglucosamines, with a 16 to 18 carbon chain fatty acid n-acetylated on the terminal non-reducing sugar. Nod factors are synthesised in a number of variants, characterised by their chemically different substitutions on the chitin backbone which are distinguished by the compatible host plant. The perception of Nod-factors by the host induces invasion zone root hairs, in the proximity of rhizobial cells, to curl and entrap the bacteria. The adjacent region of the root hair plasma membrane invaginates and new cell wall material is synthesized to form an infection thread or tube, which serves to transport the symbiotic bacteria through the epidermis to the cortical cells of the root. Here the cortical cells are induced to divide to form a primordium, from which a root nodule subsequently develops. In legumes belonging to genera like *Arachis* (peanut), Stylosantos and Sesbania, infection is initiated by a simple "crack entry" through spaces or cavities between epidermal cells and lateral roots. In spite of these differences, perception of Nod factors by the host plant simultaneously induces the expression of a series of plant nodulin genes, which control the development and function of root nodules, wherein the rhizobial endosymbiotic association and nitrogen fixation are localised. A variety of molecular approaches have identified a series of plant nodulin genes which play a role in rhizobial-legume symbiosis, and whose expression is induced at early or later stages of rhizobial infection and nodule development (Geurts and Bisseling, 2002, *Plant Cell* supplement S239-249). Furthermore, plant mutant studies have revealed that a signalling pathway must be involved in amplifying and transducing the signal resulting from nod-factor perception, which is required for the induction of nodulin gene expression. Among the first physiological events identified in this signal transduction pathway, which occurs circa 1 min after Nod-factor application to the root epidermis, is a rapid calcium influx followed by chloride efflux, causing depolarisation of the plasma membrane and alkalization of the external root hair space of the invasion zone. A subsequent efflux of potassium ions allows re-polarisation of the membrane, and later a series of calcium oscillations are seen to propagate the signal through the root hair cell. Pharmacological studies with specific drugs, which mimic or block Nod-factor induced responses, have identified potential components of the signalling pathway. Thus mastoparan, a peptide which is thought to mimic the activated intracellular domain of G-protein coupled receptors, can induce early Nod gene expression and root hair curling. This suggests that trimeric G protein may be involved in the Nod-factor signal transduction pathway. Analysis of a group of nodulation mutants, including some that fail to show calcium oscillations in response to Nod-factor signals, has revealed that in addition to the lack of nodulation, these mutants are unable to form endosymbioses with arbuscular mycorrhizal fungi. This implies that a common symbiotic signal transduction pathway is shared by two types of endosymbiotic relationships, namely root nodule symbiosis, which is largely restricted to the legume family, and arbuscular mycorrhizal symbiosis, which is common to the majority of land plant species. This suggests that there may be a few key genes which dispose legumes to engage in nodulation, and which are missing from crop plants such as cereals.

The identification of these key genes, which encode functions which are indispensable for establishing a nitrogen fixing system in legumes, and their transfer and expression in non-nodulating plants, has long been a goal of molecular plant breeders. This could have a significant agronomic impact on the cultivation of cereals such as rice, where production of two harvests a year may require fertilisation with up to 400 kg nitrogen per hectare. In accordance with this goal, WO02102841 describes the gene encoding the NORK polypeptide, isolated from the nodulating legume *Medicago sativa*, and the transformation of this gene into plants incapable of nitrogen fixation. The NORK polypeptide and its homologue/orthologue SYMRK from *Lotus japonicus* (Stracke et al 2002 *Nature* 417:959-962), are transmembrane receptor-like kinases with an extracellular domain comprising leucine-rich repeats, and an intracellular protein kinase domain. *Lotus japonicus* mutants, with a non-functional SYMRK gene, fail to form symbiotic relationships with either nodulating *rhizobia* or arbuscular mycorrhiza. This implies that a common symbiotic signalling pathway mediates these two symbiotic relationships, where SYMRK comprises an early step in the pathway. The symRK mutants retain an initial response to rhizobial infection, whereby the root hairs in the susceptable invasion zone undergo swelling of the root hair tip and branching, but fail to curl. This suggests that the SYMRK protein is required for an early step in the common symbiotic signalling pathway, located downstream of the perception and binding of microbial signal molecules (e.g. Nod-factors), that leads to the activation of nodulin gene expression.

The search for key symbiosis genes has also focussed on 'candidate genes' encoding receptor proteins with the potential for perceiving and binding Nod-factors or surface structures on rhizobial bacteria. U.S. Pat. No. 6,465,716 discloses NBP46, a Nod-factor binding lectin isolated from *Dolichos biflorus* roots, and its transgenic expression in transformed plants. Transgenic expression of NBP46 in plants is reported to confer the ability to bind to specific carbohydrates in the rhizobial cell wall and thereby to bind these bacteria and utilise atmospheric nitrogen, as well as conferring apyrase activity. An alternative approach to search for key symbiosis genes has been to screen for Nod-factor binding proteins in protein extracts of plant roots. NFBS1 and NFBS2 were isolated from *Medicago trunculata* and shown to bind Nod-factors in nanomolar concentrations, however, they both failed to exhibit the Nod-factor specificity characteristic of rhizobial-legume interactions (Geurts and Bisseling, 2002 supra).

The Nod-factor binding element, which is responsible for strain specific Nod-factor perception is not, as yet, identified. The isolation and characterisation of this element and its respective gene(s) would open the way to introducing Nod-factor recognition into non-nodulating plants and thereby the potential to establish *Rhizobium*-based nitrogen fixation in important crop plants.

Rhizobial strains produce strain-specific Nod-factors, lipochitin oligosaccharides (LCOs), which are required for a host-specific interaction with their respective legume hosts. *Lotus* and peas belong to two different cross-inoculation groups, where *Lotus* develops nodules after infection with *Mesorhizobium loti*, while pea develops nodules with *Rhizobium leguminosarum* by viceae. Cultivars belonging to a given *Lotus* sp also vary in their ability to interact and form nodules with a given rhizobial strain. Perception of Nod-factor secreted by *Rhizobium* spp bacteria, as the first step in nodulation, commonly leads to the initiation of tens or even hundreds of rhizobial infection sites in a root. However, the majority of these infections abort and only in a few cases do the *rhizobia* infect the nodule primordium. The frequency and efficiency of the *Rhizobium*-legume interaction leading to infection is known to be influenced by variations in Nod-factor structure. The genetics of Nod-factor synthesis and modification of their chemical structure in *Rhizobium* spp have been extensively characterised. An understanding of Nod-factor binding and perception, and the structure of its component elements is needed in order to optimise the host Nod-factor response. This information would, in turn, provide the necessary tools to breed for enhanced efficiency of nodulation and nitrogen fixation in current nitrogen-fixing crops.

The importance of this goal is clearly illustrated by the performance of the major US legume crop, soybean, which is grown on 15%, or more, of agricultural land in the US. While nitrogen fixation by soybean root nodules can assimilate as much as 100 kg nitrogen per hectare per year, these high levels of nitrogen assimilation are insufficient to support the growth of the highest yielding modern soybean cultivars, which still require the application of fertiliser.

In summary, there is a need to increase the efficiency of nodulation and nitrogen fixation in current legume crops as well as to transfer this ability to non-nodulating crops in order to meet the nutritional needs of a growing global population, while minimising the future use of nitrogen fertilisers and their associated negative environmental impact.

SUMMARY OF THE INVENTION

The invention provides an isolated Nod-factor binding element comprising one or more isolated NFR polypeptide having a specific Nod-factor binding property, or a functional fragment thereof, wherein the NFR amino acid sequence is at least 60% identical to either of SEQ ID NO: 8, 15 or 25. The isolated NFR polypeptides of the invention include NFR1, comprising an amino acid sequence selected from the group consisting of SEQ ID No: 24, 25, 52 and 54, having specific Nod-factor binding properties, and NFR5 comprising an amino acid sequence selected from the group consisting of SEQ ID No: 8, 15, 32, 40 and 48, having specific Nod-factor binding properties. Furthermore, the invention provides an isolated nucleic acid molecule encoding a NFR1 polypeptide or a NFR5 polypeptide of the invention, and an expression cassette, and vector and transformed cell comprising said isolated nucleic acid molecule. In a further embodiment is provided a nucleic acid molecule encoding a NFR polypeptide of the invention that hybridises with a nucleic acid molecule comprising a nucleotide sequence selected from the group consisting of SEQ ID No: 6, 7, 11, 12, 21, 22, 23, 39, 47, 51 and 53.

According to a further embodiment of the invention, a method is provided for producing a plant expressing the Nod-factor binding element, the method comprising introducing into the plant a transgenic expression cassette comprising a nucleic acid sequence, encoding the NFR polypeptide of the invention, wherein the nucleic acid sequence is operably linked to its own promoter or a heterologous promoter, preferably a root specific promoter. In a preferred embodiment, the expression of both said NFR 1 and NFR5 polypeptides by the transgenic plant confers on the plant the ability to bind Nod-factors in a chemically specific manner and thereby initiate the establishment of a *Rhizobium*-plant interaction leading to the development of nitrogen-fixing root nodules.

According to a further embodiment, the invention provides a method for marker assisted breeding of NFR alleles, encoding variant NFR polypeptides, comprising the steps of identifying variant NFR polypeptides in a nodulating legume species, comprising an amino acid sequence substantially similar to variant NFR polypeptide having specific Nod-factor binding properties and having an amino acid sequence selected from the group consisting of SEQ ID No: 8, 15, 24, 25, 32, 40, 48, 51 and 53; determining the nodulation frequency of plants expressing said variant NRF polypeptide; identifying DNA polymorphisms at loci genetically linked to or within the allele locus encoding said variant NFR locus; preparing molecular markers based on said DNA polymorphisms; and using said molecular markers for the identification and selection of plants carrying NFR alleles encoding said variant NFR polypeptides. The invention includes plants selected by the use of this method of marker assisted breeding. In a preferred embodiment, said method of marker assisted breeding of NFR alleles provides for the breeding legumes with enhanced nodulation frequency and nodule occupancy.

BRIEF DESCRIPTION OF THE FIGURES

FIG. 2: Structure and domains of the NFR5 protein. a. Schematic representation of the NFR5 protein domains. b. The amino acid sequence of NFR5 arranged in protein domains. Bold, conserved LysM residues. Bold and underlined residues conserved in protein kinase domains (KD); TM: transmembrane, SP: signal peptide. The asterisk indicates a stop codon in the nfr5-3; the black triangle a retrotransposon insertion in nfr5-2 and the box defines the amino acids deleted in nfr5-1. c. Individual alignment of the three LysM motifs (M1, M2, M3) from NFR5, pea SYM10, Medicago truncatula (M.t, Ac126779) rice (Ac103891), the single LysM in chitinase from Volvox carteri (Acc. No: T08150) and the pfam consensus. d. The divergent or absent activation loop (domain VIII) in the NFR5 family of receptor kinases is illustrated by alignment of kinase motifs VII, VIII and IX from Arabidopsis (At2g33580) NFR5, SYM10, Medicago truncatula (M.t, Ac126779), rice (Ac103891) and the SMART concensus. Conserved domain VII aspartic acid is marked in bold and underlined. In FIG. 2c and d, the amino acids conserved in all aligned motifs are marked in bold and amino acids conserved in two or more motifs are underlined.

FIG. 3. The aligned amino acid sequence of the LjNFR5 and PsSYM10 proteins. The Medicago truncatula (Ac126779) showing 76% amino acid identity to Lotus NFR5 is included to exemplify a substantial identical protein sequence.

FIG. 6. Structure and domains of the NFR1 protein. a. Primary structure of the NFR1 protein comprising a signal peptide (SP); LysM motifs (LysM1 and LysM2); transmembrane region (TM); protein kinase domains with conserved amino acids in bold and underlined (PK). The cysteine couples (CxC) are in bold and the LysM amino acids important for secondary structure maintenance are underlined. The two extra amino acids resulting from alternative splicing are shown in brackets. I-XI represent the kinase domains. Asterisks indicate positions of the nonsense mutations found in NFR1-1 and NFR1-2 mutant alleles. b. Alignments of the two NFR1LysM motifs to the consensus sequences predicted by the SMART program and the Arabidopsis thaliana (Acc No: NP566689), rice (O. sativa) (Acc No: BAB89226), and Volvox carteri (Acc. No: T08150) LysM motifs.

FIG. 11. Alignment NFR1 and NFR5 proteins reveal an overall similarity of 33% amino acid identities FIG. 12. Domain structure of native and hybrid NFR1 and NFR5 polypeptides.

DETAILED DESCRIPTION OF THE INVENTION

I. Definitions

Figure 1:
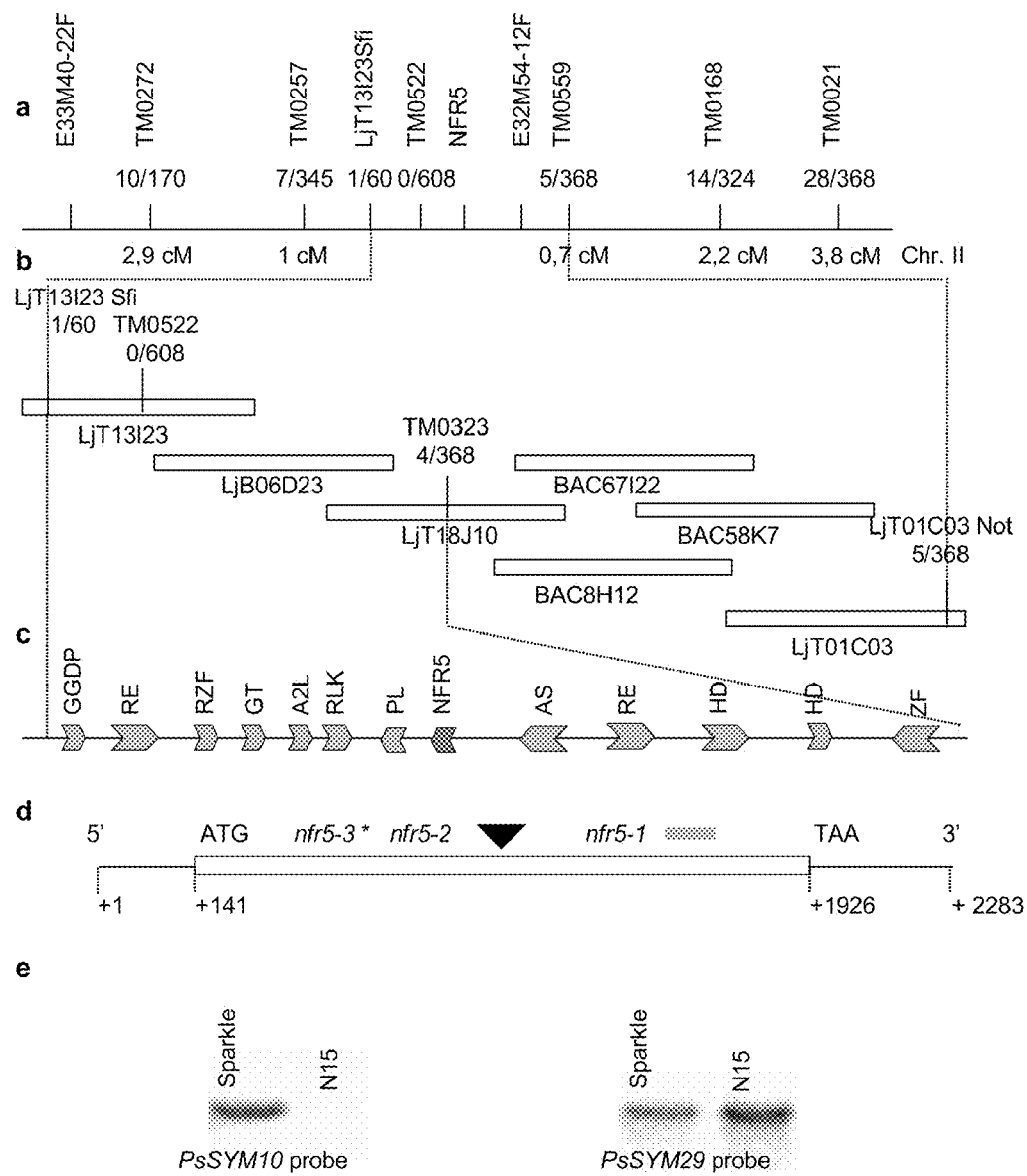
FIG. 1: Map based cloning of Lotus NFR5. a. Genetic map of the NFR5 region with positions of linked AFLP and microsatellite markers above the line and distances in cM below. The fraction of recombinant plants detected in the mapping population is indicated. b. Physical map of the BAC and TAC clones between the closest linked microsatellite markers. The positions of sequence-derived markers used to fine-map the NFR5 locus, and the fraction of recombinant plants found in the mapping population are indicated. c. Candidate genes identified in the sequenced region delimited by the closest linked recombination events. d. Structure of the NFR5 gene, position of the transcription initiation point and the nfr5-1, nfr5-2 and nfr5-3 mutations. The asterisk indicates the position of a stop codon in nfr5-3; the black triangle a retrotransposon insertion in nfr5-2; and the grey box defines the deletion in nfr5-1. GGDP: geranylgeranyl diphosphate synthase; RE: retroelement; RZF: ring zinc finger protein; GT: glycosyl transferase; A2L: apetala2-like protein; RLK: receptor-like kinase; PL: pectate lyase-like protein; AS: ATPase-subunit; HD: homeodomain protein; RF: ring finger protein. Hypothetical proteins are not labelled. e. Southern hybridization demonstrating deletion of SYM10 in the "N15" sym10 mutant line. EcoRI digested genomic DNA of the parental variety "Sparkle" and the fast neutron derived mutant "N15" hybridized with a pea SYM10 probe covering the region encoding the predicted extracellular domain. Hybridization with a probe from the 3' untranslated region demonstrated that the complete gene was deleted.

AFLP: Amplified Fragment Length Polymorphism is a PCR-based technique for the amplification of genomic fragments obtained after digestion with two different enzymes. Different genotypes can be differentiated based on the size of amplified fragments or by the presence or absence of a specific fragment (Vos, P. (1998), *Methods Mol. Biol.*, 82:147-155). Amplified Fragment Length Polymorphism is a PCR-based technique used to map genetic loci.

*Agrobacterium rhizogenes*-mediated transformation: is a technique used to obtain transformed roots by infection with *Agrobacterium rhizogenes*. During the transformation process the bacteria transfers a DNA fragment (T-DNA) from an endogenous plasmid into the plant genome (Stougaard, J. et al, (1987) *Mol. Gen. Genet.* 207, 251-255). For transfer of a gene of interest the gene is first inserted into the T-DNA region of *Agrobacterium rhizogenes* which is subsequently used for wound-site infection.

Allele: gene variant

BAC clones: clones from a Bacterial Artificial Chromosome library

Conservatively modified variant: when referring to a polypeptide sequence when compared to a second sequence, includes individual conservative amino acid substitutions as well as individual deletions, or additions of amino acids. Conservative amino acid substitution tables, providing functionally similar amino acids are well known in the art. When referring to nucleic acid sequences, conservative modified variants are those that encode an identical amino acid sequence, in recognition of the fact that codon redundancy allows a large number of different sequences to encode any given protein.

Contig: a series of overlapping cloned sequences e.g. BACs, co-linear and homologous to a region of genomic DNA.

Exons: protein coding sequences of a gene sequence

Expression cassette: refers to a nucleic acid sequence, comprising a promoter operably linked to a second nucleic acid sequence containing an ORF or gene, which in turn is operably linked to a terminator sequence.

Heterologous: A polynucleotide sequence is "heterologous to" an organism or a second polynucleotide sequence if it originates from a foreign species, or from a different gene, or is modified from its original form. A heterologous promoter operably linked to a coding sequence refers to a promoter from a species, different from that from which the coding sequence was derived, or, from a gene, different from that from which the coding sequence was derived.

Homologue: is a gene or protein with substantial identity to another gene's sequence or another protein's sequence.

Identity: refers to two nucleic acid or polypeptide sequences that are the same or have a specified percentage of nucleic acids of amino acids that are the same, when compared and aligned for maximum correspondence over a comparison window, as measured using one of the sequence comparison algorithms listed herein, or by manual alignment and visual inspection. When percentage of sequence identity is used in reference to proteins, it is recognized that residue positions that are not identical often differ by conservative amino acid substitutions, where amino acid residues are substituted for amino acid residues with similar chemical properties (e.g., charge or hydrophobicity) and therefore do not change the functional properties of the molecule. Where sequences differ in conservative substitutions, the percent sequence identity may be adjusted upwards to account for the conservative nature of the substitution. Typically this involves scoring a conservative substitution as a partial rather than a full mismatch, thus increasing the percent identity. Means for making these adjustments are well known to those skilled in the art.

Introns: are non-coding sequences interrupting protein coding sequences within a gene sequence.

LCO: lipochitin oligosaccharides.

Legumes: are members of the plant Family Fabaceae, and include bean, pea, soybean, clover, vetch, alfalfa, peanut, pigion pea, chickpea, fababean, cowpea, lentil in total approximately 20.000 species.

Locus: or "loci" refers to the map position of a nucleic acid sequence or gene on a genome.

Marker assisted breeding: the use of DNA polymorphisms as "molecular markers", (for examples simple sequence repeats (microsatelittes) or single nucleotide polymorphism (SNP)) which are found at loci, genetically linked to, or within, the NFR1 or NFR5 loci, to breed for advantageous NFR alleles.

Molecular markers: refer to sites of variation at the DNA sequence level in a genome, which commonly do not show themselves in the phenotype, and may be a single nucleotide difference in a gene, or a piece of repetitive DNA.

Monocotyledenous cereal: includes, but is not limited to, barley, maize, oats, rice, rye, sorghum, and wheat.

Mutant: a plant or organism with a modified genome sequence resulting in a phenotype which differs from the common wild-type phenotype.

Native: as in "native promoter" refers to a promoter operably linked to its homologous coding sequence.

NFR: refers to NFR genes or cDNAs, in particular NFR1 and NFR5 genes or cDNAs which encode NFR1 and NFR5 polypeptides respectively.

NFR polypeptides: are polypeptides that are required for Nod-factor binding and function as the Nod-factor binding element in nodulating plants. NFR polypeptides include the NFR5 polypeptide, having an amino acid sequence substantially identical to any one of SEQ ID No: 8, 15, 32, 40 or 48 and the NFR1 polypeptide having an amino acid sequence substantially identical to any one of SEQ ID No: 24, 25, 52 or 54. NFR5 and NFR1 polypeptides show little sequence homology, but they share a similar domain structure comprising an N-terminal signal peptide, an extracellular domain having 2 or 3 LysM-type motifs, followed by a transmembrane domain, followed by an intracellular domain comprising a kinase domain characteristic of serine/threonine kinases. The extracellular domain of NFR proteins is the primary determinant of the specificity of Nod-factor recognition, whereby a host plant comprising a given NFG allele will only form nodules with one or a limited number of *Rhizobium* strains. A functional fragment of an NFR polypeptide is one which retains all of the functional properties of a native NFR nod-factor binding polypeptide, including nod-factor binding and interaction with the nod-factor signalling pathway.

Northern blot analysis: a technique for the quantitative analysis of mRNA species in an RNA preparation.

Nod-factors: are synthesised by nitrogen-fixing *Rhizobium* bacteria, which form symbiotic relationships with specific host plants. They are lipo-chitin-oligosaccharides (LCOs), commonly comprising four or five β-1-4 linked N-acetylglucosamines, with a 16 to 18 carbon chain fatty acid n-acetylated on the terminal non-reducing sugar. Nod-factors are synthesised in a number of chemically modified forms, which are distinguished by the compatible host plant.

Nod-factor binding element: comprises one or more NFR polypeptides present in the roots of nodulating plants, and functions in detecting the presence of Nod-factors at the root surface and within the root and nodule tissues. The NFR polypeptides, which are essential for Nod-factor detection, comprise the first step in the Nod-factor signalling pathway that triggers the development of an infection thread and root nodules.

Nod-factor binding properties: are a characteristic of NFR1 and NFR5 polypeptides and are particularly associated with the extracellular domain of said NFR polypeptides, which comprise LysM domains. The binding of Nod-factors by the extracellular domain of NFR polypeptides is specific, such the NFR polypeptides can distinguish between the strain-specific chemically modified forms of Nod-factor.

Nodulating plant: a plant capable of establishing an endosymbiotic *Rhizobium*—plant interaction with a nitrogen-fixing *Rhizobium* bacterium, including the formation of an infection thread, and the development of root nodules capable of fixing nitrogen. Nodulating plants are limited to a few plant families, and are particularly found in the Legume family, and they are all member of the Rosid 1 lade.

Non-nodulating plant: a plant which is incapable of establishing an endosymbiotic Rhizobial—plant interaction with a nitrogen-fixing Rhizobial bacterium, and which does not form root nodules capable of fixing nitrogen.

Operably linked: refers to a functional linkage between a promoter and a second sequence, wherein the promoter sequence initiates transcription of RNA corresponding to the second sequence.

ORF: Open Reading Frame, which defines one of three putative protein coding sequences in a DNA polynucleotide.

Orthologue: Two homologous genes (or proteins) diverging concurrently with the organism harbouring them diverged. Orthologues commonly serve the same function within the organisms and are most often present in a similar position on the genome.

PCR: Polymerase Chain Reaction is a technique for the amplification of DNA polynucleotides, employing a heat stable DNA polymerase and short oligonucleotide primers, which hybridise to the DNA polynucleotide template in a sequence specific manner and provide the primer for 5' to 3' DNA synthesis. Sequential heating and cooling cycles allow denaturation of the double-stranded DNA template and sequence-specific annealing of the primers, prior to each round of DNA synthesis. PCR is used to amplify DNA polynucleotides employing the following standard protocol or modifications thereof:

PCR amplification is performed in 25 µl reactions containing: 10 mM Tris-HCl, pH 8.3 at 25° C.; 50 mM KCl; 1.5 mM $MgCl_2$; 0.01% gelatin; 0.5 unit Taq polymerase and 2.5 pmol of each primer together with template genomic DNA (50-100 ng) or cDNA. PCR cycling conditions comprise heating to 94° C. for 45 seconds, followed by 35 cycles of 94° C. for 20 seconds; annealing at $X°$ C. for 20 seconds (where X is a temperature between 40 and 70° C. defined by the primer annealing temperature); 72° C. for 30 seconds to several minutes (depending on the expected length of the amplification product). The last cycle is followed by heating to 72° C. for 2-3 minutes, and terminated by incubation at 4° C.

Pfam consensus: a consensus sequence derived from a large collection of protein multiple sequence alignments and profile hidden Markov models used to identify conserved protein domains (Bateman et al., 2002, Nucleic Acids Res. 30: 276-80; and searchable on the internet at sanger.ac.uk/Software/Pfam/ and on NCBI at ncbi.nlm.nih.gov/Structure/cdd/wrpsb.cgi Protein domain prediction: sequences are analysed by BLAST (ncbi.nlm.nih.gov/BLAST) and PredictProtein (emblheidelberg.de/predictprotein/predictprotein.). Signal peptides are predicted by SignalP v. 1.1 (cbs.dtu.dk/services/signalP) and transmembrane regions are predicted by TMHMM v. 2.0 (cbs.dtu.dk/services/TMHMM).

Polymorphism: refers to "DNA polymorphism" due to nucleotide sequence differences between aligned regions of two nucleic acid sequences.

Polynucleotide molecule: or "polynucleotide", or "polynucleotide sequence" or "nucleic acid sequence" refers to deoxyribonucleotides or ribonucleotides and polymers thereof in either single- or double-stranded form. The term encompasses nucleic acids containing known analogs of natural nucleotides, which have similar binding properties as the reference nucleic acid.

Promoter: is an array of nucleic acid control sequences that direct transcription of an operably linked nucleic acid. As used herein, a "plant promoter" is a promoter that functions in plants. Promoters include necessary nucleic acid sequences near the start site of transcription, e.g. a TATA box element, and optionally includes distal enhancer or repressor elements, which can be located several 1000 bp upstream of the transcription start site. A tissue specific promoter is one which specifically regulates expressed in a particular cell type or tissue e.g. roots. A "constitutive" promoter is one that is active under most environmental and developmental conditions throughout the plant.

RACE/5'RACE/3'RACE: Rapid Amplification of cDNA Ends is a PCR-based technique for the amplification of 5' or 3' regions of selected cDNA sequences which facilitates the generation of full-length cDNAs from mRNA. The technique is performed using the following standard protocol or modifications thereof: mRNA is reverse transcribed with RNase H⁻ Reverse Transcriptase essentially according to the protocol of Matz et al, (1999) *Nucleic Acids Research* 27: 1558-60 and amplified by PCR essentially according to the protocol of Kellogg et al (1994) *Biotechniques* 16(6): 1134-7. Real-time PCR: a PCR-based technique for the quantitative analysis of mRNA species in an RNA preparation. The formation of amplified DNA products during PCR cycling is monitored in real-time, using a specific fluorescent DNA binding-dye and measuring fluorescence emission.

Sexual cross: refers to the pollination of one plant by another, leading to the fusion of gametes and the production of seed.

SMART consensus: represents the consensus sequence of a particular protein domain predicted by the Simple Modular Architecture Research Tool database (Schultz, J. et al. (1998)—*PNAS* 26; 95(11):5857-64)

Southern hybridisation: Filters carrying nucleic acids (DNA or RNA) are prehybridized for 1-2 hours at 65° C. with agitation in a buffer containing 7% SDS, 0.26 M $Na_2HPO_4$, 5% dextrane-suphate, 1% BSA and 10 μg/ml denatured salmon sperm DNA. Then the denatured, radioactively labelled DNA probe is added to the buffer and hybridization is carried out over night at 65° C. with agitation. For low stringency, washing is carried out at 65° C. with a buffer containing about 2×SSC, 0.1% SDS for 20 minutes. For medium stringency, washing is continued at 65° C. with a buffer containing about 1×SSC, 0.1% SDS for 2×20 minutes and for high stringency filters are washed a further 2×20 minutes at 65° C. in a buffer containing about 0.5×SSC, 0.1% SDS, or more preferably about 0.3×SSC, 0.1% SDS. Probe labelling by random priming is performed essentially according to Feinberg and Vogelstein (1983) *Anal. Biochem.* 132(1), 6-13 and Feinberg and Vogelstein (1984) Addendum. *Anal. Biochem.* 137(1), 266-267

Substantially identical: refers to two nucleic acid or polypeptide sequences that have at least about 60%, preferably about 65%, more preferably about 70%, further more preferably about 80%, most preferably about 90 or about 95% nucleotide or amino acid residue identity when aligned for maximum correspondence over a comparison window as measured using one of the sequence comparison algorithms given herein, or by manual alignment and visual inspection. This definition also refers to the complement of the test sequence with respect to its substantial identity to a reference sequence. A comparison window refers to any one of the number of contiguous positions in a sequence (being anything from between about 20 to about 600, most commonly about 100 to about 150) which may be compared to a reference sequence of the same number of contiguous positions after the two sequences are optimally aligned. Optimal alignment can be achieved using computerized implementations of alignment algorithms (e.g., GAP, BESTFIT, FASTA, and TFASTA in the Wisconsin Genetics Software Package, Genetics Computer Group, 575 Science Dr., Madison, Wis. USA) or BLAST analyses available on the site: ncbi.nlm.nih.gov.

TAC clones: clones from a Transformation-competent Artificial Chromosome library.

TM marker: is a microsatellite marker developed from a TAC sequence, based on sequence differences between *Lotus japonicus* Gifu and MG-20 genotypes.

Transgene: refers to a polynucleotide sequence, for example a "transgenic expression cassette", which is integrated into the genome of a plant by means other that a sexual cross, commonly referred to as transformation, to give a transgenic plant.

UTR: untranslated region of an mRNA or cDNA sequence.

Variant: refers to "variant NFR1 or NFR5 polypeptides" encoded by different NFR alleles.

Wild type: a plant gene, genotype, or phenotype predominating in the wild population or in the germplasm used as standard laboratory stock.

II. Nod-factor Binding

The present invention provides a Nod-factor binding element comprising one or more isolated NFR polypeptides. The isolated NFR polypeptides, NFR1, as exemplified by SEQ ID No: 24 and 25; and NFR5 (including SYM10) as exemplified by SEQ ID No: 8 and 15 bind to Nod-factors in a chemically-specific manner, distinguishing between the different chemically modified forms of Nod-factors produced by different *Rhizobium* strains. The chemical specificity of Nod-factor binding by NFR1 and NFR5 polypeptides is located in their extracellular domain, which comprises LysM type motifs. The LysM protein motif, first identified in bacterial lysin and muramidase enzymes degrading cell wall peptidoglycans, is widespread among prokaryotes and eukaryotes (Pontig et al. 1999, *J Mol. Biol.* 289, 729-745; Bateman and Bycroft, 2000, *J Mol Biol,* 299, 1113-1119). In bacteria it is often found in proteins associated with bacterial cell walls or involved in pathogenesis and in vivo and in vitro studies of *Lactococcus lactis* autolysin demonstrate that the three LysM domains of this protein bind peptidoglycan (Steen et al, 2003, *J Biol. Chem.* April issue). Since both A- and B-type peptidoglycans, differing in amino acid composition as well as cross-linking were bound, it was concluded that autolysin LysM domains binds the N-acetyl-glucosamine-N-acetyl-murein backbone polymer. LysM domains are frequently found together with amidase, protease or chitinase motifs and two confirmed chitinases carry LysM domains. One is the sex pheromone and wound-induced polypeptide from the alga *Volvox carteri* that binds and degrades chitin in vitro (Amon et al. 1998, Plant Cell 10, 781-9). The other is α-toxin from *Kluyveromyces lactis*, that docs onto a yeast cell wall chitin receptor (Butler, et al. (1991) Eur J Biochem 199, 483-8). Structure-based alignment of representative LysM domain sequences have shown a pronounced variability among their primary sequence, except the amino acids directly involved in maintaining the secondary structure.

The NFR polypeptides are transmembrane proteins, able to transduce signals perceived by the extracellular NFR domain across the membrane to the intracellular NFR domain comprising kinase motifs, which serves to couple signal perception to the common symbiotic signalling pathway leading to nodule development and nitrogen fixation.

The methods employed for the practise and understanding of the invention, which are described below, involve standard recombinant DNA technology that are well-known and commonly employed in the art and available from Sambrook et al., 1989, *Molecular Cloning: A laboratory manual*.

III. Isolation of Nucleic Acid Molecules Comprising NRF Genes and cDNAs Encoding NFR1 and NFR5 Polypeptides and their Orthologues The isolation of genes and cDNAs encoding NFR1 or NFR5 (or SYM10) polypeptides, comprising an amino acid sequence substantially similar to SEQ ID No: 24 or 25 (NFR1); or SEQ ID No: 8 or 15 (NFR5) respectively, may be accomplished by a number of techniques. For instance, a BLAST search of a genomic or cDNA sequence bank of a desired legume plant species (e.g. soybean, pea or *Medicago truncatula*) can identify test sequences similar to the NFR1 or NFR5 reference sequence, based on the smallest sum probability score (P(N)). The (P(N)) score (the probability of the match between the test and reference sequence occurring by chance) for a "similar sequence" will be less than about 0.2, more preferably less than about 0.01, and most preferably less than about 0.001. This approach is exemplified by the *Medicago truncatula* sequence (Ac126779; SEQ ID No: 32) included in FIG. 3. Oligonucleotide primers, together with PCR, can be used to amplify regions of the test sequence from genomic or cDNA of the selected plant species, and a test sequence which is similar to the full-length NFR1 or NFR5 (or SYM10) gene sequences can be assembled. In the case that an appropriate gene bank is not available for the selected plant species, oligonucleotide primers, based on NFR1 or NFR5 (or SYM10) gene sequences, can be used to PCR amplify similar sequences from genomic or cDNA prepared from the selected plant. The application of this approach is demonstrated in Example 1A.6, where the isolated NFR5 gene homologues from *Glycine max* and *Phaseolus vulgaris* are disclosed.

Alternatively, nucleic acid probes based on NFR1 or NFR5 (or SYM10) gene sequences can be hybridised to genomic or cDNA libraries prepared from the selected plant species using standard conditions, in order to identify clones comprising sequences similar to NFR1 or NFR5 genes. A nucleic acid sequence in a library, which hybridises to a NFR1 or NFR5 gene-specific probe under conditions which include at least one wash in 2×SSC at a temperature of at least about 65° C. for 20 minutes, is potentially a similar sequence to a NFR1 or NFR5 (or SYM10) gene. The application of this approach is demonstrated in Example 1B. 4, where the isolation of a pea NFR1 homologue from *Pisum sativum* is disclosed. A test sequence comprising a full-length cDNA sequence similar to NFR1 cDNAs having SEQ ID No: 21, or 22, or 51, or 53; or similar to NFR5 cDNAs having SEQ ID No: 6 or 12 can be generated by 5' RACE cDNA synthesis, as described herein.

The nucleic acid sequence of each test sequence, derived from a selected plant species, is determined in order to identify a nucleic acid molecule that is substantially identical to a NFR1 or NFR5 gene having SEQ ID No: 23 (NFR1), or any one of SEQ ID No: 7, 11, 13, 14, 39 or 47 (NFR5) respectively; or a nucleic acid molecule that is substantially identical to a NFR1 or NFR5 cDNA having any one of SEQ ID No: 21, 22, 51, or 53 (NFR1), or having SEQ ID No: 6 (NFR5) or 12 (SYM10) respectively; or a nucleic acid molecule that encodes a protein whose amino acid sequence is substantially identical to NFR1 or NFR5 having any one of SEQ ID No: 24, 25, 52 or 54 (NFR1) or having any one of SEQ ID No. 8, 32, 40, or 48 (NFR5) or 15 (SYM10), respectively.

IV. Transgenic Plants Expressing NFR1 and/or NFR5 Polypeptides

The polynucleotide molecules of the invention can be used to express a Nod-factor binding element in non-nodulating plants and thereby confer the ability to bind Nod-factors and establish a *Rhizobium*/plant interaction leading to nodule development. An expression cassette comprising a nucleic acid sequence encoding a NFR polypeptide, substantially identical to any one of SEQ ID No: 8, 15, 24, or 25, and operably linked to its own promoter or a heterologous promoter and 3' terminator can be transformed into a selected host plant using a number of known methods for plant transformation. By way of example, the expression cassette can be cloned between the T-DNA borders of a binary vector, and transferred into an *Agrobacterium tumerfaciens* host, and used to infect and transform a host plant. The expression cassette is commonly integrated into the host plant in parallel with a selectable marker gene giving resistance to an herbicide or antibiotic, in order to select transformed plant tissue. Stable integration of the expression cassette into the host plant genome is mediated by the virulence functions of the *Agrobacterium* host. Binary vectors and *Agrobacterium tumefaciens*-based methods for the stable integration of expression cassettes into all major cereal plants are known, as described for example for rice (Hiei et al., 1994, *The Plant J.* 6: 271-282) and maize (Yuji et al., 1996, *Nature Biotechnology*, 14: 745-750). Alternative transformation methods, based on direct transfer can also be employed to stably integrate expression cassettes into the genome of a host plant, as described by Miki et al., 1993, "Procedure for introducing foreign DNA into plants", In: *Methods in Plant Molecular Biology and Biotechnology*, Glick and Thompson, eds., CRC Press, Inc., Boca Raton, pp 67-88). Promoters to be used in the expression cassette of the invention include constitutive promoters, as for example the 35S CaMV promoter (Acc V00141 and J02048) or in the case or a cereal host plant the Ubi1 gene promoter (Christensen et al., 1992, *Plant Mol Biol* 18: 675-689). In a preferred embodiment, a root specific promoter is used in the expression cassette, for example the maize zmGRP3 promoter (Goodemeir et al. 1998, *Plant Mol Biol,* 36, 799.802) or the epidermis expressed maize promoter described by Ponce et al. 2000, *Planta,* 211, 23-33. Terminators that may be used in the expression construct can for instance be the NOS terminator (Acc NC_003065).

Host plants transformed with an expression cassette encoding one NFR polypeptide, for example NFR1, or its orthologue, can be crossed with a second host plant transformed with an expression cassette encoding a second NFR polypeptide, for example NFR5, or its orthologue. Progeny expressing both said NFR polypeptides can then be selected and used in the invention. Alternatively, host plants can be transformed with a vector comprising two expression cassettes encoding both said NFR polypeptides.

V. NFR Genes Encoding NFR Polypeptide having Specific Nod-Factor Binding Properties Nucleic acid molecules comprising NFR1 or NFR5 genes encoding NFR polypeptides having specific Nod-factor binding properties can be identified by a number of functional assays described in the "Examples" given herein. In a preferred embodiment, said nucleic acid sequences are expressed transgenically in a host plant employing the expression cassettes described above. Expression of NFR1 or NFR5 genes or their homologues/orthologues in plant roots allows the specific Nod-factor binding properties of the expressed NFR protein to be fully tested. Assays suitable for establishing specific Nod-factor binding include the detection of: a morphological root hair response (e.g. root hair deformation, root hair curling); a physiological response (e.g. root hair membrane depolarisation, ion fluxes, pH changes and calcium oscillations); a symbiotic signalling response (e.g. downstream activation of symbiotic nodulin gene expression) following root infection with *Rhizobium* bacteria or isolated Nod-factors; the ability to develop root nodule primordia, infection pockets or root nodules, where the response is strain dependent or dependent on the chemical modification of Nod-factor structure.

VI. Marker Assisted Breeding for NFR Alleles

A method for marker assisted breeding of NFR alleles, encoding variant NFR polypeptides, is described herein, with examples from *Lotus* and *Phaseolus* NFR alleles. In summary, variant NFR1 or NFR5 polypeptides, comprising an amino acid sequence substantially similar to any one of SEQ ID No: 24, 25, 52 or 54 (NFR1) or any one of SEQ ID No: 8, 15, 32, 40 or 48 (NFR5) respectively, are identified in a nodulating legume species, and the *Rhizobium* strain specificity of said variant NRF1 or NFR5 polypeptide is determined, according to measurable morphological or physiological parameters described herein. Subsequently, DNA polymorphisms at loci genetically linked to, or within, the gene locus encoding said variant NFR1 or NFR5 polypeptide, are identified on the basis of the nucleic acid sequence of the loci or its neighbouring DNA region. Molecular markers based on said DNA polymorphisms, are used for the identification and selection of plants carrying NFR alleles encoding said variant NFR1 or NFR5 polypeptides. Use of this method provides a powerful tool for the breeding of legumes with enhanced nodulation frequency.

III. Examples

Example 1

Cloning of Nod-factor Binding Element Genes

Genetic studies in the legume plants *Lotus japonicus* (Lj) and pea (Ps) have generated collections of symbiotic mutants, which have been screened for mutants blocked in the early steps of symbiosis (Geurts and Bisseling, 2002 supra; Kistner and Parniske 2002 *Trends in Plant Science* 7: 511-518). Characteristic for a group of the selected mutants is their inability to respond to Nod-factors, with the absence of root hair deformation and curling, cortical cell division to form the cortical primordium, and induction of the early nodulin genes which contribute to nodule development and function. Nod-factor induced calcium oscillations were also found to be absent in some of these mutants, indicating that they are blocked in an early step in Nod-factor signalling. Among this latter group, are a few mutants, including members of the Pssym10 complementation group and LjNFR1 and LjNFR5 (previously called Ljsym1 and 5), which failed to respond to Nod-factors but retain their ability to establish mycorrhizal associations. Genetic mapping indicates that pea SYM10 and *Lotus* NFR5 loci in the pea and *Lotus* could be orthologs. Mutants falling within this group provided a useful starting point in the search for genes encoding potential candidate proteins involved in Nod-factor binding and perception.

A. Isolation, Cloning and Characterisation of NFR5 Genes and Gene Products.

1. Map Based Cloning of Lj NFR5

The symbiotic mutants of *Lotus japonicus* nfr5-1, nfr5-2 and nfr5-3 (also known as sym5), (previously isolated by Schauser et al 1998 *Mo. Gen Genet,* 259: 414-423; Szczglowski et al 1998, *Mol Plant-Microbe Interact,* 11: 684-697) were utilised. To determine the root nodulation phenotype under symbiotic conditions, seeds were surface sterilised in 2% hyperchlorite, washed and inoculated with a two day old culture of *M. loti* NZP2235. Plants were cultivated in the nitrogen-free B&D nutrients and scored after 6-7 weeks (Broughton and Dilworth, Biochem J, 1971, 125, 1075-1080; Handberg and Stougaard, *Plant J.* 1992, 2, 487-496). Under non-symbiotic conditions, plants were cultivated in Hornum nutrients (Handberg and Stougaard, *Plant J.* 1992, 2, 487-496).

Mapping populations were established in order to localise the nfr5 locus on the *Lotus japonicus* genome. Both intra- and interspecific F2 mapping populations were created by crossing a *Lotus japonicus* "Gifu" nfr5-1 mutant to wild type *Lotus japonicus* ecotype "MG20" and to wild type *Lotus filicaulis*. MG-20 seeds are obtainable from Sachiko ISOBE, National Agricultural Research Center for Hokkaido Region, Hitsujigaoka, Toyohira, Sapporo Hokkaido 062-8555, JAPAN and *L. filicaulis* from Jens Stougaard, Department of Molecular Biology, University of Aarhus, Gustav Wieds Vej 10, DK-8000 Aarhus C. F2 plants homozygous for the nfr5-1 mutant allele were identified after screening for the non-nodulation mutant phenotype. 240 homozygous F2 mutant plants were analysed in the *L. filicaulis* mapping population and 368 homozygous F2 mutant plants in the "MG20" mapping population.

Positional cloning of the nfr5 locus was performed by AFLP and Bulked Segregant Analysis of the mapping populations using the EcoRI/MseI restriction enzyme combination (Vos et al, 1995, *Nucleic Acids Res.* 23, 4407-4414; Sandal et al 2002, *Genetics,* 161, 1673-1683). Initially, nfr5 was mapped to the lower arm of chromosome 2 between AFLP markers E33M40-22F and E32M54-12F in the *L. filicaulis* based mapping population, as shown in FIG. 1a. The E32M54-12F marker was cloned and used to isolate BAC clones BAC8H12 and BAC67I22 and TAC clone LjT18J10, as shown in FIG. 1b. The ends of this contig were used to isolate adjacent BAC and TAC clones namely BAC58K7 and LjT11C03 at one end and TAC LjB06D23 on the other end. The outer end of LjB06D23 was used to isolate TAC clone LjT13I23. The outer end of LjB06D23 was used to isolate TAC clone LjT13I23 (TM0522). Various markers from this contig were mapped on the mapping populations from nfr5-1 crossed to *L. filicaulis* and to *L. japonicus* MG-20. In the *L. filicaulis* mapping population one recombinant plant was found with the outer end of the TAC clone TM0522, whereas no recombinant plants were found with a marker from the middle of this TAC clone. In the *L. japonicus* MG-20 mapping population, 4 recombinant plants out of 368 plants were found with the marker TM0323, thereby delimiting nfr5 to a region of 150 kb. This region was sequenced and found to contain 13 ORFs, of which two encoded putative proteins sharing sequence homology to receptor kinases. Sequencing of these two specific ORFs in genomic DNA derived from nfr5-1 showed that one of the ORF sequences contained a 27 nucleotide deletion. Furthermore sequencing of this ORF in genomic DNA from nfr5-2 and nfr5-3 showed the insertion of a retrotransposon and a point mutation leading to a premature stop codon, respectively, as shown in FIG. 1d. The localisation of the nfr5 locus from physical and genetic mapping data, combined with the identification of mutations in three independent nfr5 mutant alleles, provides unequivocal evidence that mutations in the NFR5 ORF lead to a loss of Nod-factor perception.

2. Cloning the Lj NFR5 cDNA

A full-length cDNA corresponding to the NFR5 gene was isolated using a combination of 5' and 3' RACE. RNA was extracted from *Lotus japonicus* roots, grown in the absence of nitrate or *rhizobia*, and reverse transcribed to make a full-length cDNA pool for the performance of 5'-RACE according to the standard protocol. The cDNA was amplified using the 5' oligonucleotide 5'CTAATACGACTCACTAT-AGGGCAAGCAGTGGTAACAACGCAGAGT 3' (SEQ ID No:1) and the reverse primer 5'GCTAGTTAAAAATGTAAT-AGTAACCACGC3' (SEQ ID No: 2), and a RACE-product of approximately 2 kb was cloned into a topoisomerase activated plasmid vector (Shuman, 1994, *J Biol Chem* 269: 32678-32684). 3'-RACE was performed on the same 5'-RACE cDNA pool, using a 5' gene-specific primer 5' AAAGCAGCATTCATCTTCTGG 3' (SEQ ID No: 3) and an oligo-dT primer 5'GACCACGCGTATCGATGTC-GACTTTTTTTTTTTTTTTTV 3' (SEQ ID No: 4), where the first 5 PCR cycles were carried out at an annealing temperature of 42° C. and the following 30 cycles at higher annealing temperature of 58° C. The products of this PCR reaction were used as template for a second PCR reaction with a gene-specific primer positioned further 3' having the sequence 5' GCAAGGGAAGGTAATTCAG 3' (SEQ ID No: 5) and the above oligo dT-primer, using standard PCR amplification conditions (annealing at 54° C.; extension 72° C. for 30 s) and the products cloned into a topoisomerase activated plasmid vector (Shuman, 1994, supra). Nucleotide sequencing of 18 5'RACE clones and three 3' RACE clones allowed the full-length sequence of the NFR5 cDNA to be determined (SEQ ID No: 6). The NFR5 cDNA was 2283 nucleotides in length, with an open reading frame of 1785 nucleotides, preceded by a 5' UTR leader sequence of 140 nucleotides and a 3'UTR region of 358 nucleotides. Alignment of the NFR5 cDNA sequence with the NFR5 gene sequence (SEQ ID No: 7), shown schematically in FIG. 1d, confirmed that the gene is devoid of introns.

3. Primary Sequence and Structural Domains of LjNFR5 and Mutant Alleles.

The primary sequence and domain structure of NFR5, encoded by NFR5, are consistent with a transmembrane Nod-factor binding protein, required for Nod-factor perception in rhizobial-legume symbiosis. The NFR5 gene encodes an NFR5 protein of 596 amino acids having the sequence given in FIG. 2b (SEQ ID No: 8) and a predicted molecular mass of 65.3 kD. The protein domain structure predicted for NFR5 and shown in FIGS. 2a,b, defines a signal peptide, comprising a hydrophobic stretch of 26 amino acids, followed by an extracellular domain with three LysM-type motifs, a transmembrane domain and an intracellular kinase domain. The LysM-type motifs found in Lotus NFR5, SYM10, Medicago truncatula (M.t, Ac126779), and by homology in a rice gene (Ac103891), show homology to the single LysM motif present in an algal (Volvox carteria) chitinase (Amon et al, 1998, Plant Cell 10: 781-789) and to the Pfam consensus, as illustrated in the amino acid sequence alignment of this domain given in FIG. 2c. The NFR5 kinase domain has motifs characteristic of functional serine/threonine kinases (Schenk and Snaar-Jagalska, 1999, Biochim Biophys Acta 1449: 1-24; Huse and Kuriyan, 2002, Cell 109: 275-282), with the exception that motif VII lacks an aspartic acid residue conserved in kinases, and motif VIII, comprising the activation loop, is either divergent or absent.

Analysis of the nfr5 mutant genes reveals that the point mutation in nfr5-3 and the retrotransposon insertion in nfr5-2 will express truncated polypeptides of 54 amino acids, lacking the LysM motifs and entire kinase domain; or of 233 amino acids, lacking the kinase motifs X and XI, respectively. The 27 nucleotide deletion in the nfr5-1 mutant removes 9 amino acids from kinase motif V.

4. Cloning and Characterisation of the Pea SYM10 Gene and cDNA and sym10 Mutants.

Wild type pea cv's (Alaska, Finale, Frisson, Sparkle) and the symbiotic mutants (N15; P5; P56) were obtained from the pea germ-plasm collection at JIC Norwich-UK, while the symbiotic mutant, RisFixG, was obtained from Kjeld Engvild, Risø National Laboratory, 8000 Roskilde, Denmark. The mutants, belonging to the pea sym10 complementation group, were identified in the following genetic backgrounds: N15 type strain in a Sparkle background (Kneen et al, 1994, J Heredity 85: 129-133), P5 in a Frisson background (Duc and Messager, 1989, Plant Science 60: 207-213), RisFixG in a Finale background RisFixG (Engvild, 1987, Theoretical Applied Genetics 74: 711-713; Borisov et al., 2000, Czech Journal Genetics and Plant Breeding 36: 106-110); P56 in a Frisson background (Sagan et al. 1994, Plant Science 100: 59-70).

A fragment of the pea SYM10 gene was cloned by PCR amplification of cv Finale genomic DNA using a standard PCR cycling program and the forward primer 5'-ATGTCT-GCCTTCTTTCTTCCTTC-3', (SEQ ID No: 9) and the reverse primer 5'-CCACACATAAGTAATMAGATACT-3', (SEQ ID No: 10). The sequence of these oligonucleotide primers was based on nucleotide sequence stretches conserved in L. japonicus NFR5 and the partial sequence of an NFR5 homologue identified in a M. truncatula root EST collection (BE204912). The identity of the amplified 551 base pair SYM10 product was confirmed by sequencing, and then used as a probe to isolate and sequence a pea cv Alaska SYM10 genomic clone (SEQ ID No:11) from a cv. Alaska genomic library (obtained from H. Franssen, Department of Molecular Biology, Agricultural University, 6703 HA Wageningen, The Netherlands) and a full-length pea cv. Finale SYM10 cDNA clone (SEQ ID No: 12) from a cv. Finale cDNA library (obtained from H. Franssen, supra), which were then sequenced. The sequence of the SYM10 gene in cv. Frisson (SEQ ID No:13) and in cv. Sparkle (SEQ ID No: 14) were determined by a PCR amplification and sequencing of the amplified gene fragment. The nucleotide sequence of the corresponding mutants P5, P56, and RisFixG were also determined by a PCR amplification and sequencing of the amplified gene fragment.

Nucleotide sequence comparison of the SYM10 gene in the Pssym10 mutant lines (P5, RisFix6 and P56) with the wild type parent lines revealed, in each case, sequence mutations, which could be correlated with the mutant phenotype. The 3 independent sym10 mutant lines identified 3 mutant alleles of the SYM10 gene, all carrying nonsense mutations, and the N15 type strain was deleted for SYM10 (Table 5). Southern hybridization with probes covering either the extracellular domain of SYM10 or the 3'UTR on EcoRI digested DNA from N15 and the parent variety Sparkle, shows that the SYM10 gene is absent from the N15 mutant line.

5. Primary Sequence and Structural Domains of PsSYM10 and Mutant Alleles.

The PsSYM10 protein of pea, encoded by PsSYM10, is a homologue of the NFR5 transmembrane Nod-factor binding protein of Lotus, required for Nod-factor perception in rhizobial-legume symbiosis. The pea cv Alaska SYM10 gene encodes a SYM10 protein (SEQ ID No: 15) of 594 amino acid residues, with a predicted molecular mass of 66 kD, which shares 73% amino acid identity with the NFR5 protein from Lotus. In common with the NFR5 protein, the SYM10 protein has an N-terminal signal peptide, an extracellular region with three LysM motifs, followed by a transmembrane domain, and then an intracellular domain comprising kinase motifs (FIGS. 2 and 3). The sym10 genes in the symbiotic pea mutants P5, RisFix6 and P56, each having premature stop codons, encode truncated SYM10 proteins of 199, 387 and 404 amino acids, respectively, which lack part of, or the entire, kinase domain (Table 5).

6. Isolation of NFR5 Gene Orthogues Encoding NFR5 Protein Orthogues

A nucleic acid sequence encoding an NFR5 protein orthologue from bean was isolated from Phaseolus vulgaris "Negro jamapa" as follows. A nucleic acid molecule comprising a fragment of the bean NFR5 orthologous gene was amplified from Phaseolus vulgaris gDNA with the PCR primers: 5'-CATTGCAARAGCCAGTAACATAGA-3' (SEQ ID No: 33) and 5'-AACGWGCWRYWAYRGAAGT-MACAAYATGAG-3 (SEQ ID No: 34) using standard PCR reaction conditions (see Definitions: PCR) with an annealing temperature of 48° C., and the amplified fragment was cloned and sequenced. A full-length cDNA molecule corresponding to the amplified bean NFR5 fragment was obtained by employing 5'-RACE using the oligonucleotide primer: 5'-CGACTGGGATATGTATGTCACATATGTTTCACATG-3' (SEQ ID No: 35) and 3'-RACE using the oligonucleotide primer: 5'-GATAGAATTGCTTACTGGCAGG-3' (SEQ ID No: 36) on bean root RNA according to a standard RACE protocol (see Definitions: RACE). The complete sequence was assembled from both the amplified fragment, 5'RACE- and 3'-RACE products. Finally, the PCR primers: 5'-GACGT-GTCCACTGTATCCAGG-3' (SEQ ID No: 37) and 5'-GTTTGGACATGCAATAAACAACTC-3' (SEQ ID No: 38) derived from the assembled sequence, were used to amplify the entire bean NFR5 gene as a single nucleic acid molecule from genomic DNA of *Phaseolus vulgaris* "Negro Jamapa" and shown to have the sequence of SEQ ID No: 39. A nucleic acid sequence encoding an NFR5 protein orthologue from soybean was isolated from *Glycine max* cv Stevens as follows. A nucleic acid molecule comprising a fragment of the soybean NFR5 orthologous gene was amplified from *Glycine max* cDNA with the PCR primers: 5'-CATTGCAARAGCCAGTAACATAGA-3' (SEQ ID No: 41) and 5'-AACGWGCWRYWAYRGAAGTMACAAYATGAG-3 (SEQ ID No: 42) as described above for the bean NFR5 orthologue. A full-length cDNA molecule corresponding to the amplified soybean NFR5 fragment was obtained by employing 5'-RACE using the oligonucleotide primer: 5'-CCATCACTGCACGCCAATTCGTGAGATTCTC-3' (SEQ ID No: 43) and 3'-RACE using the oligonucleotide primer: 5'-GATGTCTTTGCATTTGGGG-3' (SEQ ID No: 44) according to standard protocol (see Definitions: RACE). The complete sequence was assembled from both the amplified fragment, 5'RACE- and 3'-RACE products. Finally, the PCR primers: 5'-CTAATACGACATACCAACAACTG-CAG-3' (SEQ ID No: 45) and 5'-CTCGCT-TGAATTTGTTTGTACATG-3' (SEQ ID No: 46) derived from the assembled sequence, were used to amplify the entire soybean NFR5 gene as a single nucleic acid molecule from genomic DNA of *Glycine max* "Stevens" and shown to have the sequence of SEQ ID No: 48.

Bean NFR5 gene orthologue from *Phaseolus vulgaris* "Negro jamapa" encodes an NFR5 protein orthologue with an amino acid sequence having SEQ ID No: 40. Soybean NFR5 gene orthologue from *Glycine max* "Stevens" encodes an NFR5 protein orthologue with an amino acid sequence having SEQ ID No: 48. An alignment of the amino acid sequence of NFR5 orthologues encoded by the NFR5 gene orthologues isolated from *Lotus japonicus, Glycine max* and *Phaseolus vulgaris* is shown in Table 1. All three protein share the common features of three LysM domains, a transmembrane domain and an intracellular protein kinase domain, while kinase domain VII is lacking and domain VIII is highly divergent or absent.

The pairwise amino acid sequence similarity between the *Lotus* and Glycine NFR5 protein orthologues, and between the *Lotus* and *Phaseolus* NFR5 proteins orthologues is about 80% and about 86% respectively, while pairwise the nucleic acid sequence similarity between *Lotus* NFR5 gene and Glycine NFR5 and the *Lotus* and *Phaseolus* NFR5 gene orthologues is about 73% and about 70% respectively (Table 2).

7. The NFR5 Protein Family is Unique to Nodulating Plants

Comparative analysis defines LjNFR5 and PsSYM10 as members of a novel family of transmembrane Nod-factor binding proteins. A BLAST search of plant gene sequences suggests that genes encoding related, but presently uncharacterised, proteins may be present in the legume *Medicago truncatula* (Ac126779; FIGS. 2 and 3), while more distantly related, predicted proteins may be found in rice (Ac103891) and *Arabidopsis* (At2g33580), with a sequence identity to NFR5 of 61%, 39%, and 28%, respectively. The high level of sequence conservation in *M. truncatula* (Ac126779) makes this protein and the gene encoding the protein substantially identical to NFR5. In common with the NFR5 and SYM10, the kinase domains of these proteins also lack the conserved aspartic acid residue of motif VII, and the activation loop in motif VII is highly diverged or absent, as shown in FIG. 2d, with the exception of the *Arabidopsis* protein. Only distantly related proteins are therefore found outside the legume family. In conclusion, the NFR5 protein family appears to be restricted to nodulating legumes, and its absence from other plant families may be a key limiting factor in the establishment of rhizobial-root interactions in the members of the families.

8. Tissue Specific Expression of the LjNFR5 and PsSYM10 Genes

The expression pattern of the NFR5 and SYM10 genes in *Lotus* and pea is consistent with the role of their gene products as transmembrane Nod-factor binding proteins in the perception of rhizobial Nod-factors at the root surface and later during tissue invasion.

The expression of the NFR5 and SYM10 genes in various isolated organs of *Lotus* and pea plants, was investigated by determining the steady state NFR5 and SYM10 mRNA levels using Real-time PCR and/or Northern blot analysis. Total RNA was isolated from root, leaf, flower, pod and nodule tissues of uninoculated or inoculated *Lotus* "Gifu" or pea plants using a high salt extraction buffer followed by purification through a CsCl cushion. For Northern analysis, according to standard protocols, 20 µg total RNA was size-fractionated on 1.2% agarose gel, transferred to a Hybond membrane, hybridised overnight with an NFR5 or SYM10 specific probe covering the extracellular domain and washed at high stringency. Hybridization to the constitutively expressed ubiquitin UBI gene was used as control for RNA loading and quality of the RNA.

For the quantitative real-time RT-PCR, total RNA was extracted using the CsCl method and the mRNA was purified by biomagnetic affinity separation (Jakobsen, K. S. et al (1990) Nucleic Acids Research 18(12): 3669). The RNA preparations were analysed for contaminating DNA by quantitative PCR and when necessary, the RNA was treated with DNaseI. The DNaseI enzyme was then removed by phenol:chloroform extraction and the RNA was precipitated and re-suspended in 20 µl RNase free $H_2O$. First strand cDNA was prepared using Expand reverse transcriptase and the quantitative real-time PCR was performed on a standard PCR LightCycler instrument. The efficiency-corrected relative transcript concentration was determined and normalized to a calibrator sample, using *Lotus japonicus* ATP synthase gene as a reference (Gerard C. J. et al, 2000 *Mol. Diagnosis.* 5: 39-45).

Figure 4:
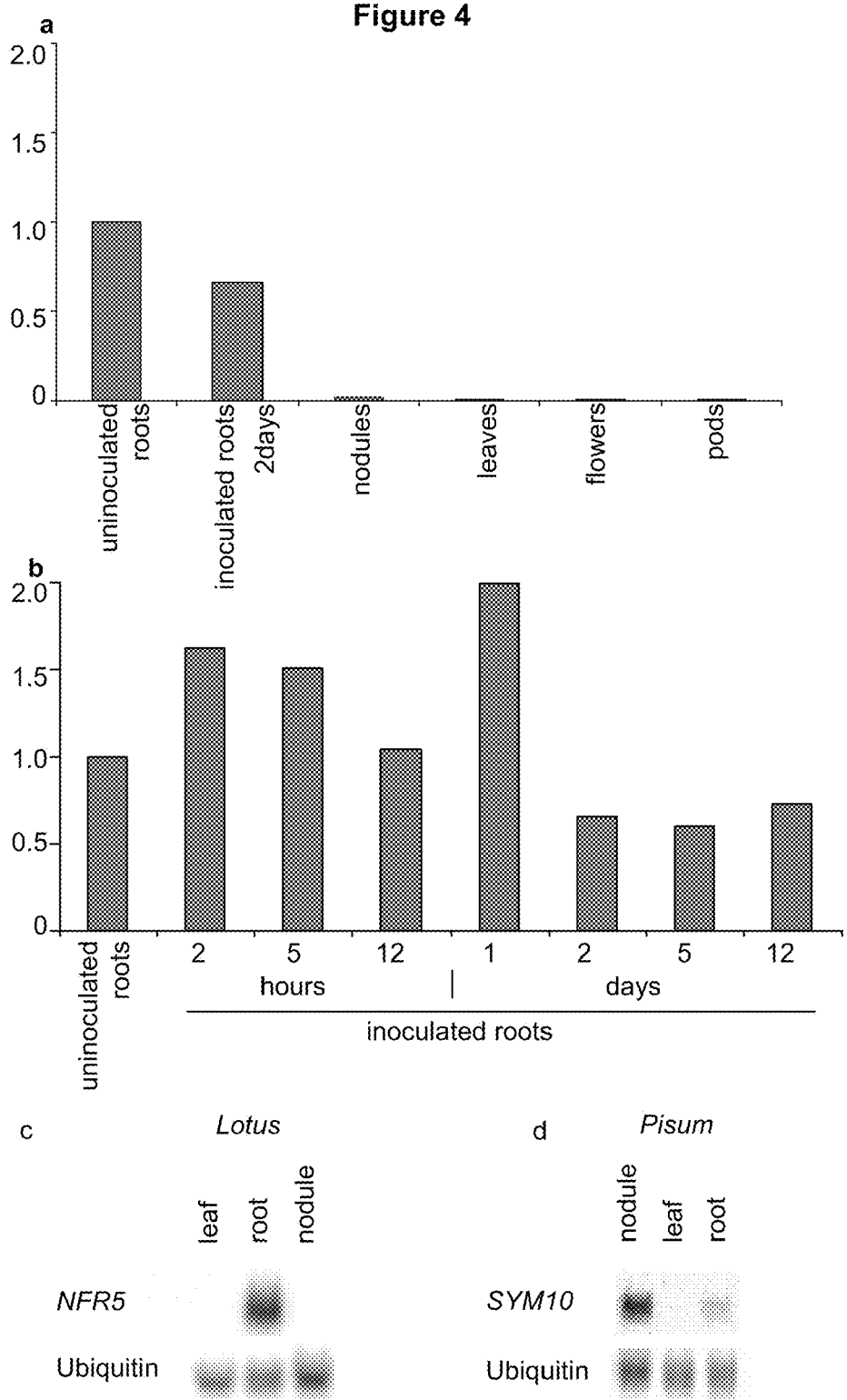
FIG. 4. Steady-state levels of LjNFR5 and PsSYM10 mRNA. a. NFR5 mRNA detected in uninoculated roots, inoculated roots, nodules, leaves, flowers and pods of Lotus plants. b. Time course of NFR5 mRNA transcript accumulation in roots after inoculation with M. loti. The identity of the amplified transcripts was confirmed by sequencing. ATPase was used as internal control and relative normalised values compared to uninoculated roots are shown. c. Northern analysis showing NFR5 mRNA expression in nodule leaf and root of symbiotically and non-symbiotically grown Lotus plants. d. Northern analysis showing Sym10 mRNA expression in leaf, root and nodule of symbiotically and non-symbiotically grown pea plants.

The level of NFR5 mRNA, determined by Northern blot analysis and quantitative RT-PCR, was 60 to 120 fold higher in the root tissue of *Lotus* plants in comparison to other plant tissues (leaves, stems, flowers, pods, and nodules), as shown in FIG. 4a. Northern hybridisation show highest expression of NFR5 in *Lotus* root tissue and a barely detectable expression in nodules. Northern blot analysis detected SYM10 mRNA in the roots of pea, and a higher level in nodules, but no mRNA was detected in leaves, as shown in FIG. 4c.

B. Isolation, Cloning and Characterisation of NFR1 Genes and Gene Products.

1. Map Based Cloning of Lj NFR1

Figure 5:
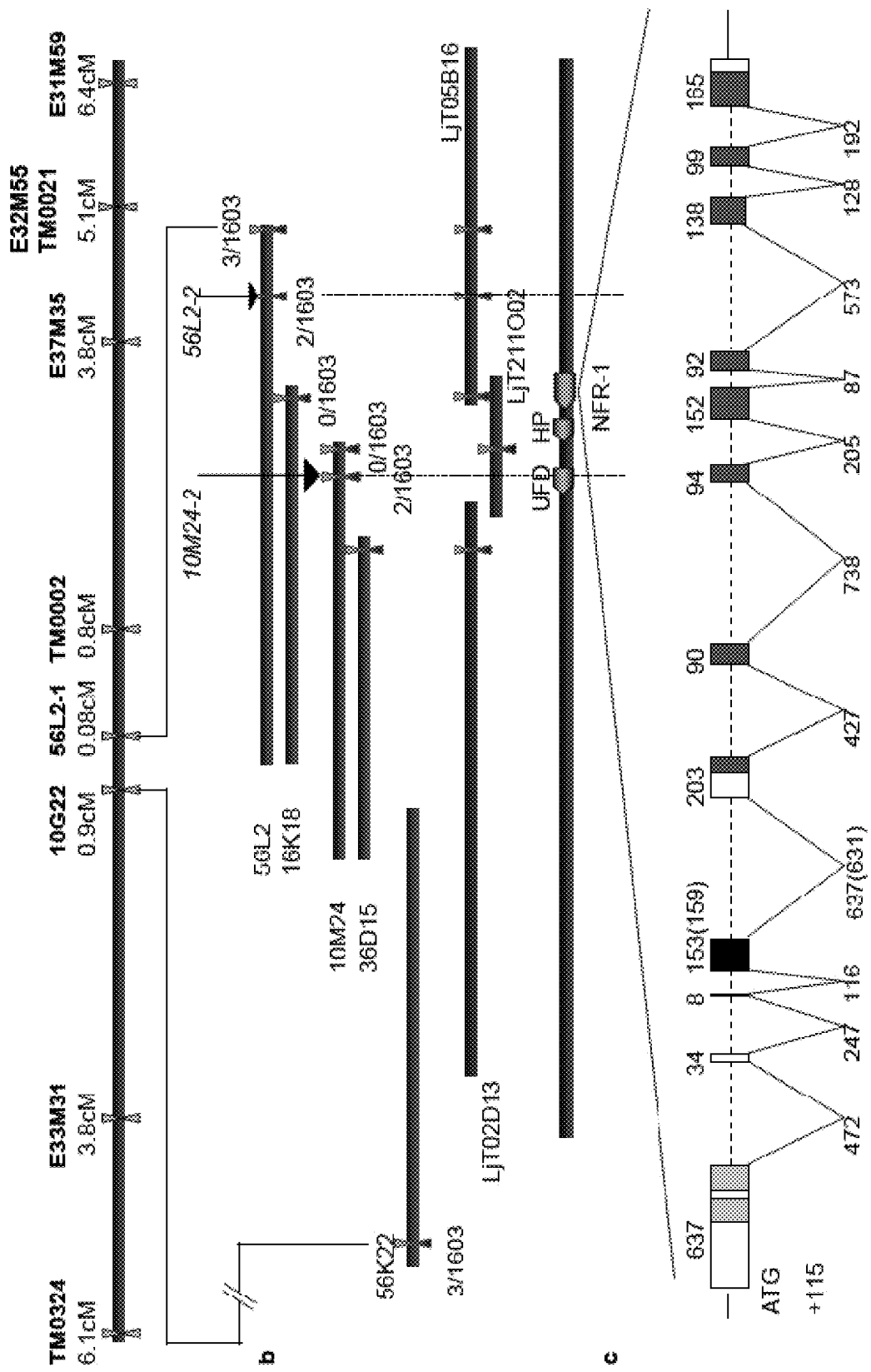
FIG. 5. Positional cloning of the NFR1 gene. a. Genetic map of the region surrounding the NFR1 locus. Positions of the closest AFLP, microsatelitte- and PCR-markers are given together with genetic distances in cM. b. Physical map of the NFR1 locus. BAC clones 56L2, 16K18, 10M24, 36D15, 56K22 and TAC clones LjT05B16, LjT02D13, LjT211O02, which cover the region are shown. The numbers of recombination events detected with BAC and TAC end-markers or internal markers are given. Arrows indicate the positions of the two markers (10M24-2, 56L2-2) delimiting the NFR1 locus. UFD and HP correspond to the UFD1-like protein and the hypothetical protein encoded in the region. c. Exon-intron structure of the NFR1 gene. Boxes correspond to exons, where LysM motifs are shown in stippled boxes, trans-membrane region in black, kinase domains in hatched boxes. Dotted lines define introns and full lines define the 5' and 3' un-translated regions. The nucleotide length of all exons and introns are indicated. The numbers between brackets correspond to exon and intron 4, corresponding to alternative splicing.

The NFR1 gene was isolated using a positional cloning approach. On the genetic map of *Lotus* the NFR1 locus is located on the short arm of chromosome I, approximately 22 cM from the top, within a 7.6 cM interval, as shown in FIG. 5a. Several TM markers and PCR markers, derived from DNA polymorphism in the genome sequences of the *L. japonicus* mapping parents, were found to be closely linked to NFR1 locus and were used to narrow down the region. A physical map of the region, comprising a contig of assembled BAC and TAC clones, is shown in FIG. 5b. Fine mapping in an F2 population, established from a *Lotus japonicus* nfr-1 mutant to wild type *L. japonicus* ecotype 'Miyakojima MG-20' cross, and genotyping of 1603 mutant plants, identified two markers (56K22, 56L2-2) delimiting the NFR1 locus within a region of 250 kb. BAC and TAC libraries, available from Satoshi Tabata, Kazusa DNA Research Institute, Kisarazu, Chiba 292-0812 Japan; another BAC library from Jens Stougaard, Department of Molecular Biology, University of Aarhus, Gustav Wieds Vej 10, DK-8000 Aarhus C, were screened using the closest flanking markers (56L2-1, 10M24-1, 36D15) as probes, and the NFR1 locus was localised to 36 kb within the region. The ORFs detected within the region coded for a UFD1-like protein, a hypothetical protein and a candidate NFR1 protein showing homology to receptor kinases, (FIG. 5b).

The region in the genomes of nfr1-1, nfr1-2 mutants, corresponding to the candidate NFR1 gene was amplified as three fragments by PCR under standard conditions and sequenced. The fragment of 1827 bp amplified using PCR forward primer 5'TGC ATT TGC ATG GAG MC C3', (SEQ ID No: 16) and reverse primer 5' TTT GCT GTG ACA TTA TCA GC3', (SEQ ID No: 17) contains single nucleotide substitutions leading to translational stop codons in both the mutant alleles nfr1-1, with a CAA to TAA substitution, and the nfr1-2, with a GAA to TAA substitution. The physical and genetic mapping of the nfr1 locus, combined with the identification of mutations in two independent nfr1 mutant alleles, provides unequivocal evidence that the sequenced NFR1 gene is required for Nod-factor perception and subsequent signal transduction.

2. Cloning the Lj NFR1 cDNAs

Two alternatively spliced Lj NFR1 cDNAs were identified using a combination of cDNA library screening and 5' RACE on root RNA from *Lotus japonicus*. A *Lotus* root cDNA library (Poulsen et al., 2002, *MPMI* 15:376-379) was screened with an NFR1 gene probe generated by PCR amplification of the nucleotides between 9689 to 10055 of the genomic sequence, using the primer pair: 5' TTGCAGATTG-CACAACTAGG3' (SEQ ID No: 18) and 5'ACTTAGAATCT-GCAACTTTGC 3' (SEQ ID No: 19). Total RNA extracted from *Lotus* roots, was amplified by 5' RACE, according to the standard protocol, using the gene specific reverse primer 5'ACTTAGAATCTGCAACTTTGC 3' (SEQ ID No 20). Based on the sequence of isolated NFR1 cDNAs and 5' RACE products, the NFR1 gene produces two mRNA species, of 2187 (SEQ ID No: 21) and 2193 nucleotides (SEQ ID No: 22), with a 5' leader sequence of 114 nucleotides, and a 3' untranslated region is 207 nucleotides (FIG. 5c). Alignment of genomic and cDNA sequences defined 12 exons in NFR1 and a gene structure spanning 10235 bp (SEQ ID No: 23). The sequenced region includes 4057 bp from the stop codon of the previous gene up to the transcription start point of NFR1+ 6009 bp of NFR1+187 bp of 3' genomic. Alternative splice donor sites at the 3' of exon IV account for the two alternative NFR1 mRNA species.

3. Primary Sequence and Structural Domains of LjNFR1 and Mutant Alleles.

The primary sequence and domain structure of NFR1, encoded by LjNFR1, are consistent with a transmembrane Nod-factor binding protein, required for Nod-factor perception in *Rhizobium*-legume symbiosis. The alternatively spliced NFR1 cDNAs encode NFR1 proteins of 621 (SEQ ID No: 24) and 623 amino acids (SEQ ID No: 25), with a predicted molecular mass of 68.09 kd and 68.23 kd, respectively. The protein has an amino-terminal signal peptide, followed by an extracellular domain having two LysM-type motifs, a transmembrane domain, and an intracellular carboxy-terminal domain comprising serine/threonine kinases motifs In nfr1-1, a stop codon in kinase domain VIII encodes truncated polypeptides of 490 and 492 amino acids, and in nfr1-2 a stop codon between domain IX and XI encodes truncated polypeptides of 526 and 528 amino acids, as indicated in FIG. 6a.

In FIG. 6b the M1 LysM motif of NFR1 is aligned with the LysM motifs from *Arabidopsis thaliana* and the SMART consensus and M2 LysM of NFR1 with the *Volvox carteri* chitinase (Acc No: T08150), the closest related *Arabidopsis thaliana* receptor kinase (Acc No: NP_566689), the rice (Acc No: BAB89226) and the consensus SMART LysM motif.

4. Isolation of NFR1 Gene Orthogues Encoding NFR1 Protein Orthogues

Two nucleic acid molecules have been isolated from a *Pisum sativum* cv Finale (pea) root hair cDNA library, that comprise two cDNA molecules encoding NFR1A and NFR1B protein orthologues. The pea cDNA library was screened by hybrisation at medium stringency (see Definitions: Southern hybridisation) using a *Lotus* NFR1 gene probe, comprising the coding region for the extracellular domain of *Lotus* NFR1. This NFR1 gene specific probe was amplified from the *Lotus* NFR1 coding sequence by PCR using the primers: 5'-TAATTATCAGAGTMGTGTGAC-3' (SEQ ID No: 49) and 5'-AGTTACCCACCTGTGGTAC-3' (SEQ ID No. 50).

The two cDNA clones *Pisum sativum* NFR1A (SEQ ID No: 51) and *Pisum sativum* NFR1B (SEQ ID No: 53) encode the orthologues NFR1A (SEQ ID No: 52) and NFR1B (SEQ ID No: 54) respectively. An alignment of the amino acid sequence of the three NFR1 orthologues from *Lotus* and *Pisum sativum* is shown in Table 3. All three protein share the common features of LysM domains, a transmembrane domain and an intracellular protein kinase domain, while kinase domain VII is lacking and domain VIII is highly divergent or absent. The nucleic acid sequence of the *Pisum* and *Lotus* NFR1 orthologues show close similarity (about 83%), as do their respective encoded proteins (about 73%) as shown in Table 4.

4. The LjNFR1 Protein Family is not Found in Non-nodulating Plants

Comparative analysis defines LjNFR1 as a member of a second novel family of transmembrane Nod-factor binding proteins. Although proteins having both receptor-like kinase domains and LysM motifs are predicted from plant genome sequences, their homology to NFR1 is low and their putative function unknown. *Arabidopsis* has five predicted receptor-like kinases with LysM motifs in the extracellular domain, and one of them (At3g21630) is 54% identical to NFR1 at the protein level. Rice has 2 genes in the same class, and one (BAB89226) encodes a protein with 32% identity to NFR1. This suggests that the NFR1 protein is essential for Nod-factor perception and its absence from non-nodulating plants may be a key limiting factor in the establishment of rhizobial-root interactions in these plants. Although NFR1 shares the same domain structure to NFR5 their primary sequence homology is low (FIG. 11).

5. Expression of the LjNFR1, NFR5 and SymRK Symbiotic Genes is Root Specific and Independently Regulated.

Figure 7:
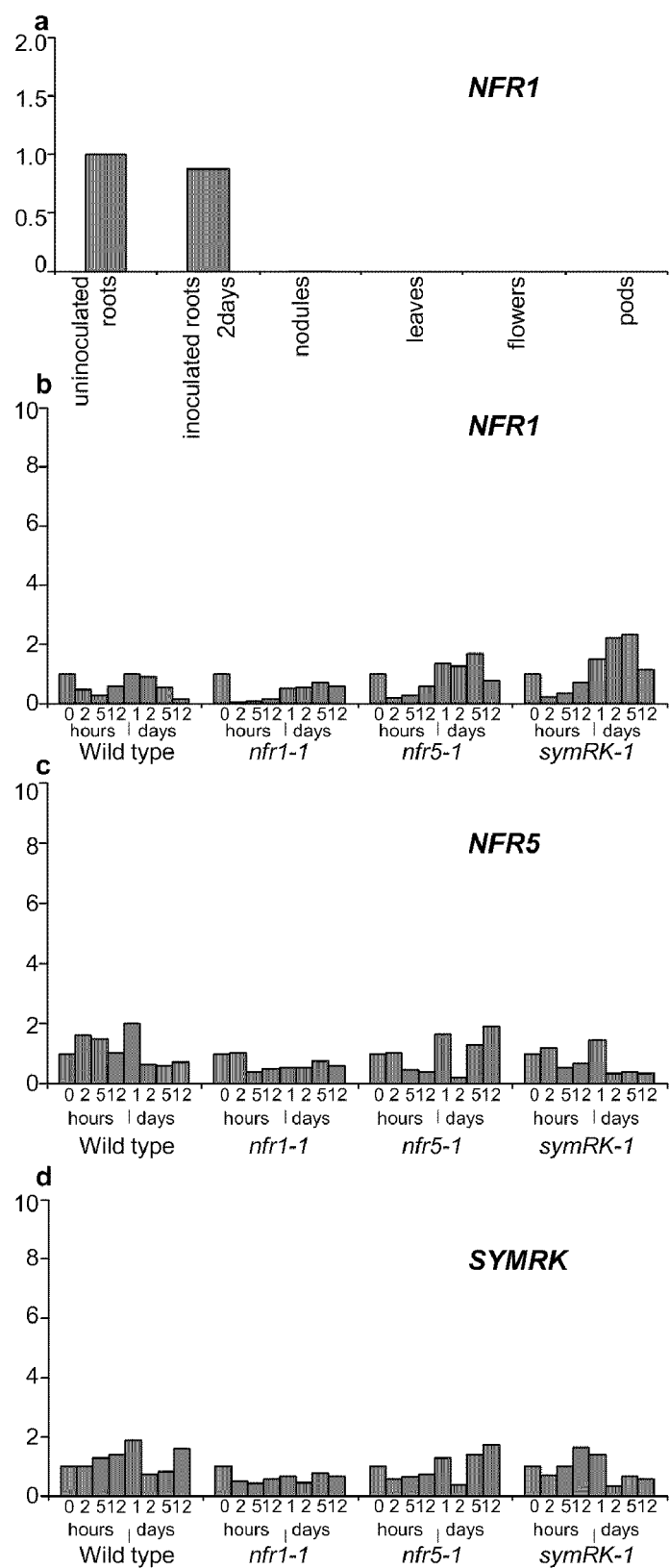
FIG. 7. NFR1, NFR5 and SymRK gene expression. a. Transcript levels of NFR1 in uninoculated, inoculated roots, nodules, leaves, flowers and pods of wild type plants. b. Transcript levels of NFR1 in wild type, nfr1, nfr5 and symRK mutant plants after inoculation with M. loti. c. Transcript levels of NFR5 in wild type, nfr1, nfr5 and SymRK mutant plants after inoculation with M. loti. d. Transcript levels of SYMRK in wild type, nfr1, nfr5 and symRK mutant plants after inoculation with M. loti. Transcript levels were measured by quantitative PCR. ATPase was used as internal control and relative values normalised to the untreated roots (zero hours) are shown.

The NFR1 dependent root hair curling, in the susceptible zone located just behind the root tip, is correlated with root specific NFR1 gene expression. Steady-state NFR1 mRNA levels were measured in different plant organs using quantitative real-time PCR and Northern blot analysis as described above in section A.7. NFR1 mRNA was only expressed in root tissue, and remained below detectable levels in leaves, flowers, pods and nodules, as shown in FIG. 7a. Upon inoculation with *M. loti*, the expression of NFR1 in wild type plants is relatively stable for at least 12 days after inoculation (FIG.

7b). Real-time PCR experiments revealed no difference between the levels of the two NFR1 transcripts detected in the root RNA, suggesting that the alternative splicing of exon 4 is not differentially regulated. NFR1, NFR5 and SymRK gene expression in roots, before and following *Rhizobium* inoculation, was determined by real-time PCR in wild type and nfr1, nfr5 and symrk mutant genotypes. The expression of NFR1, NFR5 and SymRK genes in un-inoculated and inoculated roots was not significantly influenced by the symbiotic mutant genotype (FIGS. 7b, c, d) indicating that transcriptional regulation of these genes is mutually independent.

Example 2

Functional Properties of the Nod-factor Binding Element and Its Component NFR Proteins The functional and regulatory properties of the Nod-factor binding element and its component NFR proteins provide valuable tools for monitoring the functional expression and specific activity of the NFR proteins. Nod-factor perception by the Nod-factor binding element triggers the rhizobial-host interaction, which includes depolarisation of the plasma membrane, ion fluxes, alkalization of the external root hair space of the invasion zone, calcium oscillations and cytoplasmic alkalization in epidermal cells, root hair morphological changes, infection thread formation and the initiation of the nodule primordia. These physiological events are accompanied and coordinated by the induction of specific plant symbiotic genes, called nodulins. For example, the NIN gene encodes a putative transcriptional regulator facilitating infection thread formation and inception of the nodule primordia and limits the region of root cell-rhizobial interaction competence to a narrow invasion zone (Geurts and Bisseling, 2002, supra). Since nin mutants develop normal mycorrhiza, the NIN gene lies in the *rhizobia*-specific branch of the symbiotic signalling pathway, downstream of the common pathway. Ion fluxes, pH changes, root hair deformation and nodule formation are all absent in NFR1 and NFR5 mutant plants, and hence the functional activity of these genes must be required for all downstream physiological responses. Several physiological and molecular markers that are diagnostic of NFR expression are provided below.

1. Morphological Marker of NFR1 and NFR5 Gene Expression

When wild type *Lotus japonicus* plants are inoculated with *Mesorhizobium loti*, the earliest visible evidence of infection is root hair deformation and root hair curling, which occurs 24 hours after inoculation, as shown in FIG. 8a. However, mutant plants carrying the nfr1-1 (FIG. 8c), nfr1-2, nfr5-1, nfr 5-2 or nfr5-3 alleles (as in FIG. 8c), all failed to produce root hair curling or deformation, infection threads or nodule primordia in response to infection by *Mesorhizobium loti* with all three strains tested (NZP2235, R7A and TONO). Lipochitin-oligosaccharides purified from *M. loti*, R7A strain, which induce root hair deformation and branching in wild type plants (FIG. 8b), also failed to induce any deformation of root hairs of the nfr1-1 and nfr5-1 mutants (FIG. 8d), evidencing the key role of the NFR1 and NFR5 genes in Nod-factor perception.

Mutations in genes expressing the downstream components of the symbiosis signalling pathway, namely symRK and nin have clearly distinguishable phenotypes. After infection with *Mesorhizobium loti*, the root hairs of symRK plants swell into balloon structures (FIG. 8e), while the nin mutants produce an excessive root hair response (FIG. 8g). The response of double mutants carrying nfr1-1/symRK-3 mutant alleles or nfr1-1/nin alleles to *Mesorhizobium loti* infection (FIGS. 8f,h) are similar to that of nfr1-1 mutants, demonstrating that the nfr1-1 mutation is dominant to symRK and nin mutations, and hence determines an earlier step in the symbiotic signalling pathway.

2. Physiological Marker of NFR1 and NFR5 Gene Expression

Figure 9:
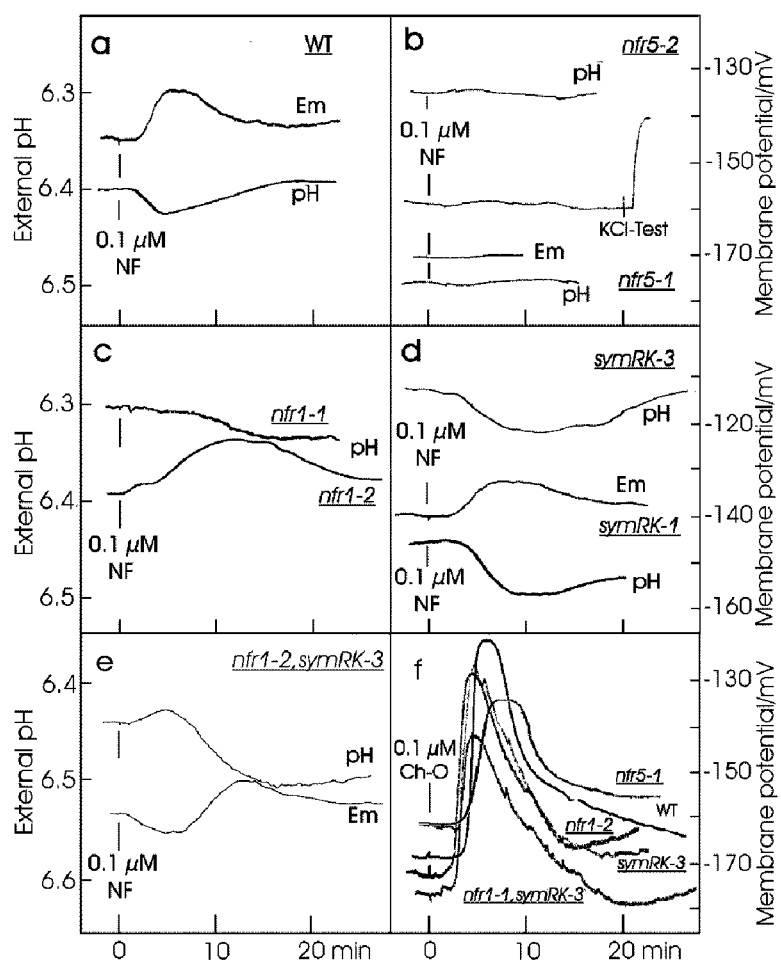
FIG. 9. Membrane depolarisation and pH changes in the extracellular root hair space after application of Nod-factor purified from *M. loti*. Influence of 0.1 µM Nod-factor (NF) on membrane potential (Em) and/or external pH (pH) of a. *Lotus* wild type b. nfr5-1 and nfr5-2 mutants c. nfr1-1 and nfr1-2 mutants d. symRK-1 and symRK-3 mutants e. nfr1-2, symRK-3 double mutant, f. pH changes in the extracellular root hair space after application of an undecorated chito-octaose.

When the root hairs of wild type *Lotus* plants are exposed to *M. loti* Nod-factor, the plasma membrane is depolarised and an alkalisation occurs in the root hair space of the invasion zone, (FIG. 9a). The extracellular pH was monitored continuously in a flow-through regime using a pH-selective microelectrode, placed within the root hair space. Membrane potential was measured simultaneously with pH, and the calculated values are based on at least three equivalent experiments, each. Mutants carrying nfr1 and nfr5 alleles do not respond normally to Nod-factor stimulation. Two nfr5 alleles abolish the response to Nod-factors (FIG. 9b), while the nfr1-1 allele causes a diminished and slower alkalisation, and the nfr1-2 allele causes the acidification of the extracellular root hair space (FIG. 9c). Both the NFR1 and NFR5 genes are thus essential for mounting the earliest detectable cellular and electrophysiological responses to Nod-factor, which can be used to monitor their functional activity.

The early physiological response of the symRK-3 and symRK-1 mutant plants to *Mesorhizobium loti* Nod-factor is similar to the wild type (FIG. 9d) and clearly distinguishable from the response of both the nfr1 and nfr5 mutants.

The response of the double mutant, carrying nfr1-2/symRK-3 mutant alleles, to Nod-factor (FIG. 9e) is similar to that of nfr1-2 mutants, further supporting that the nfr1-2 mutation is dominant to symRK-3 and determines an earlier step in the symbiotic signalling pathway.

3. NFR1 and NFR5 Mediated Nod-factor Perception Lies Upstream of NIN and ENOD and is Required for Their Expression.

The symbiotic expression of the nodulin genes, *Lotus japonicus* ENOD2 (Niwa, S. et al., 2001 *MPMI* 14:848-56) and NIN, in roots following rhizobial inoculation, provides a marker for NFR gene expression. The steady-state levels of NIN and ENOD2 mRNA were measured in roots before and following rhizobial inoculation by quantitative real-time PCR, using the primer pairs:

5'AATGCTCTTGATCAGGCTG3' (SEQ ID No: 26) and
5'AGGAGCCCAAGTGAGTGCTA3' (SEQ ID No: 27) for amplification of NIN mRNA reverse transcripts; and the primer pairs:
5'CAG GAA AAA CCA CCA CCT GT3' (SEQ ID No:28) and
5'ATGGAGGCGMTACACTGGTG3' (SEQ ID No: 29) for amplification of ENOD2 mRNA reverse transcripts. The identity of the amplified sequences was confirmed by sequencing.

Figure 8:
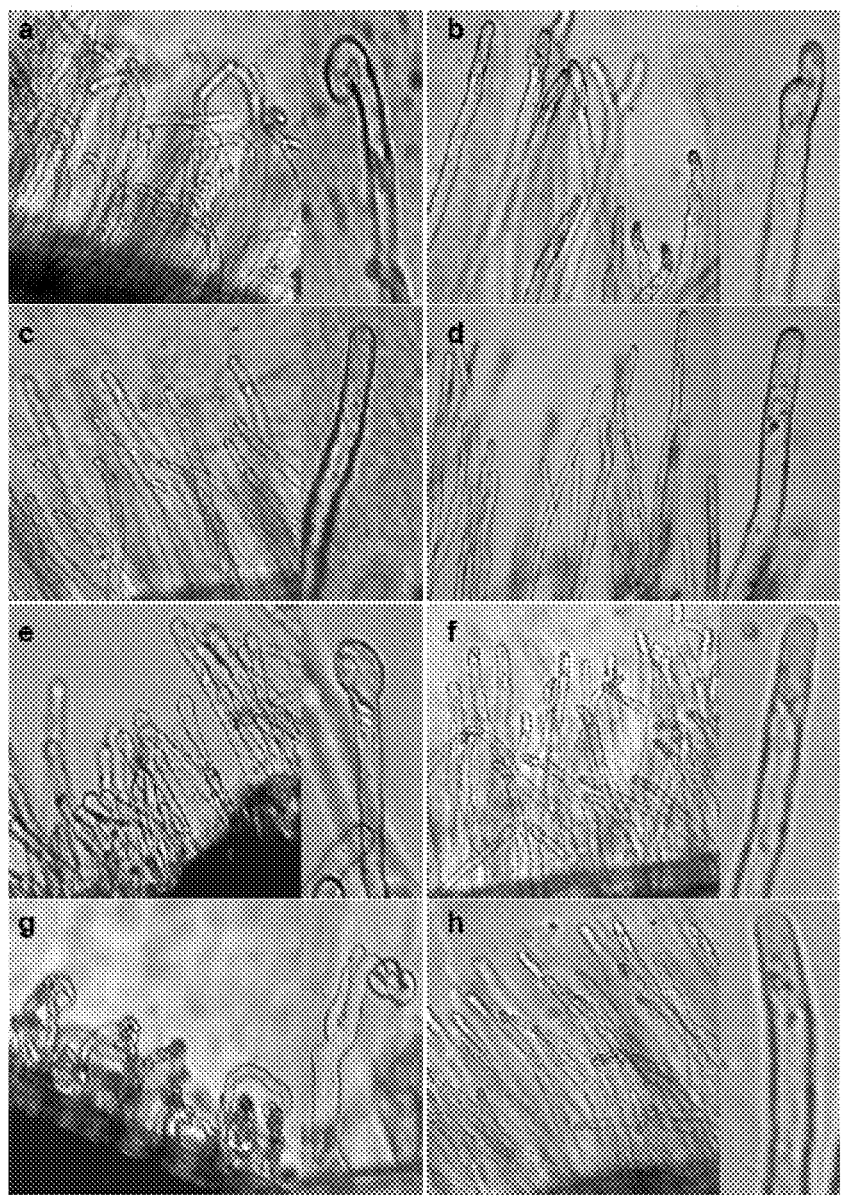
FIG. 8. Root hair response after inoculation with M. loti or Nod-factor application. a. Wild type root hair curling on seedlings inoculated with M. loti. b. Root hair deformations on wild type seedlings after Nod-factor application. c. Root hairs on nfr1-1 seedlings inoculated with M. loti. d. Root hairs on nfr1-1 seedlings after Nod-factor application. e. Root hairs with balloon deformations on symRK-3 mutants inoculated with M. loti. f. Roots hairs on a nfr1-1, symRK-3 double mutant inoculated with M. loti g. Excessive root hair response on nin mutants inoculated with M. loti. h. Root hairs on a nfr1-1, nin double mutant inoculated with M. loti. Root hairs on nfr5-1 seedlings inoculated with M. loti, nfr5-1 seedlings after Nod-factor application, untreated nfr5-1 control, untreated wild type control, untreated nfr1-1 control, are indistiguisable from the straight roots hairs shown in c, d, f, h and therefore not shown. Inserts to the right of a to h show a close-up of the root hairs.
Figure 10:
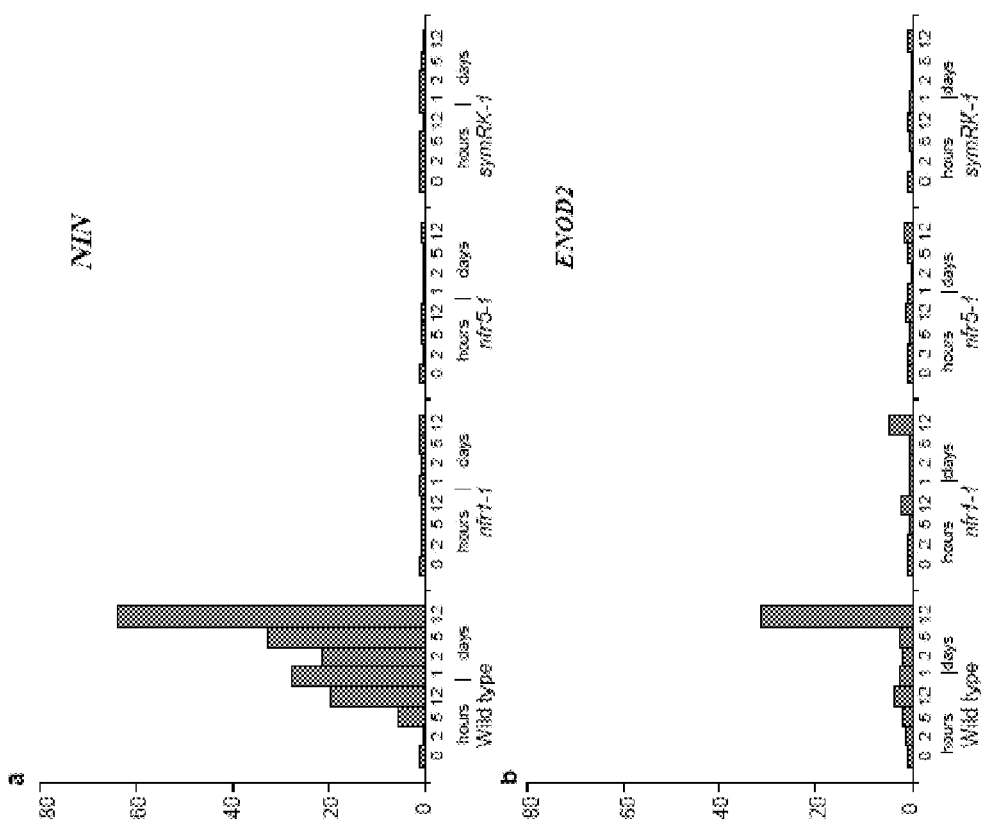
FIG. 10. Expression of the NIN and ENOD2 genes in wild type, nfr1 and nfr5 mutant genotypes. a. NIN transcript level in RNA extracted from roots two hours to 12 days after *M. loti* inoculation. b ENOD2 transcript level in RNA extracted from roots two hours to 12 days after *M. loti* inoculation. Transcript levels were measured by quantitative PCR and the identity of the amplified sequences was confirmed by sequencing. ATPase was used as internal control and relative values normalised to the untreated root (zero hours) are shown.

Five hours after inoculation, induction of NIN gene expression was detected in the wild type plants, while induction of ENOD2 occurs after 12 days as shown in FIGS. 10a and b. In the nfr1 and nfr5 mutants, activation of NIN and ENOD2 was not detected, demonstrating that functional NFR1 and NFR5 genes can be monitored by the activation of these early nodulin genes. *Lotus* plants transformed with a NIN gene promoter region fused to a GUS reporter gene provide a further tool to monitor NFR gene function. Expression of the NIN-GUS reporter can be induced in root hairs and epidermal cells of the root invasion zone following rhizobial inoculation in transformed wild-type plants. In contrast expression of the NIN-GUS reporter in an nfr1 mutant was not detected following rhizobial inoculation. Likewise, NIN-GUS expression was induced in the invasion zone of wildtype plants after Nod-factor application, while in a nfr1 mutant background no expression was detected The requirement for NFR1 function was confirmed in nfr1-1, nin double mutants by the absence of root hair curling and excessive root hair curling (FIG. 8).

The LjCBP1 gene, T-DNA tagged with a promoter-less GUS in the T90 line, is rapidly activated after *M. loti* inoculation as seen for NIN-GUS, thus providing an independent and sensitive reporter of early nodulin gene expression (Webb et al, 2000, Molecular Plant-Microbe Interact. 13, 606,-616). Parallel experiments comparing expression of the LjCBP1 promoter GUS fusion in wt and nfr1 mutant background confirm the requirement for a functional NFR1 for activation of the early response to bacteria and Nod-factor.

Example 3

Transgenic Expression of NFR Polypeptides and Complementation of the nfr Mutants The NFR genes, encoding the NFR1 and NFR5 protein components of the Nod-factor binding element, can each be stably integrated, as a transgene, into the genome of a plant, such as a non-nodulating plant or a mutant non-nodulating plant, by transformation. Expression of this transgene, directed by an operably linked promoter, can be detected by expression of the respective NFR protein in the transformed plant and functional complementation of a non-nodulating mutant plant.

A wildtype NFR5 transgene expression cassette of 3.5 kb, comprising a 1175 bp promotor region, the NFR5 gene and a 441 bp 3' UTR was cloned in a vector (pIV10), and the vector was recombined into the T-DNA of *Agrobacterium rhizogenes* strain AR12 and AR1193 by triparental mating. The NFR5 expression cassette in pIV10 was subsequently transformed into non-nodulating *Lotus* nfr5-1 and nfr5-2 mutants via *Agrobacterium rhizogenes*-mediated transformation according to the standard protocol (Stougaard 1995, Methods in Molecular Biology volume 49, Plant Gene Transfer and Expression Protocols, p 49-63) In parallel, control transgenic *Lotus* nfr5-1 and nfr5-2 mutants plants were generated, which were transformed with an empty vector, lacking the NFR5 expression cassette.

The nodulation phenotype of the transgenic hairy root tissue of the transformed mutant *Lotus* plants was scored after inoculation with *Mesorhizobium loti* (*M. loti*) strain NZP2235. In planta complementation of the nfr5-1 and nfr5-2 mutants by the NFR5 transgene was accomplished, as shown in Table 6, with an efficiency of ≦58%, and the establishment of normal rhizobial-legume interactions and development of nitrogen fixing nodules. Complementation was dependent on transformation with a vector comprising the NFR5 expression cassette.

A transgene expression cassette, comprising the wild type NFR1 gene comprising 3020 bp of promoter region, the NFR1 ORF and 394 bp of 3'untranslated region, was cloned into the pIV10 vector and recombined into *Agrobacterium rhizogenes* strain AR12 and AR1193 by triparental mating. *Agrobacterium rhizogenes*-mediated transformation was used to transform the gene into non-nodulating *Lotus* nfr1-1 and nfr1-2 mutants in parallel with a control empty vector. In planta complementation of the *Lotus* nfr1-1 and nfr1-2 mutants by the NFR1 transgene was accomplished, as shown in Table 7, with an efficiency of ≦60%, and the establishment of normal *Rhizobium*-legume interactions with *M. loti* strain NZP2235, and development of nitrogen fixing nodules. Complementation was dependent on transformation with a vector comprising the NFR1 expression cassette Example 4

Expression and Characterisation of the NFR1, NFR5 and SYM10 Proteins in Transgenic Plants NFR1, NFR5 and SYM10 proteins are expressed and purified from transgenic plants, by exploiting easy and well described transformation procedures for *Lotus* (Stougaard 1995. supra) and tobacco (Draper et al. 1988, Plant Genetic Transformation and Gene Expression, A Laboratory Manual, Blackwell Scientific Publications). Expression in plants is particularly advantageous, since it facilitates the correct folding of these transmembrane proteins and provides for correct post-translational modification, such as phosphorylation. The primary sequences of the expressed proteins are extended with commercially available epitope tags (Myc or FLAG), to allow their purification from plant protein extracts. DNA sequences encoding the tags are ligated into the expression cassette for each protein, in frame, either at the 5' or the 3' end of the cDNA coding region. These modified coding regions are then operably linked to a promoter, and recombined into *Agrobacterium rhizogenes*. *Lotus* is transformed by wound-site infection and from the transgenic roots independent root cultures are established in vitro (Stougaard 1995, supra). NFR1, NFR5 and SYM10 proteins are then purified from root cultures by affinity chromatography using the epitope specific antibody and standard procedures. Alternatively the proteins are immunoprecipitated from crude extracts or from semi-purified preparations. Proteins are detected by Western blotting methods. For transformation and expression in tobacco, the epitope tagged cDNAs are cloned into an expression cassette comprising a constitutively expressed 35S promoter and a 3'UTR and subsequently inserted into binary vectors. After transfer of the binary vector into *Agrobacterium tumefaciens*, transgenic tobacco plants are obtained by the transformation regeneration procedure (Draper et al. 1988, supra). Proteins are then extracted from crude or semi-purified extracts of tobacco leaves using affinity purification or immunoprecipitation methods. The epitope tagged purified protein preparations are used to raise mono-specific antibodies towards the NFR1, NFR5 and SYM10 proteins Example 5

Plant Breeding Tools to Select for Enhanced Nodulation Frequency and Efficiency

A successful and efficient primary interaction between a rhizobial strain and its host depends on detection of a *Rhizobium* strain's unique Nod-factor (LCO) profile by the plant host. The Nod-factor binding element and its component NFR proteins, each with their extracellular LysM motifs, play a key role in controlling this interaction. NFR alleles, encoding variant NFR proteins are shown to be correlated with the efficiency and frequency of nodulation with a given rhizobial strain. Molecular breeding tools to detect and distinguish different plant NFR alleles, and assays to assess the nodulation efficiency and frequency of each allele, provides an effective method to breed for nodulation efficiency and frequency.

Methods useful for breeding for nodulation efficiency and frequency are given below, and the application of these techniques is illustrated for the NFR alleles of *Lotus* spp. Using the *Rhizobium leguminosarum* by viceae 5560 DZL strain (Bras et al, 2000, Molecular Plant-Microbe Interact. 13, 475-479) it is documented that the host range of this strain within the *Lotus* spp depends on the NFR1 and NFR5 alleles present in the *Lotus* host. When inoculated onto wild type plants *Rhizobium leguminosarum* by viceae 5560 DZL form root nodules on *Lotus japonicus* GIFU but the strain is unable to form root nodules on *Lotus filicaulis*. Transgenic *L. filicaulis* transformed with the *Lotus japonicus* GIFU NFR1 and NFR5 alleles do however form root nodules when inoculated with the *Rhizobium leguminosarum* by viceae 5560 DZL strain proving the NFR1/NFR5 allele dependent Nod-factor recognition.

1. Determining the Nod-factor Specificity and Sensitivity of NFR Alleles.

Root hair curling and root hair deformation in the susceptible invasion zone is a sensitive in vivo assay for monitoring the legume plants ability to recognise a *Rhizobium* strain or the Nod-factor synthesized by a *Rhizobium* strain. The assay is performed on seedlings and established as follows. Seeds of wild type, transgenic and mutant *Lotus* spp are sterilised and germinated for 3 days. Seedlings are grown on ¼ B&D medium (Handberg and Stougaard, 1992 supra), between two layers of sterile wet filter paper for 3 days more. Afterwards, they are transferred into smaller petri dishes containing ¼ B&D medium supplemented with 12.7 nM AVG [(S)-trans-2-amino-4-(2-aminoethoxy)-3-butenoic acid hydrochloride] (Bras C. et al, 2000, *MPMI* 13: 475-479). On transfer, the seedlings are inoculated with either 20 µl of 1:100 dilution of a 2 days old *M. loti* strain NZP2235 culture, or with *M. loti* strain R7A Nod-factor coated sand, or with sterile water as a control, and a layer of wet dialysis membrane is used to cover the whole root. A minimum of 30 seedlings are microscopically analysed for specific deformations of the root hairs. The assay determines the threshold sensitivity of each *L. japonicus*, for the Nod-factor (LCO) of a given *Rhizobium* strain and the frequency of root hair curling and/or deformation.

In an alternative procedure, seeds of *Lotus japonicus* are surface sterilised and germinated for 4 days on 1% agar plates containing half-strength nitrogen-free medium (Imaizumi-Anraku et al., 1997, *Plant Cell Physiol.* 38: 871-881), at 26° C., under a 16 h light and 8 h dark regime. Straight roots, of <1 cm in length, on germlings from each cultivar are then selected and transplanted on Fåhraeus slides, in a nitrogen-free medium and grown for a further 2 days. LCOs, prepared by n-butanol extraction and HPLC separation from a given *Rhizobium* strain (Niwa et al., 2001, MPMI 14: 848-856), are applied to the straight roots in each cultivar, at a final concentration range of between $10^{-7}$ and $10^{-9}$ M. After 12 to 24 h culture, the roots are stained with 0.1% toluene blue and the number of root hairs showing curling is counted. The assay determines the threshold sensitivity of each *Lotus* spp., carrying a given NFR allele, for the Nod-factor (LCO) of a given *Rhizobium* strain and the frequency of root hair curling.

2. Determining the Frequency and Efficiency of Nodulation of NFR Alleles.

The efficiency of a legume plants ability to form root nodules after inoculation with a *Rhizobium* strain is determined in small scale controlled nodulation tests. *Lotus* seeds are surface sterilised in 2% hyperchlorite and cultivated under aseptic conditions in nitrogen free ¼ concentrated B&D medium. After 3 days of germination, seedlings are inoculated with a 2 days old culture of *M. loti* NZP2235 or TONO or R7A or with the *R. leguminosarum* by viceae 5560DZL strain. In principle a set of plants is only inoculated with one stain. For controlled competition experiments where legume-*Rhizobium* recognition is determined in a mixed *Rhizobium* population, a set of plants can be inoculated with more than one *Rhizobium* strain or with an extract from a particular soil. Two growth regimes are used: either petri dishes with solidified agar or Magenta jars with a solid support of burnt clay and vermiculite. The number of root nodules developed after a chosen time period is then counted, and the weight of the nodules developed can be determined. The efficiency of the root nodules in terms of nitrogen fixation can be determined in several ways, for example as the weight of the plants or directly as the amount of N15 nitrogen incorporated in the plant molecules.

In an alternative procedure, *Lotus* seeds are surface sterilised and vernalised at 4° C. for 2 days on agar plates and germinated overnight at 28° C. The seedlings are inoculated with *Mesorhizobium loti* strain NZP2235, TONO or R7A LCOs (as described above) and grown in petri dishes on Jensen agar medium at 20° C. in 8 h dark, 16 h light regime. The number of nodules present on the plant roots of each cultivar is determined at 3 days intervals over a period of 25 days, providing a measure of the rate of nodulation and the abundance of nodules per plant.

3. Determining Nodule Occupancy in Relation to NFR Allele

In agriculture the NFR Nod-factor binding element recognises *Rhizobium* bacteria under adverse soil conditions. The final measure of a particular strain's or commercial *Rhizobium* inoculum's ability to compete with the endogenous *Rhizobium* soil population for invasion of a legume crop with particular NFR alleles, is root nodule occupancy. The proportion of nodules formed after invasion by a particular strain and the fraction of the particular *Rhizobium* strain inside individual root nodules is determined by surface sterilising the root nodule surface in hyperchlorite, followed by crushing of the nodule into a crude extract and counting the colony forming *Rhizobium* units after dilution of the extract and plating on medium allowing *Rhizobium* growth (Vincent., J M. 1970, A manual for the practical study of root nodule bacteria. IBP handbook no. 15 Oxford Blackwell Scientific Publications, López-Garcia et al, 2001, *J Bacteriol,* 183, 7241-7252).

4. NFR1 and NFR5 are Determinants of Host Range in *Lotus-Rhizobium* Interactions.

Wild type *Lotus japonicus* Gifu is nodulated by both *Rhizobium leguminosarum* bv. viciae 5560 DZL (R. leg 5560DZL) and *Mesorhizobium loti* NZP2235 (*M. loti* NZP2235), while wild type *Lotus filicaulis* is only nodulated by *M. loti* NZP2235. Transgenic *Lotus filicaulis* plants expressing the NFR1 and NFR5 alleles of *Lotus japonicus* Gifu, are nodulated by R. leg 5560DZL, clearly demonstrating that the NFR alleles are the primary determinants of host range.

*Lotus filicaulis* was transformed with vectors comprising NFR1 and NFR5 wild type genes and their cognate promoters from *Lotus japonicus* Gifu or with empty vectors. The *Lotus filicaulis* transformants carrying NFR1 and NFR5 are nodulated by R. leg 5560DZL, albeit at reduced efficiency/frequency (9.6%) compared to *Lotus japonicus* Gifu (100%), as shown in Table 8. Mixing of NFR subunits from *Lotus japonicus* and *Lotus filicaulis* in the Nod-factor binding element is likely to contribute to the reduced efficiency observed. These data demonstrate that rhizobial strain recognition specificity is determined by the NFR1 and NFR5 alleles and that breeding for specific NFR alleles present in the germplasm or in wild relatives can be used to select optimal legume-*Rhizobium* partners.

Figure 12:
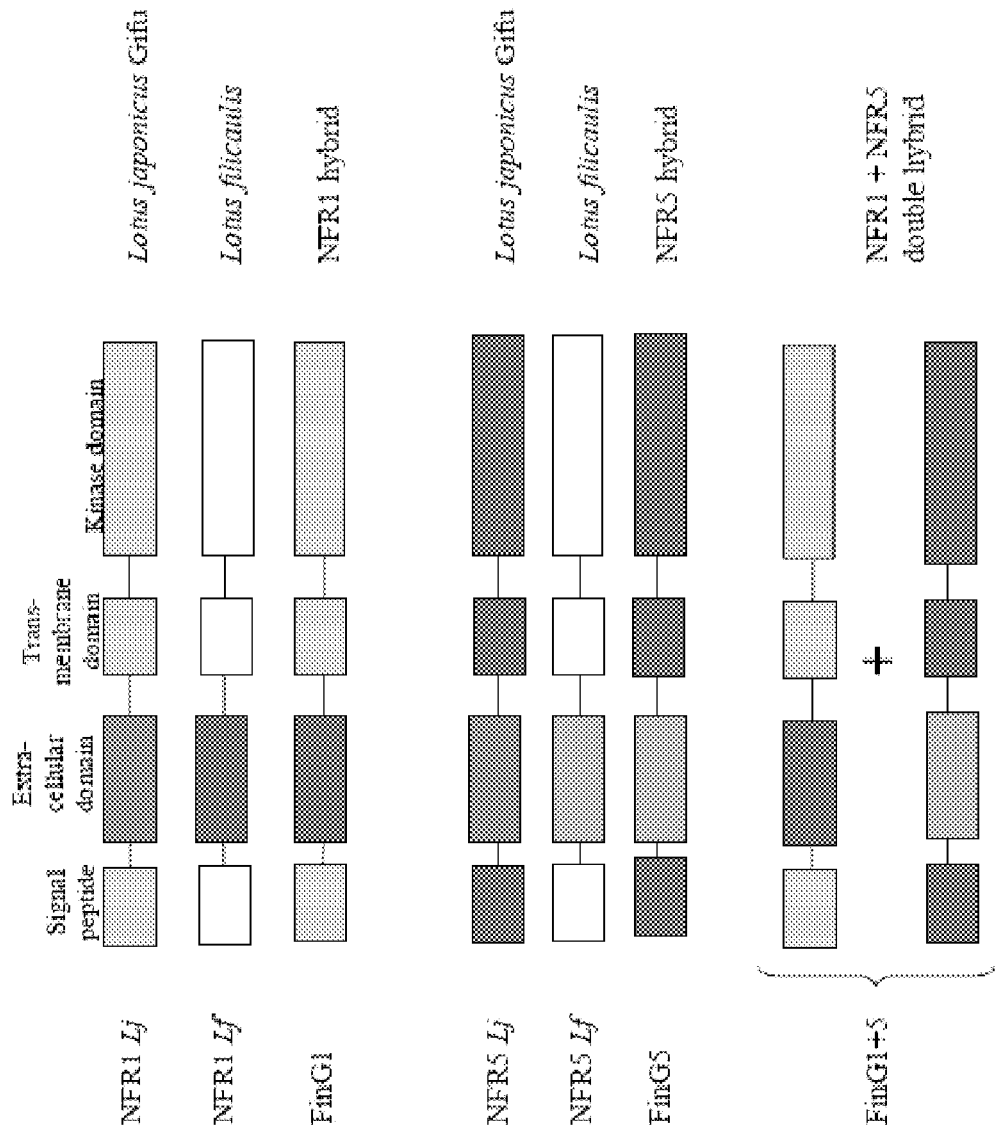

More detailed investigations show that the rhizobial strain recognition specificity of the NFR5 and NFR1 alleles is determined by the extracellular domain of the NFR5 and NFR1 proteins. Mutant *Lotus japonicus* nfr5 was transformed with a wild type hybrid NFR5 gene "FinG5", encoding the extracellular domain from *L. filicaulis* NFR5 fused to the kinase domain from *L. japonicus* Gifu NFR5 (FIG. 12). The hybrid gene was operably linked to the wild type NFR5 promoter. Control transformants, comprising wild type *L. japonicus* Gifu, *L. filicaulis* and the *Lotus japonicus* nfr5 mutant, transformed with an empty vector, are generated in parallel. The transformed plants are infected either with *M. loti* NZP2235 or with R. leg5560 DZL and the formation of nodules monitored, as shown in Table 9. The FinG5 hybrid gene complements the nfr5 mutation, and 88% of the transformants are nodulated by *M. loti* NZP2235 showing that the hybrid gene is functionally expressed. However, the nfr5 mutants expressing the FinG5 hybrid gene are very poorly nodulated by R.leg 5560 DZL, only 3%, (corresponding to one plant) even after prolonged infection (40 days). This demonstrates that strain specificity of the Nod-factor binding element is determined by the extracellular domain of its component NFR proteins.

In parallel, the *Lotus japonicus* nfr1 mutant was transformed with a wild type hybrid NFR1 gene "FinG1", encoding the extracellular domain from *L. filicaulis* NFR1 fused to the kinase domain from *L. japonicus* Gifu NFR1 (FIG. 12). The hybrid gene was operably linked to the wild type NFR1 promoter. The transformed plant were infected either with *M. loti* NZP2235 or with R. leg 5560 DZL and the formation of nodules was monitored, as shown in Table 10.

The FinG1 hybrid gene complements the nfr1-1 mutation, and 100% of the transformants were nodulated by *M. loti* NZP2235. However nfr1-1 mutants expressing the FinG1 hybrid gene were less efficiently nodulated (30-40%) by R. leg 5560 DZL. Furthermore, their nodulation by R. leg 5560 DZL was much delayed compared to their nodulation by *M. loti* NZP2235. Thus the *Lotus*/R. leg 5560 DZL interaction is less efficient and delayed when the transgenic host plant expresses a hybrid NFR1 comprising the extracellular domain of *Lotus filicaulis* NFR1 with the kinase domain of *Lotus japonicus* Gifu NFR1. These data indicate that the specific recognition of R. leg 5560 DZL by its *Lotus* host is at least partly specified by the extracellular domain of NFR1 (Gifu) and that this is an allele specific recognition. However, the NFR5 allele appears to be more important for specific recognition than NFR1.

5. NFR5 and NFR1 Alleles and Their Molecular Markers

The NFR5Nod-factor binding proteins encoded by the NFR5 alleles of *Lotus japonicus* ecotype GIFU (gene sequence: SEQ ID No: 7; protein sequence: SEQ ID No: 24 & 25), and *Lotus filicaulis* (gene sequence SEQ ID No: 30; protein sequence SEQ ID No: 31) have been compared, and found to show diversity in their primary structure. Using the sequence information available for the *Lotus* NFR5 gene together with the pea SYM10 gene (Table 12), the alleles from different ecotypes or varieties of *Lotus*, pea and other legumes can now be identified, and used directly in breeding programs. By further way of example, the nucleic acid sequence of the *Phaseolus vulgaris* NFR5 gene (SEQ ID No: 39) has facilitated the identification of a molecular marker for two different NFR5 alleles in the *Phaseolus vulgaris* lines Bat93 and Jalo EEP558, that is based on a single nucleotide difference creating an ApoI restriction site (RAATTY) in line Bat93, wherein R stands for A or G, Y for C or T. A partial sequence of the NFR5 gene comprising the ApoI site molecular marker identified in line Bat93 is shown in bold type:

CACAGGACATATTGAGTGAAAACAACTATGGTCAAAATTTCACTGCCGC

AAGCAACCTTCCAGTTTTGATCCCAGTTACA (SEQ ID No: 55)

The absence of this ApoI site in the comparable NFR5 partial sequence of line Jalo EEP558 is shown in bold type:

CACAGGACATATTGAGTGAAAACAACTATGGTCAAAACTTCACTGCCGC

AAGCAACCTTCCAGTTTTGATCCCAGTTACA (SEQ ID No: 56)

Molecular markers based on DNA polymorphism are used to detect the alleles in breeding populations. Similar use can be taken of the NFR1 sequences. Molecular DNA markers, based on the NFR5 allele sequence differences of *Lotus* and pea, are bolded in Table 12 and highlighted in Table 13 as examples of how DNA polymorphism can be used directly to detect the presence of an advantageous allele in a breeding population.

Breeding for an advantageous allele can also be carried out using molecular markers, that are genetically linked to the allele of interest, but located outside the gene-allele itself. Breeding of new *Lotus japonicus* lines containing a desired NFR5 allele can, for example, be facilitated by the use of DNA polymorphisms, (simple sequence repeats (microsatelittes) or single nucleotide polymorphism (SNP) which are found at loci, genetically linked to NFR5. Microsatelittes and SNPs at the NFR5 locus are identified by transferring markers from the general map, by identification of AFLP markers, or, by scanning the nucleotide sequence of the BAC and TAC clones spanning the NFR5 locus, for DNA polymorphic sequences located in close proximity of the NFR5 gene. Table 11 lists the markers closely linked to NFR5 and the sequence differences used to design the microsatelitte or SNP markers. This principle of marker assisted breeding, using genetically linked markers, can be applied to all plants. Microsatellite markers which generate PCR products with a high degree of polymorphism, are particularly useful for distinguishing closely related individuals, and hence to distinguish different NFR5 of NFR1 alleles in a breeding program.

TABLE 1

Alignment of Lotus, Glycine and Phaseolus NFR5 protein sequences

|  | 1 | 2 | 3 | 4 | 50 |
|---|---|---|---|---|---|
| Lotus | MAVFF-- | GSLSLFLALT | LLFTNIAARS | EKISGPDFSC | PVDSPPSCET |
| Glycine | MAVFFPFLPL | HSQILCLVIM | LFSTNIVAQS | QQDNRTNFSC | PSDSPPSCET |
| Phaseolus | MAVFFVSLTL | GAQILYVVLM | FFTC- | QQTNGTNFSC | PSNSPPSCET |

|  | 6 | 7 | 8 | 9 | 100 |
|---|---|---|---|---|---|
| Lotus | YVTYTAQSPN | LLSLTNISD | FDISPLSIA | ASNIDAGKDK | LVPGQVLLVP |
| Glycine | YVTYIAQSPN | FLSLTNISN | FDTSPLSIAR | ASNLEPMDDK | LVKDQVLLVP |
| Phaseolus | YVTYISQSPN | FLSLTSVSN | FDTSPLSIAR | ASNLQHEEDK | LIPGQVLLI |

|  | 11 | 12 | 13 | 14 | 150 |
|---|---|---|---|---|---|
| Lotus | VTCGCAGNHS | SANTSYQIQL | GDSYDFVATT | LYENLTNWNI | VQASNPGVNP |
| Glycine | VTCGCTGNRS | FANISYEINQ | GDSFYFVATT | SYENLTNWRA | VMDLNPVLSP |
| Phaseolus | VTCGCTGNRS | FANISYEINQ | GDSFYFVATT | LYQNLTNWHA | VMDLNPGLSQ |

TABLE 1-continued

Alignment of Lotus, Glycine and Phaseolus NFR5 protein sequences

```
                  16         17         18         19        200
Lotus      YLLPERVKVV FPLFCRCPSK NQLNKGIQYL ITYVWKPNDN VSLVSAKFGA
Glycine    NKLPIGIQVV FPLFCKCPSK NQLDKEIKYL ITYVWKPGDN VSLVSDKFGA
Phaseolus  FTLPIGIQV  IPLFCKCPSK NQLDRGIKYL ITHVWQPNDN VSFVSNKLGA 21         22         23         24        250
Lotus      SPADILTENR YGQDFTAATN LPILIPVTQ  PELTQPSSNG RKSSIHLLV
Glycine    SPEDIMSENN YGQNFTAANN LPVLIPVTR  PVLARSPSDG RKGGIRLPVI
Phaseolus  SPQDILSENN YGQNFTAASN LPVLIPVTL  PDLIQSPSDG RKHRIGLPVI 26         27         28         29        300
Lotus      LGITLGCTL  TAVLTGTLVY VYCRRKKALN RTASSAETAD KLLSGVSGYV
Glycine    IGISLGCTL  VLVLAVLLVY VYCLKMKTLN RSASSAETAD KLLSGVSGYV
Phaseolus  IGISLGCTL  VVVSAILLVC VCCLKMKSLN RSASSAETAD KLLSGVSGYV 31         32         33         34        350
Lotus      SKPNVYEIDE IMEATKDFSD ECKVGESVYK ANIEGRVVAV KKIKEGGANE
Glycine    SKPTMYETDA IMEATMNLSE QCKIGESVYK ANIEGKVLAV KRFKED-VTE
Phaseolus  SKPTMYETGA ILEATMNLSE QCKIGESVYK ANIEGKVLAV KRFKED-VTE 36         37         38         39        400
Lotus      ELKILQKVNH GNLVKLMGVS SGYDGNCFLV YEYAENGSLA EWLFSKS--
Glycine    ELKILQKVNH GNLVKLMGVS SDNDGNCFVV YEYAENGSLD EWLFSKSCSD
Phaseolus  ELKILQKVNH GNLVKLMGVS SDNDGNCFVV YEYAENGSLE EWLFAKSCSE 41         42         43         44        450
Lotus      -SGTPNSLTW SQRISIAVDV AVGLQYMHEH TYPRIIHRD  TTSNILLDSN
Glycine    TSNSRASLTW CQRISMAVDV AMGLQYMHEH AYPRIVHRDI TSSNILLDSN
Phaseolus  TSNSRTSLTW CQRISIAVDV SMGLQYMHEH AYPRIVHRDI TSSNILLDSN 46         47         48         49        500
Lotus      FKAKIANFAM ARTSTNPMMP KIDVFAFGVL LIELLTGRKA MTTKENGEVV
Glycine    FKAKIANFSM ARTFTNPMMP KIDVFAFGVV LIELLTGRKA MTTKENGEVV
Phaseolus  FKAKIANFSM ARTFTNPMMS KIDVFAFGVV LIELLTGRKA MTTKENGEVV 51         52         53         54        550
Lotus      MLWKDMWEIF DIEENREERI RKWMDPNLES FYHIDNALSL ASLAVNCTAD
Glycine    MLWKDIWKIF DQEENREERL KKWMDPKLES YYPIDYALSL ASLAVNCTAD
Phaseolus  MLWKDIWKIF DQEENREERL RKWMDPKLDN YYPIDYALSL ASLAVNCTAD 56         57         58         59        600
Lotus      KSLSRPSMAE IVLSLSFLT  QSSNPTLERS LTSSGLDVED DAHIVTSIT
Glycine    KSLSRPTIAE IVLSLSLLT  PSP-ATLERS LTSSGLDVEA -
Phaseolus  KSLSRPTIAE IVLSLSLLT  PSP-ATLERS LTSSGLDVEA -

61         62         63         65        650
Lotus      R....      ....       ....       ....       .... SEQ ID NO:  8
Glycine    R....      ....       ....       ....       .... SEQ ID NO: 48
Phaseolus  R....      ....       ....       ....       .... SEQ ID NO: 40
```

TABLE 2

|   | Lj | Pv | Gm |
|---|---|---|---|
| A. Sequence identity (%) between NFR5 cDNA coding sequences determined by pairwise sequence comparisons using NCBI BlastN | | | |
| Lj | 100 | | |
| Pv | 86 | 100 | |
| Gm | 80 | 90 | 100 |
| B. Sequence identity (%) between NFR5 protein sequences determined by pairwise sequence comparisons NCBI BlastP | | | |
| Lj | 100 | | |
| Pv | 70 | 100 | |
| Gm | 73 | 86 | 100 |

Lj = *Lotus japonicus*,
Pv = *Phaseolus vulgaris*,
Gm = *Glycine max*

TABLE 3

Alignment of Lotus and Pisum NFR1 protein sequences

```
               1           2          3          4         50
Pisum  MKLKNGLLLF  F-         KVESKCVIGC DIALASYYVM P-
Pisum  MKLKNGLLLF  F-         KVDSKCVKGC DLALASYYVM P-
Lotus  MKLKTGLLLF  FILLLGHVC  HVESNCLKGC DLALASYYI  PGVFILQNI 6           7          8          9        100
Pisum  TFMQSKLVTN  SFEVIVRYNR DIVFSNDNLF SYFRVNIPFP CECIGGEFLG
Pisum  NYMQSKIVTN  SSDVLNSYNK VLVTNHGNIF SYFRINIPF  CECIGGEFLG
Lotus  TFMQSEIVSS  N-         DKILNDINI  SFQRLNIPFP CDCIGGEFLG 11          12         13         14        150
Pisum  HVFEYTANEG  DTYDLIANTY YASLTTVEVL KKYNSYDPNH IPVKAKVNVT
Pisum  HVFEYTTKKG  DTYDLIANNY YVSLTSVELL KKFNSYDPNH IPAKAKVNVT
Lotus  HVFEYSASKG  DTYETIANL  YANLTTVDLL KRFNSYDPKN IPVNAKVNVT 16          17         18         19        200
Pisum  VNCSCGNSQI  SKDYGLFITY PLRPRDTLEK IARHSNLDEG VIQSYNLGVN
Pisum  VNCSCGNSQI  SKDYGLFVTY PLRSTDSLEK IANESKLDEG LIQNFNPDVN
Lotus  VNCSCGNSQV  SKDYGLFITY PIRPGDTLQD IANQSSLDAG LIQSFNPSVN 21          22         23         24        250
Pisum  FSKGSGVVFF  PGRDKNGEYV PLYPRT-GLG KGAAAGISI  GIFALLLF
Pisum  FSRGSGIVF   PGRDKNGEYV PLYPKT-GVG KGVAIGISI  GVFAVLLFV
Lotus  FSKDSGIAF   PGRYKNGVYV PLYHRTAGLA SGAAVGISI  GTFVLLLLA 26          27         28         29        300
Pisum  CIYIKYFQK   EEEKTKLP-Q VSTALSAQD- -ASGSGEYET SGSSGHGTGS
Pisum  CIYVKYFQKK  EEEKTILP-  VSKALSTQDG NASSSGEYET SGSSGHGTGS
Lotus  CMYVRY-QKK  EEEKAKLPTD ISMALSTQD  -ASSSAEYET SGSSGPGTAS 31          32         33         34        350
Pisum  TAGLTGIMVA  KSTEFSYQEL AKATNNFSLD NKIGQGGFGA VYYAVLRGEK
Pisum  AAGLTGIMVA  KSTEFSYQEL AKATDNFSLD NKIGQGGFGA VYYAELRGEK
Lotus  ATGLTSIMVA  KSMEFSYQEL AKATNNFSLD NKIGQGGFGA VYYAELRGKK 36          37         38         39        400
Pisum  TAIKKMDVQA  STEFLCELQV LTHVHHLNLV RLIGYCVEGS LFLVYEHID
Pisum  TAIKKMNVQA  SSEFLCELKV LTHVHHLNLV RLIGYCVEGS LFLVYEHID
Lotus  TAIKKMDVQA  STEFLCELKV LTHVHHLNLV RLIGYCVEGS LFLVYEHID 41          42         43         44        450
Pisum  GNLGQYLHGI  DKAPLPWSSR VQIALDSARG LEYIHEHTVP VYIHRDVKSA
Pisum  GNLGQYLHGK  DKEPLPWSSR VQIALDSARG LEYIHEHTVP VYIHRDVKSA
Lotus  GNLGQYLHGS  GKEPLPWSSR VQIALDAARG LEYIHEHTVP VYIHRDVKSA 46          47         48         49        500
Pisum  NILIDKNLH   KVADFGLTKL IEVGNSTLHT RLVGTFGYMP PEYAQYGDVS
Pisum  NILIDKNLR   KVADFGLTKL IEVGNSTLHT RLVGTFGYMP PEYAQYGDVS
Lotus  NILIDKNLR   KVADFGLTKL IEVGNSTLQT RLVGTFGYMP PEYAQYGDIS 51          52         53         54        550
Pisum  PKIDVYAFGV  VLYELISAK  AILKTGESAV -          EEALNQIDPL
Pisum  PKIDVYAFGV  VLYELISAK  AVLKTGEESV AESKGLVALF EKALNQIDPS
Lotus  PKIDVYAFGV  VLFELISAK  AVLKTGE-   AESKGLVALF EEALNKSDPC 56          57         58         59        600
Pisum  EALRKLVDPR  LKENYPIDSV LKMAQLGRAC TRDNPLLRPS MRSLVVALMT
Pisum  EALRKLVDPR  LKENYPIDSV LKMAQLGRAC TRDNPLLRPS MRSLVVDLMT
Lotus  DALRKLVDPR  LGENYPIDSV LKIAQLGRAC TRDNPLLRPS MRSLVVALMT 61          62         63         65        650
Pisum  LLSHTDD--   DTFYENQSLT NLLSVR..   ....       SEQ ID NO: 52
Pisum  LSSPFEDCDD  DTSYENQTLI NLLSVR..   ....       SEQ ID NO: 54
Lotus  LSSLTEDCDD  ESSYESQTLI NLLSVR..   ....       SEQ ID NO: 24
```

TABLE 4

| | Lj | PsNFR1a | PsNFR1B |
|---|---|---|---|
| A. Sequence identity (%) between NFR1 cDNA coding sequences determined by pairwise sequence comparisons using NCBI BlastN | | | |
| Lj | 100 | | |
| PsNFR1A | 84 | 100 | |
| PsNFR1B | 83 | 87 | 100 |
| B. Sequence identity (%) between NFR1 protein sequences determined by pairwise sequence comparisons NCBI BlastP | | | |
| Lj | 100 | | |

TABLE 4-continued

|  | Lj | PsNFR1a | PsNFR1B |
|---|---|---|---|
| PsNFR1A | 73 | 100 |  |
| PsNFR1B | 75 | 79 | 100 |

Lj = *Lotus japonicus*,
Ps = *Pisum sativum*

TABLE 5

Summary of *Lotus* nfr5 and pea sym10 mutant alleles

| Allele | Mutation | *Lotus* Spp |
|---|---|---|
| sym5-1 | EYAENGSLA 380-388 deletion | Lj |
| sym5-2 | retrotransposon integration after Q233 | Lj |
| sym5-3 | CAG→TAG, Q55→stop | Lj |
| RisFixG | TGG→TGA, W$_{388}$→stop | Ps |
| P5 | TGG→TGA, W$_{405}$→stop | Ps |
| P56 | CAA→TAA, Q$_{200}$→stop | Ps |
| N15 | Sym10 gene deleted | Ps |

TABLE 6

Complementation of *Lotus japonicus* nfr5 mutants with the wildtype NFR5 transgene

| *Lotus* genotype | Transgene | No. of plants | Infected With | No. of plants with nodules* | Total No. of nodules |
|---|---|---|---|---|---|
| nfr5-1 | NFR5 | 31 | *M. loti* NZP2235 | 18 | nd |
| nfr5-1 | Empty vector | 20 | *M. loti* NZP2235 | 0 | nd |
| nfr5-2 | NFR5 | 5 | *M. loti* NZP2235 | 1 | nd |
| nfr5-2 | Empty vector | 5 | *M. loti* NZP2235 | 0 | nd |

*Nodules only detected on transformed roots

TABLE 7

Transformation of *Lotus japonicus* nfr1 mutants with the wildtype NFR1 transgene

| *Lotus* genotype | Transgene | No. of plants | Infected With | No. plants with nodules | Total No. of nodules | Average No. nodules/plant |
|---|---|---|---|---|---|---|
| nfr1-1 | NFR1 | 103 | *M. loti* NZP2235 | 62* | 310 | 5 |
| nfr1-1 | Empty vector | 30 | *M. loti* NZP2235 | 0 | 0 | 0 |
| nfr1-2 | NFR1 | 20 | *M. loti* NZP2235 | 13* | 97 | 7.5 |
| nfr1-2 | empty vector | 7 | *M. loti* NZP2235 | 0 | 0 | 0 |

*Nodules only detected on transformed roots

TABLE 8

*Lotus filicaulis* transformed with wildtype NFR1 and NFR5 genes from *Lotus japonicus* Gifu

| *Lotus* genotype | Transgene | No. of plants | Infected with | No. plants with nodules | Total No. of nodules | Average No. nodules/plant |
|---|---|---|---|---|---|---|
| *Lotus filicaulis* | NFR1 + NFR5 | 104 | *R. leg* 5560 DZL | 10* | 25 | 2.5 |
| *Lotus filicaulis* | Empty vector | 65 | *R. leg* 5560 DZL | 0 | 0 | 0 |
| *Lotus japonicus* Gifu | Empty vector | 10 | *R. leg* 5560 DZL | 10** | >150 | >15 |

*Nodules only detected on transformed roots
**Nodules on normal and transformed roots

TABLE 9

*L. japonicus* nfr5 mutant transformed with a hybrid NFR5 gene "FinG5" encoding the extracellular domain of *L. filicaulis* NFR5 fused to the kinase domain from *L. japonicus* Gifu NFR5.

| Lotus genotype | Transgene | No. of plants | Infected with | No. of plants with nodules | Total No. of nodules | Average No. nodules/ plant |
|---|---|---|---|---|---|---|
| nfr5 | FinG5 | 31 | *M. loti* NZP2235 | 28* | ~180 | 6.4 |
| nfr5 | Empty vector | 12 | *M. loti* NZP2235 | 0 | 0 | |
| nfr5 | FinG5 | 34 | *R. leg* 5560 DZL | 1* | 4 | 4 1 PLANT ONLY |
| nfr5 | empty vector | 10 | *R. leg* 5560 DZL | 0 | 0 | |
| Lotus japonicus Gifu | empty vector | 10 | *R. leg* 5560 DZL | 10** | >150 | >15 |
| Lotus filicaulis | empty vector | 29 | *R. leg* 5560 DZL | 0 | 0 | |

*Nodules only detected on transformed roots
**Nodules on normal and transformed roots

TABLE 10

*L. japonicus* nfr1 mutant transformed with a hybrid NFR1 gene "FinG1" encoding the extracellular domain of *L. filicaulis* NFR1 fused to the kinase domain from *L. japonicus* Gifu NFR1.

| Lotus genotype | Transgene | No. of plants | Infected with | No. of plants with nodules | Total No. of nodules | Average No. nodules/ plant |
|---|---|---|---|---|---|---|
| nfr1-1 | FinG1 | 8 | *M. loti* NZP2235 | 8* | 59 | 7.3 |
| nfr1-1 | Empty vector | 6 | *M. loti* NZP2235 | 0 | 0 | 0 |
| nfr1-1 | FinG1 | 13 | *R. leg* 5560DZL | 5*# | 15 | 3 |
| nfr1-1 | Empty vector | 9 | *R. leg* 5560DZL | 0 | 0 | 0 |
| nfr1-2 | FinG1 | 10 | *R. leg* 5560DZL | 3*# | 12 | 4 |
| nfr1-2 | Empty vector | 4 | *R. leg* 5560DZL | 0 | 0 | 0 |

*Nodules only detected on transformed roots
Nodules were first counted after 56 days, while *M. loti* NZP2235 nodules were detectable after ~25 days.

TABLE 11

Molecular markers for NFR5 allele breeding in Lotus

| Marker | Genetic distance from Lotus NFR5 locus | Lotus Ecotype | Microsatellite sequence | SEQ ID NO: |
|---|---|---|---|---|
| TM0272 | 2.9 cM | MG-20 Gifu | 18xCT 12xCT | |
| TM0257 | 1.0 cM | MG-20 Gifu | 10xAAG 7xAAG | |
| LjT13i23Sfi | | Gifu Fili | TTTTGCTGCAGCAAGTCAGACTGTTAGAGGA TTTTGCTGCAACAAGTCGGACTGTTAGAGGA | 57 58 |
| TM0522 | 0 cM | MG-20 Gifu | 24xAT 14XAT | |
| NFR5 | | | | |
| E32M54-12F | 0.5 cM | MG-20 Fili | TTGGAAGTTCTTTTTATTAGGTTAATTTTA TTGGAAGTTCTTTTTA---GGTTAATTTTA | 59 60 |

TABLE 11-continued

Molecular markers for NFR5 allele breeding in Lotus

| Marker | Genetic distance from Lotus NFR5 locus | Ecotype | Microsatellite sequence | SEQ ID NO: |
|---|---|---|---|---|
| LjT01c03 | Not0.7 cM | Fili | CATTCCAGAAGAAAATAAGATATAATTATG | 61 |
| | | MG-20 | CATTCCAGAAGAAAATAAGATATAATTATG | 61 |
| | | Gifu | CATTCCAGAAG-AAATAAGATATAATTATG | 62 |
| TM0168 | 2.2 cM | MG-20 | 19xAT | |
| | | Gifu | 15xAT | |
| TM0021 | 3.8 cM | MG-20 | 16xCT | |
| | | Gifu | 13xCT | |

TABLE 12

Nucleotide sequence variation between
the pea SYM10 alleles of pea cultivars Frisson and Finale*

```
Frisson  CTTGCATTTC TTCACAATTT CACAACAATG GCTATCTTCT TCTTCCTTC
Finale   CTTGCATTTC TTCACAATTT CACAACAATG GCTATCTTCT TCTTCCTTC Frisson  TAGTTCTCAT GCCCTTTTTC TTGCACTCAT GTTTTTTGTC ACTAATATTT
Finale   TAGTTCTCAT GCCCTTTTTC TTGCACTCAT GTTTTTTGTC ACTAATATTT Frisson  CAGCTCAACC ATTACAACTC AGTGGAACAA ACTTTTCATG CCCGGTGGAT
Finale   CAGCTCAACC ATTACAACTC AGTGGAACAA ACTTTTCATG CCCGGTGGAT Frisson  TCACCTCCTT CATGTGAAAC CTATGTGACA TACTTTGCTC GGTCTCCAAA
Finale   TCACCTCCTT CATGTGAAAC CTATGTGACA TACTTTGCTC GGTCTCCAAA Frisson  CTTTTTGAGC CTAACTAACA TATCAGATAT ATTTGATATG AGTCCTTTAT
Finale   CTTTTTGAGC CTAACTAACA TATCAGATAT ATTTGATATG AGTCCTTTAT Frisson  CCATTGCAAA AGCCAGTAAC ATAGAAGATG AGGACAAGAA GCTGGTTGAA
Finale   CCATTGCAAA AGCCAGTAAC ATAGAAGATG AGGACAAGAA GCTGGTTGAA Frisson  GGCCAAGTCT TACTCATACC TGTAACTTGT GGTTGCACTA GAAATCGCTA
Finale   GGCCAAGTCT TACTCATACC TGTAACTTGT GGTTGCACTA GAAATCGCTA Frisson  TTTCGCGAAT TTCACGTACA CAATCAAGCT AGGTGACAAC TATTTCATAG
Finale   TTTCGCGAAT TTCACGTACA CAATCAAGCT AGGTGACAAC TATTTCATAG Frisson  TTTCAACCAC TTCATACCAG AATCTTACAA ATTATGTGGA AATGGAAAAT
Finale   TTTCAACCAC TTCATACCAG AATCTTACAA ATTATGTGGA AATGGAAAAT Frisson  TTCAACCCTA ATCTAAGTCC AAATCTATTG CCACCAGAAA TCAAAGTTGT
Finale   TTCAACCCTA ATCTAAGTCC AAATCTATTG CCACCAGAAA TCAAAGTTGT Frisson  TGTCCCTTTA TTCTGCAAAT GCCCCTCGAA GAATCAGTTG AGCAAAGGAA
Finale   TGTCCCTTTA TTCTGCAAAT GCCCCTCGAA GAATCAGTTG AGCAAAGGAA Frisson  TAAAGCATCT GATTACTTAT GTGTGGCAGG CTAATGACAA TGTTACCCGT
Finale   TAAAGCATCT GATTACTTAT GTGTGGCAGG CTAATGACAA TGTTACCCGT Frisson  GTAAGTTCCA AGTTTGGTGC ATCACAAGTG GATATGTTTA CTGAAAACAA
Finale   GTAAGTTCCA AGTTTGGTGC ATCACAAGTG GATATGTTTA CTGAAAACAA Frisson  TCAAAACTTC ACTGCTTCAA CCAACGTTCC GATTTTGATC CCTGTGACAA
Finale   TCAAAACTTC ACTGCTTCAA CCAATGTTCC GATTTTGATC CCTGTGACAA Frisson  AGTTACCGGT AATTGATCAA CCATCTTCAA ATGGAAGAAA AAACAGCACT
Finale   AGTTACCGGT AATTGATCAA CCATCTTCAA ATGGAAGAAA AAACAGCACT Frisson  CAAAAACCTG CTTTTATAAT TGGTATTAGC CTAGGATGTG CTTTTTTCGT
Finale   CAAAAACCTG CTTTTATAAT TGGTATTAGC CTAGGATGTG CTTTTTTCGT Frisson  TGTAGTTTTA ACACTATCAC TTGTTTATGT ATATTGTCTG AAAATGAAGA
Finale   TGTAGTTTTA ACACTATCAC TTGTTTATGT ATATTGTCTG AAAATGAAGA Frisson  GATTGAATAG GAGTACTTCA TTGGCGGAGA CTGCGGATAA GTTACTTTCA
Finale   GATTGAATAG GAGTACTTCA TTGGCGGAGA CTGCGGATAA GTTACTTTCA Frisson  GGTGTTTCGG GTTATGTAAG CAAGCCAACA ATGTATGAAA TGGATGCGAT
Finale   GGTGTTTCGG GTTATGTAAG CAAGCCAACA ATGTATGAAA TGGATGCGAT
```

TABLE 12-continued

Nucleotide sequence variation between
the pea SYM10 alleles of pea cultivars Frisson and Finale*

```
Frisson   CATGGAAGCT ACAATGAACC TGAGTGAGAA TTGTAAGATT GGTGAATCCG
Finale    CATGGAAGCT ACAATGAACC TGAGTGAGAA TTGTAAGATT GGTGAATCTG Frisson   TTTACAAGGC TAATATAGAT GGTAGAGTTT TAGCAGTGAA AAAAATCAAG
Finale    TTTACAAGGC TAATATAGAT GGTAGAGTTT TAGCAGTGAA AAAAATCAAG Frisson   AAAGATGCTT CTGAGGAGCT GAAAATTTTG CAGAAGGTAA ATCATGGAAA
Finale    AAAGATGCTT CTGAGGAGCT GAAAATTCTG CAGAAGGTAA ATCATGGAAA Frisson   TCTTGTGAAA CTTATGGGTG TGTCTTCCGA CAACGACGGA AACTGTTTCC
Finale    TCTTGTGAAA CTTATGGGTG TGTCTTCCGA CAACGAAGGA AACTGTTTCC Frisson   TTGTTTACGA GTATGCTGAA AATGGATCAC TTGATGAGTG GTTGTTCTCA
Finale    TTGTTTACGA GTATGCTGAA AATGGATCAC TTGATGAGTG GTTGTTCTCA Frisson   GAGTCGTCGA AAACTTCGAA CTCGGTGGTC TCGCTTACAT GGTCTCAGAG
Finale    GAGTTGTCGA AAACTTCGAA CTCGGTGGTC TCGCTTACAT GGTCTCAGAG Frisson   AATAACAGTA GCAGTGGATG TTGCAGTTGG TTTGCAATAC ATGCATGAAC
Finale    AATAACAGTA GCAGTGGATG TTGCAGTTGG TTTGCAATAC ATGCATGAAC Frisson   ATACTTACCC AAGAATAATC CACAGAGACA TCACAACAAG TAATATCCTT
Finale    ATACTTACCC AAGAATAATC CACAGAGACA TCACAACAAG TAATATCCTT Frisson   CTGGATTCAA ACTTTAAGGC CAAGATAGCG AATTTTTCAA TGGCCAGAAC
Finale    CTGGATTCAA ACTTTAAGGC CAAGATAGCG AATTTTTCAA TGGCCAGAAC Frisson   TTCAACAAAT TCCATGATGC CGAAAATCGA TGTTTTCGCT TTTGGGGTGG
Finale    TTCAACAAAT TCCATGATGC CGAAAATCGA TGTTTTCGCT TTTGGGGTGG Frisson   TTCTGATTGA GTTGCTTACC GGCAAGAAAG CGATAACAAC GATGGAAAAT
Finale    TTCTGATTGA GTTGCTTACC GGCAAGAAAG CGATAACAAC GATGGAAAAT Frisson   GGCGAGGTGG TTATTCTGTG GAAGGATTTC TGGAAGATTT TTGATCTAGA
Finale    GGCGAGGTGG TTATTCTGTG GAAGGATTTC TGGAAGATTT TTGATCTAGA Frisson   AGGGAATAGA GAAGAGAGCT TAAGAAAATG GATGGATCCT AAGCTAGAGA
Finale    AGGGAATAGA GAAGAGAGCT TAAGAAAATG GATGGATCCT AAGCTAGAGA Frisson   ATTTTTATCC TATTGATAAT GCTCTTAGTT TGGCTTCTTT GGCAGTGAAT
Finale    ATTTTTATCC TATTGATAAT GCTCTTAGTT TGGCTTCTTT GGCAGTGAAT Frisson   TGTACTGCAG ATAAATCATT GTCAAGACCA AGCATTGCAG AAATTGTTCT
Finale    TGTACTGCAG ATAAATCATT GTCAAGACCA AGCATTGCAG AAATTGTTCT Frisson   TTGTCTTTCT CTTCTCAATC AATCATCATC TGAACCAATG TTAGAAAGAT
Finale    TTGTCTTTCT CTTCTCAATC AATCATCATC TGAACCAATG TTAGAAAGAT Frisson   CCTTGACATC TGGTTTAGAT GTTGAAGCTA CTCATGTTGT TACTTCTATA
Finale    CCTTGACATC TGGTTTAGAT GTTGAAGCTA CTCATGTTGT TACTTCTATA Frisson   GTAGCTCGTT GATATTCATT CAAGTGAAGG TAACACTGAA TCAATGCTTC
Finale    GTAGCTCGTT GATATTCATT CAAGTGAAGG TAACACTAAA TCAATGCTTC Frisson   AGTTTCTTAT ATTCAAGATG GTTACTTTGT TTAGATGATT ATTGATTACA
Finale    AGTTTCTTAT ATTCAAGATG GTTACTTTGT TTAGGTGATT ATTGATTACA Frisson   TCTTTATGTG TGGAACTATA TGGTTATTTT AATTAAGGGA ATTGTTCTAA
Finale    TCTTTATGTG TGGAACTATA TGGTTATTTT AATTAAGGGA ATTAGTCTAA Frisson   AATTCATTTT TCCATGTT       SEQ ID NO: 13
Finale    ATTTCATTTT TCCATGTT       SEQ ID NO: 12
```

*Nucleotide differences are bolded and the coding region is underlined

TABLE 13

Protein sequence differences encoded by the pea SYM10 alleles of pea cultivars Frisson and Finale*

| | | | | | |
|---|---|---|---|---|---|
| Frisson | MAIFFLPSSS | HALFLALMFF | VTNISAQPLQ | LSGTNFSCPV | DSPPSCETYV |
| Finale | MAIFFLPSSS | HALFLALMFF | VTNISAQPLQ | LSGTNFSCPV | DSPPSCETYV |
| Frisson | TYFARSPNFL | SLTNISDIFD | MSPLSIAKAS | NIEDEDKKLV | EGQVLLIPVT |
| Finale | TYFARSPNFL | SLTNISDIFD | MSPLSIAKAS | NIEDEDKKLV | EGQVLLIPVT |
| Frisson | CGCTRNRYFA | NFTYTIKLGD | NYFIVSTTSY | QNLTNYVEME | NFNPNLSPNL |
| Finale | CGCTRNRYFA | NFTYTIKLGD | NYFIVSTTSY | QNLTNYVEME | NFNPNLSPNL |
| Frisson | LPPEIKVVVP | LFCKCPSKNQ | LSKGIKHLIT | YVWQANDNVT | RVSSKFGASQ |
| Finale | LPPEIKVVVP | LFCKCPSKNQ | LSKGIKHLIT | YVWQANDNVT | RVSSKFGASQ |
| Frisson | VDMFTENNQN | FTASTNVPIL | IPVTKLPVID | QPSSNGRKNS | TQKPAFIIGI |
| Finale | VDMFTENNQN | FTASTNVPIL | IPVTKLPVID | QPSSNGRKNS | TQKPAFIIGI |
| Frisson | SLGCAFFVVV | LTLSLVYVYC | LKMKRLNRST | SLAETADKLL | SGVSGYVSKP |
| Finale | SLGCAFFVVV | LTLSLVYVYC | LKMKRLNRST | SLAETADKLL | SGVSGYVSKP |
| Frisson | TMYEMDAIME | ATMNLSENCK | IGESVYKANI | DGRVLAVKKI | KKDASEELKI |
| Finale | TMYEMDAIME | ATMNLSENCK | IGESVYKANI | DGRVLAVKKI | KKDASEELKI |
| Frisson | LQKVNHGNLV | KLMGVSSDND | GNCFLVYEYA | ENGSLDEWLF | SESSKTSNSV |
| Finale | LQKVNHGNLV | KLMGVSSDNE | GNCFLVYEYA | ENGSLDEWLF | SELSKTSNSV |
| Frisson | VSLTWSQRIT | VAVDVAVGLQ | YMHEHTYPRI | IHRDITTSNI | LLDSNFKAKI |
| Finale | VSLTWSQRIT | VAVDVAVGLQ | YMHEHTYPRI | IHRDITTSNI | LLDSNFKAKI |
| Frisson | ANFSMARTST | NSMMPKIDVF | AFGVVLIELL | TGKKAITTME | NGEVVILWKD |
| Finale | ANFSMARTST | NSMMPKIDVF | AFGVVLIELL | TGKKAITTME | NGEVVILWKD |
| Frisson | FWKIFDLEGN | REESLRKWMD | PKLENFYPID | NALSLASLAV | NCTADKSLSR |
| Finale | FWKIFDLEGN | REESLRKWMD | PKLENFYPID | NALSLASLAV | NCTADKSLSR |
| Frisson | PSIAEIVLCL | SLLNQSSSEP | MLERSLTSGL | DVEATHVVTS | IVAR |
| Finale | PSIAEIVLCL | SLLNQSSSEP | MLERSLTSGT | DVEATHVVTS | IVAR |

*Amino acid differences are highlighted in black.

The invention claimed is:

1. An isolated Nod-factor binding polypeptide comprising: at least 80% amino acid sequence identity to any one of SEQ ID NO: 8, 15, 31, 32, 40, or 48, wherein said polypeptide comprises an extracellular domain comprising 2 or 3 different LysM-type motifs, and wherein said polypeptide selectively binds strain-specific forms of Nod-Factor.

2. An isolated Nod-factor binding polypeptide comprising: at least 80% amino acid sequence identity to any one of SEQ ID NO: 24 or 25, wherein said polypeptide comprises an extracellular domain comprising 2 or 3 different LysM-type motifs, and wherein said polypeptide selectively binds strain-specific forms of Nod-Factor.

3. A method of producing a transgenic plant expressing a Nod-factor binding polypeptide, the method comprising:
   a. introducing into the plant a nucleic acid molecule encoding one or more Nod-factor binding polypeptide of claim 2, wherein the nucleic acid molecule is operably linked to a promoter; and
   b. selecting transgenic plants expressing the Nod-factor binding polypeptide.

4. The isolated Nod-factor binding polypeptide of claim 2, wherein said polypeptide comprises the amino acid sequence of any one of SEQ ID NO: 24 or 25.

5. An isolated Nod-factor binding element comprising one or more isolated Nod-factor binding polypeptide of claim 1, and further comprising one or more isolated Nod-factor binding polypeptide comprising at least 80% amino acid sequence identity to any one of SEQ ID NO: 24, 25, 52, or 54, wherein said polypeptide comprises an extracellular domain comprising 2 or 3 different LysM-type motifs, and wherein said polypeptide selectively binds strain-specific forms of Nod-Factor.

6. An isolated Nod-factor binding element comprising one or more isolated Nod-factor binding polypeptide of claim 3, and further comprising one or more polypeptide comprising the amino acid sequence of any one of SEQ ID NO: 24, 25, 52, or 54.

7. An isolated nucleic acid molecule encoding the Nod-factor binding polypeptide of claim 1.

8. An isolated nucleic acid molecule encoding the Nod-factor binding polypeptide of claim 2.

9. The isolated nucleic acid molecule of claim 7, wherein said nucleic acid molecule comprises the nucleotide sequence of SEQ ID NO: 6, 7, 11, 12, 30, 39, or 47.

10. The isolated nucleic acid molecule of claim 8, wherein said nucleic acid molecule comprises the nucleotide sequence of SEQ ID NO: 21, 22, or 23.

11. A transgenic cell stably transformed with one or more nucleic acid molecule encoding the Nod-factor binding polypeptide of claim 1.

12. The transgenic cell of claim 11, wherein said nucleic acid molecule encodes a polypeptide having the sequence of SEQ ID NOS: 8, 15, 31, 32, 40, or 48.

13. The transgenic cell of claim 11, wherein said nucleic acid molecule comprises the sequence of SEQ ID NOS: 6, 7, 11, 12, 30, 39, or 47.

14. A transgenic cell stably transformed with one or more nucleic acid molecule encoding the Nod-factor binding polypeptide of claim 2.

15. The transgenic cell of claim 14, wherein said nucleic acid molecule encodes a polypeptide having the sequence of SEQ ID NOS: 24 or 25.

16. The transgenic cell of claim 14, wherein said nucleic acid molecule comprises the sequence of SEQ ID NOS: 21, 22, or 23.

17. A transgenic cell comprising one or more transgene encoding the Nod Factor binding element of claim 5.

18. A transgenic cell comprising one or more transgene encoding the Nod Factor binding element of claim 6.

19. A method of producing a transgenic plant expressing a Nod-factor binding polypeptide, the method comprising:
   a. introducing into the plant a nucleic acid molecule encoding one or more Nod-factor binding polypeptide of claim 1, wherein the nucleic acid molecule is operably linked to a promoter; and
   b. selecting transgenic plants expressing the Nod-factor binding polypeptide.

20. The method of claim 19, wherein said nucleic acid molecule encodes a polypeptide having the amino acid sequence of SEQ ID NO: 8, 15, 31, 32, 40, or 48.

21. The method of claim 19, wherein said nucleic acid molecule comprises the sequence of SEQ ID NO: 6, 7, 11, 12, 30, 39, or 47.

22. A method of producing a transgenic plant expressing a Nod-factor binding polypeptide, the method comprising:
   a. introducing into the plant a nucleic acid molecule encoding one or more Nod-factor binding polypeptide of claim 2, wherein the nucleic acid sequence is operably linked to a promoter; and
   b. selecting transgenic plants expressing the Nod-factor binding polypeptide.

23. The method of claim 22, wherein said nucleic acid molecule encodes a polypeptide having the amino acid sequence of SEQ ID NO: 24 or 25.

24. The method of claim 22, wherein said nucleic acid molecule comprises the sequence of SEQ ID NO: 21, 22, or 23.

25. The method of claim 19, further comprising introducing into the plant one or more nucleic acid molecule encoding a polypeptide having at least 80% amino acid sequence identity to SEQ ID NO: 24, 25, 52, or 54.

26. The method of claim 20, comprising:
   introducing into the plant one or more nucleic acid molecule encoding a polypeptide having the amino acid sequence of SEQ ID NO: 8, 15, 31, 32, 40, or 48; and further introducing into the plant one or more nucleic acid molecule encoding a polypeptide having the amino acid sequence of SEQ ID NO: 24, 25, 52, or 54.

27. The method of claim 25, comprising introducing into the plant one or more nucleic acid molecule comprising SEQ ID NO: 6, 7, 11, 12, 30, 39, or 47; and further introducing one or more nucleic acid molecule comprising SEQ ID NO: 21, 22, 23, 51, or 53.

28. The method of claim 19, wherein one or more nucleic acid molecule is introduced into the plant through a sexual cross.

29. The method of claim 22, wherein one or more nucleic acid molecule is introduced into the plant through a sexual cross.

30. The method of claim 25, wherein one or more nucleic acid molecule is introduced into the plant through a sexual cross.

31. The method of claim 27, wherein one or more nucleic acid molecule is introduced into the plant through a sexual cross.

32. A transgenic plant comprising one or more transgene encoding the Nod-factor binding polypeptide of claim 1.

33. The transgenic plant of claim 32, wherein the polypeptide comprises the amino acid sequence of SEQ ID NO: 8, 15, 31, 32, 40, or 48.

34. A transgenic plant comprising one or more transgene encoding the Nod-factor binding polypeptide of claim 2.

35. The transgenic plant of claim 34, wherein the polypeptide comprises the amino acid sequence of SEQ ID NO: 24 or 25.

36. A transgenic plant comprising one or more transgene encoding the Nod-factor binding element of claim 5.

37. A transgenic plant comprising one or more transgene encoding the Nod-factor binding element of claim 6.

38. The transgenic plant of claim 32, wherein said plant is a cereal.

39. The transgenic plant of claim 34, wherein said plant is a cereal.

40. The transgenic plant of claim 32, wherein said plant is a legume.

41. The transgenic plant of claim 34, wherein said plant is a legume.

42. The transgenic plant of claim 32, wherein said plant is a non-nodulating plant.

43. The transgenic plant of claim 34, wherein said plant is a non-nodulating plant.

44. An isolated Nod-factor binding polypeptide comprising:
   at least 90% amino acid sequence identity to SEQ ID NO: 52 or 54, wherein said polypeptide comprises an extracellular domain comprising 2 or 3 different LysM-type motifs, and wherein said polypeptide selectively binds strain-specific forms of Nod-Factor.

45. An isolated nucleic acid molecule encoding the Nod-factor binding polypeptide of claim 44.

46. A transgenic cell stably transformed with one or more nucleic acid molecule encoding the Nod-factor binding polypeptide of claim 44.

47. The transgenic cell of claim 46, wherein said nucleic acid molecule comprises the nucleotide sequence of SEQ ID NO: 51 or 53.

48. A transgenic plant comprising one or more transgene encoding the Nod-factor binding polypeptide of claim 44.

49. The transgenic plant of claim 32, wherein the transgene encodes a polypeptide comprising at least 80% amino acid sequence identity to SEQ ID NO: 8.

50. The transgenic plant of claim 32, wherein the transgene encodes a polypeptide comprising at least 80% amino acid sequence identity to SEQ ID NO: 15.

51. The transgenic plant of claim 32, wherein the transgene encodes a polypeptide comprising at least 80% amino acid sequence identity to SEQ ID NO: 31.

52. The transgenic plant of claim 32, wherein the transgene encodes a polypeptide comprising at least 80% amino acid sequence identity to SEQ ID NO: 32.

53. The transgenic plant of claim 32, wherein the transgene encodes a polypeptide comprising at least 80% amino acid sequence identity to SEQ ID NO: 40.

54. The transgenic plant of claim 32, wherein the transgene encodes a polypeptide comprising at least 80% amino acid sequence identity to SEQ ID NO: 48.

55. The transgenic plant of claim 34, wherein the transgene encodes a polypeptide comprising at least 80% amino acid sequence identity to SEQ ID NO: 24.

56. The transgenic plant of claim 32, wherein the transgene encodes a polypeptide comprising the sequence of SEQ ID NO: 8.

57. The transgenic plant of claim 32, wherein the transgene encodes a polypeptide comprising the sequence of SEQ ID NO: 15.

58. The transgenic plant of claim 32, wherein the transgene encodes a polypeptide comprising the sequence of SEQ ID NO: 31.

59. The transgenic plant of claim 32, wherein the transgene encodes a polypeptide comprising the sequence of SEQ ID NO: 32.

60. The transgenic plant of claim 32, wherein the transgene encodes a polypeptide comprising the sequence of SEQ ID NO: 40.

61. The transgenic plant of claim 32, wherein the transgene encodes a polypeptide comprising the sequence of SEQ ID NO: 48.

62. The transgenic plant of claim 34, wherein the transgene encodes a polypeptide comprising the sequence of SEQ ID NO: 24.

63. The transgenic plant of claim 48, wherein the transgene encodes a polypeptide comprising the sequence of SEQ ID NO: 52.

* * * * *